US008314121B2

(12) United States Patent
Leroy et al.

(10) Patent No.: US 8,314,121 B2
(45) Date of Patent: Nov. 20, 2012

(54) IMIDAZOLONE DERIVATIVES, PREPARATION THEREOF AS DRUGS, PHARMACEUTICAL COMPOSITIONS, AND USE THEREOF AS PROTEIN KINASE INHIBITORS, IN PARTICULAR CDC7

(75) Inventors: Vincent Leroy, Paris (FR); Eric Bacque, Paris (FR); Emmanuel Conseiller, Paris (FR); Anke Steinmetz, Paris (FR); Baptiste Ronan, Paris (FR); Jean-Philippe Letallec, Paris (FR)

(73) Assignee: Sanofi, Paris (FR)

( * ) Notice: Subject to any disclaimer, the term of this patent is extended or adjusted under 35 U.S.C. 154(b) by 528 days.

(21) Appl. No.: 12/415,391

(22) Filed: Mar. 31, 2009

(65) Prior Publication Data
US 2009/0253679 A1 Oct. 8, 2009

Related U.S. Application Data

(63) Continuation of application No. PCT/FR2007/001651, filed on Oct. 10, 2007.

(30) Foreign Application Priority Data

Oct. 12, 2006 (FR) ..................................... 06 08924

(51) Int. Cl.
A01N 43/42 (2006.01)
A01N 43/00 (2006.01)
A61K 31/44 (2006.01)
A61K 31/00 (2006.01)
A61K 31/535 (2006.01)
C07C 241/00 (2006.01)
C07C 243/00 (2006.01)

(52) U.S. Cl. ................ 514/300; 514/210.21; 514/233.8; 546/113

(58) Field of Classification Search ............. 514/210.21, 514/300, 233.8; 546/113
See application file for complete search history.

(56) References Cited

U.S. PATENT DOCUMENTS

2007/0112020 A1* 5/2007 Vanotti et al. ................. 514/300

FOREIGN PATENT DOCUMENTS

| WO | WO 01/98299 A1 | 12/2001 |
|---|---|---|
| WO | WO 2004/078756 | 9/2004 |
| WO | WO 2005/014572 | 2/2005 |
| WO | WO 2005/103050 | 11/2005 |
| WO | WO 2006/040049 | 4/2006 |

OTHER PUBLICATIONS

Chan, A. C., et. al., The Role of Protein Tyrosine Kinases and Protein Tyrosine Phosphatases in T Cell Antigen Receptor Signal Transduction, Annu. Rev. Immunol., (1994), vol. 12, pp. 555-592.
Chezal, J. M., et. al., Heterocyclization of Functionalized Vinylic Derivatives of Imidazo[1,2-a] Pyridines, J. Org. Chem, (2001), vol. 66, pp. 6576-6584.
Connolly, D. J., et. al., A Facile and Versatile Route to 2-Substituted-4(3H)-Quinazolinones and Quinazoles, Synletter, (2001), vol. 11, pp. 1707-1710.
Gibson, C. S., et. al., CCCXXXIII.-Syntheses with BB-Dichlorodiethyl Ether. Part I. Derivatives of Tetrahydropyran, J. Chem. Soc., (1930), pp. 2525-2530.
Hanks, S. K., et. al., The Eukaryotic Protein Kinase Superfamily: Kinase (Catalytic) Domain Structure and Classification, FASEB J., vol. 9, (1995), pp. 576-596.
Iwashita, S., et. al., Signal Transduction System for Growth Factor Receptors Associated with Tyrosine Kinase Activity: Epidermal Growth Factor Receptor Signalling and its Regulation, Cellular Signalling, vol. 4, No. 2, (1992), pp. 123-132.
Kang, J. H., et. al., Synthesis of 2-Arylsubstituted Imidazolone Derivatives, Bull. Korean Chem. Soc., vol. 28, No. 6, pp. 913-914, (2007).
Mazeas, D., et. al., Synthesis of New Melatoninergic Ligands Including Azaindole Moiety, Heterocycles, vol. 50, No. 2, (1999), pp. 1065-1080.
Montagnoli, A., et. al., Cdc7 Inhibition Reveals a P53-Dependent Replication Checkpoint That is Defective in Cancer Cells, Cancer Research, vol. 64, pp. 7110-7116, (2004).
Newton, A. C., et. al., Protein Kinase C: Structure, Function, and Regulation, J. Biol. Chem., vol. 270, No. 48, 1995, pp. 28495-28498.
Pines, J., et. al., Cyclins and cyclin-dependent kinases: take your partners, Trends in Biochemical Sciences, vol. 18, 1993, pp. 195-197.
Thibault, C., et. al., Concise and Efficient Synthesis of 4-Fluoro-1 H-Pyrrolo[2,3-b]Pyridine, Organic Letters, (2003), vol. 5, No. 26, pp. 5023-5025.
Williams, D. L., et. al., The Glyoxalines. V. The Bromination of 2-Phenyl-4-Benzal-5-Glyoxalidone, J. Am. Chem. Soc., (1946), pp. 647-649.
4-Imidazolidinone, 3-Methyl-5- (1H-Pyrrolo[2,3-b]Pyridin-3-ylmethylene)-2-Thioxo-, Timetec Overseas Stock, Database Chemcats Chemical Abstracts Service, (2005), pp. 1.

* cited by examiner

*Primary Examiner* — Samira Jean-Louis
(74) *Attorney, Agent, or Firm* — Scully, Scott, Murphy & Presser, P.C.

(57) ABSTRACT

The present invention relates to imidazolone derivatives of formula (I)

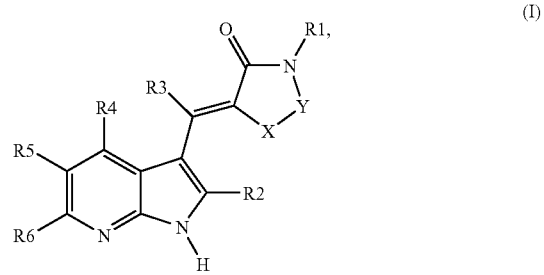

to methods of preparing such derivatives, intermediates thereto, pharmaceutical compositions comprising such derivatives, and methods of inhibiting protein kinase, and methods of treatment comprising administration of such derivatives.

17 Claims, No Drawings

IMIDAZOLONE DERIVATIVES, PREPARATION THEREOF AS DRUGS, PHARMACEUTICAL COMPOSITIONS, AND USE THEREOF AS PROTEIN KINASE INHIBITORS, IN PARTICULAR CDC7

The present invention relates to novel derivatives of imidazolones, the method of preparation thereof, the novel intermediates obtained, their application as medicinal products, pharmaceutical compositions containing them and novel uses of said imidazolone derivatives.

The invention thus relates to novel derivatives of imidazolones having inhibitory effects with respect to protein kinases.

The products of the present invention can thus notably be used for the prevention or the treatment of disorders that can be controlled by inhibiting the activity of protein kinases.

The products of the present application, as inhibitors of protein kinases, can be used quite particularly for the treatment or prevention of cancers. Cancer is a disease for which existing treatments are still inadequate. Certain protein kinases play an important role in many cancers. Inhibition of these protein kinases is potentially important in the chemotherapy of cancers, notably for suppressing tumour growth or survival.

The present invention therefore relates to the identification of novel products which inhibit said protein kinases.

The inhibition and regulation of protein kinases notably represent a powerful new mechanism of action for the treatment of a broad number of solid tumours.

Disorders that can be treated with the products of the present application are therefore quite particularly solid tumours.

Protein Kinases

The protein kinases constitute a group of enzymes that catalyse the phosphorylation of hydroxy groups of specific protein residues such as tyrosine, serine or threonine residues. Said phosphorylations can extensively modify the function of proteins; thus, the protein kinases play an important role in the regulation of a great variety of cellular processes, notably including metabolism, cellular proliferation, cell differentiation or cell survival. Among the various cellular functions in which the activity of a protein kinase is involved, certain processes represent attractive targets for treating certain diseases. As an example, we may notably mention angiogenesis and control of the cell cycle, in which the protein kinases can play an essential role. These processes are essential for the growth of solid tumours as well as for the development of other diseases.

The protein kinases participate in signalling events that control the activation, growth and differentiation of cells in response either to extracellular mediators, or to changes in the environment. In general, these kinases belong to two groups: those which phosphorylate serine and/or threonine residues preferentially, and those which phosphorylate tyrosine residues preferentially [S. K. Hanks and T. Hunter, FASEB. J., 1995, 9, pages 576-596]. The serine/threonine kinases, for example, are isoforms of protein kinases C [A. C. Newton, J. Biol. Chem., 1995, 270, pages 28495-28498] and a group of cyclin-dependent kinases, such as Cdc2 (Cdk1) [J. Pines, Trends in Biochemical Sciences, 1995, 18, pages 195-197]. The tyrosine kinases include growth factor receptors, such as the epidermal growth factor (EGF) receptor [S. Iwashita and M. Kobayashi, Cellular Signalling, 1992, 4, pages 123-132], and cytosolic kinases such as p56tck, p59fYn, ZAP-70 and the csk kinases [C. Chan et al., Ann. Rev. Immunol., 1994, 12, pages 555-592].

Abnormally high levels of protein kinase activity have been associated with many diseases, resulting in abnormal cellular functions. This can occur either directly or indirectly, from a malfunction in the control mechanisms of kinase activity, connected for example with a mutation, overexpression or inappropriate activation of the enzyme, or with overproduction or underproduction of cytokines or of growth factors, which are also involved in signal transduction upstream or downstream of the kinases. In all these cases, selective inhibition of the action of the kinases offers hope of a beneficial effect.

Among these protein kinases, we may mention quite particularly protein kinase Cdc7.

Cdc7 is a serine/threonine kinase that has been characterized at the molecular level as a factor that is essential for initiating DNA replication.

The catalytic activity of Cdc7, which is conserved throughout the eukaryotes, is dependent on its Dbf4 regulatory subunit. Although the expression of Cdc7 (at the level of messenger and protein RNA) is constant throughout the cell cycle, the level of expression of Dbf4 is in contrast dependent on the cell cycle, which induces an increase in Cdc7 kinase activity during the G1-S transition. For this reason, Cdc7 is given the designation DDK (Dbf-4-dependent kinase).

The principal activity of the Cdc7/Dbf4 complex occurs on initiation of DNA replication during the S phase. It phosphorylates MCM2 which thus activates the MCM (Mini-Chromosome Maintenance) complex, which is an essential component of DNA-helicase activity.

Cdc7 also plays an important role in mutagenesis, mainly induced by action at the level of the DNA-damage pathways and checkpoints, in particular at the ATR-dependent checkpoint, which prevents the initiation of DNA replication in response to damage of the single-stranded type caused by chemical agents such as etoposide.

Cdc7 and Dbf4 are overexpressed in human tumour cell lines and in many tumour samples (lung, breast, thyroid, colon-rectum, oesophagus, uterus, testicle, liver (Hess et al., 1998 and internal data)) in comparison with the corresponding normal tissues.

Experiments in suppressing Cdc7 expression using RNA interference (RNAi) technology show that inhibition of Cdc7 expression induces arrest of the cell cycle and prevents cellular proliferation of the human tumour cell lines HeLa and HCT116, but has a limited effect on normal cells (normal human skin fibroblasts). This is reflected in a prolonged stoppage in G1 that induces apoptosis in cells lacking p53 (>50% of tumours) but is reversible in normal cells [A. Montagnoli et al., CANCER RESEARCH 64, 7110-7116, Oct. 1, 2004].

The inhibitors of Cdc7 kinase activity can constitute a novel category of targeted cytotoxic therapy as well as of inhibitors of DNA replication. Such inhibitors would inhibit replication before the replication forks are established, thus blocking replication without damaging the DNA.

The present application thus relates in particular to novel inhibitors of protein kinase Cdc7 that can be used notably for the treatment of abnormal cellular proliferation and more particularly in oncology.

The present invention thus relates to the products of formula (I):

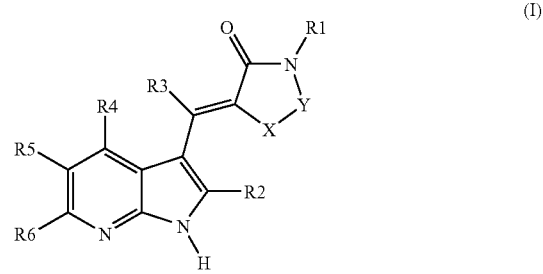

in which:
X—Y represents NH—C(S), N=C—NR7R8, N=C—SR, N=C—R or N=C—OR;
R1 represents a hydrogen atom, a cycloalkyl radical or an alkyl, heterocycloalkyl, aryl or heteroaryl radical, all these radicals being optionally substituted;
R, which may be identical to or different from R1, is selected from the values of R1;
R2 represents a hydrogen atom, a halogen atom or an alkyl radical;
R3 represents a hydrogen atom, a halogen atom, a hydroxyl radical or an alkyl or alkoxy radical;
R4 represents a hydrogen atom, a halogen atom or a cyano, CF3 or alkyl radical;
R5 represents a hydrogen atom, a halogen atom, a hydroxyl, cyano, NR7R8, CONR7R8, NR11COR12 radical, or a cycloalkyl, alkyl, alkoxy, heterocycloalkyl, aryl or heteroaryl radical, all these last-mentioned radicals being optionally substituted;
R6 represents a hydrogen atom, a halogen atom or an NR7R8, alkyl or alkoxy radical;
R7 and R8 are such that:
either R7 and R8, which may be identical or different, are such that one of R7 and R8 represents a hydrogen atom or an alkyl radical, optionally substituted; and the other one of R7 and R8 represents a hydrogen atom or a cycloalkyl, alkyl, heterocycloalkyl, heteroaryl or aryl radical, all these radicals being optionally substituted;
or R7 and R8 form, together with the nitrogen atom to which they are attached, a cyclic radical formed from 3 to 7 ring members optionally containing one or more other heteroatoms selected from O, S or N, N being optionally substituted with R11, said cyclic radical itself being optionally substituted;
all the alkyl, alkoxy, cycloalkyl, heterocycloalkyl, heteroaryl and aryl radicals, as well as the cyclic radical that R7 and R8 can form together with the nitrogen atom to which they are attached, indicated as optionally substituted, thus being optionally substituted with one or more radicals, which may be identical or different, selected from the halogen atoms and the hydroxyl, cyano, nitro, CF3, NR9R10, NHCOR11, NHCO2R11, NHCONR9R10, NHSO2R13, COOH, COOalk, CONR9R10, SO2NR9R10, alkoxy, alkylthio, haloalkoxy, haloalkylthio, alkyl, fluoroalkyl, hydroxyalkyl, cycloalkyl, heterocycloalkyl, heteroaryl and phenyl radicals, these last-mentioned heteroaryl, aryl and phenyl radicals themselves being optionally substituted with one or more radicals, which may be identical or different, selected from the halogen atoms and the hydroxyl, NH2, NH(alk), N(alk)2, alkyl, hydroxyalkyl and alkoxy radicals;
R9 and R10 are such that:
either R9 and R10, which may be identical or different, are such that one of R9 and R10 represents a hydrogen atom or an alkyl radical optionally substituted with one or more radicals, which may be identical or different, selected from the halogen atoms and the hydroxyl and alkoxy radicals; and the other one of R9 and R10 represents a hydrogen atom or a cycloalkyl, alkyl, heterocycloalkyl, heteroaryl or aryl radical, all these radicals themselves being optionally substituted with one or more radicals, which may be identical or different, selected from the halogen atoms and the hydroxyl, NH2, NH(alk), N(alk)2, alkyl, hydroxyalkyl and alkoxy radicals;
or R9 and R10 form, together with the nitrogen atom to which they are attached, a cyclic radical formed from 3 to 7 ring members optionally containing one or more other heteroatoms selected from O, S or N, N being optionally substituted with R12, said cyclic radical itself being optionally substituted with one or more radicals, which may be identical or different, selected from the halogen atoms and the hydroxyl, NH2, NH(alk), N(alk)2, alkyl, hydroxyalkyl and alkoxy radicals;
R11 and R12, which may be identical or different, represent a hydrogen atom or an alkyl or phenyl radical, optionally substituted with one or more radicals, which may be identical or different, selected from the halogen atoms and the hydroxyl and alkoxy radicals, the phenyl radical itself being optionally substituted with one or more alkyl radicals;
R13 represents an alkyl or phenyl radical, optionally substituted with one or more radicals, which may be identical or different, selected from the halogen atoms and the hydroxyl and alkoxy radicals, the phenyl radical itself being optionally substituted with one or more alkyl radicals;
all the above alkyl (alk) and alkoxy radicals being linear or branched and containing at most 12 carbon atoms;
said products of formula (I) being in all possible tautomeric and isomeric forms (racemates, enantiomers and diastereoisomers), as well as salts of addition of said products of formula (I) with organic and inorganic acids or with organic and inorganic bases.

Among the products of formula (I) as defined above, we may exclude the products of formula (I) in which all the following conditions are fulfilled:
R2 represents hydrogen;
R3 represents hydrogen or alkyl;
X—Y represents N=C—NR7R8, N=C—SR or N=CR in which X represents N and Y represents =C—NR7R8, =C—SR or =CR and R represents aryl or heteroaryl;
R1 represents H or alk;
and R4, R5 and R6 are such that two of them represent H and the other represents hydrogen, NH2 or NHalk.

The present invention thus notably relates to the products of formula (I) as defined above in which:
R1 represents a hydrogen atom, or an alkyl radical, all these radicals being optionally substituted as stated above or hereunder;
and R5 represents a halogen atom, a hydroxyl, cyano, NR7R8, CF3 radical or a cycloalkyl, alkyl, alkoxy, heterocycloalkyl, aryl or heteroaryl radical,
all these last-mentioned radicals being optionally substituted as stated above or hereunder;
the other substituent radicals R2, R3, R4, R6 and X—Y having the values as defined above or hereunder,
said products of formula (I) being in all possible tautomeric and isomeric forms (racemates, enantiomers and diastereoisomers), as well as salts of addition of said products of formula (I) with organic and inorganic acids or with organic and inorganic bases.

The present invention thus notably relates to the products of formula (I) as defined above in which:
R2 represents a hydrogen atom;
and R5 represents a halogen atom, a hydroxyl, cyano, NR7R8, CF3 radical or a cycloalkyl, alkyl, alkoxy, heterocycloalkyl, aryl or heteroaryl radical, all these last-mentioned radicals being optionally substituted as stated above or hereunder;
the other substituent radicals R1, R3, R4, R6 and X—Y having the values as defined above or hereunder,
said products of formula (I) being in all possible tautomeric and isomeric forms (racemates, enantiomers and diastereoisomers), as well as salts of addition of said products of formula (I) with organic and inorganic acids or with organic and inorganic bases.

The present invention thus notably relates to the products of formula (I) as defined above in which:

R3 represents a hydrogen atom;

and R5 represents a halogen atom, a hydroxyl, cyano, CONR7R8 radical or a cycloalkyl, alkyl, alkoxy, heterocycloalkyl, aryl or heteroaryl radical, all these last-mentioned radicals being optionally substituted as stated above or hereunder;

the other radicals R2, R3, R4, R6 and X—Y having the values as defined above or hereunder, said products of formula (I) being in all possible tautomeric and isomeric forms (racemates, enantiomers and diastereoisomers), as well as salts of addition of said products of formula (I) with organic and inorganic acids or with organic and inorganic bases.

The present invention thus notably relates to the products of formula (I) as defined above in which:

X—Y represents NH—C(S), N═C—NR7R8 or N═C—R;

R1 represents a hydrogen atom, a cycloalkyl radical or an alkyl, heterocycloalkyl, aryl or heteroaryl radical, all these radicals being optionally substituted as stated above or hereunder;

R, which may be identical to or different from R1, is selected from the values of R1 as defined above or hereunder with the exception of aryl and heteroaryl;

the other substituents R2, R3, R4, R5 and R6 having the values as defined above or hereunder;

said products of formula (I) being in all possible tautomeric and isomeric forms (racemates, enantiomers and diastereoisomers), as well as salts of addition of said products of formula (I) with organic and inorganic acids or with organic and inorganic bases.

The present invention notably relates to the products of formula (I) as defined above in which X—Y represents NH—C(S), N═C—NR7R8, N═C—SR, N═C—R or N═C—OR;

R1 represents a hydrogen atom, a cycloalkyl radical or an alkyl, heterocycloalkyl, phenyl or heteroaryl radical, these last-mentioned radicals being optionally substituted;

R, which may be identical to or different from R1, is selected from the values of R1;

R2 represents a hydrogen atom, a halogen atom or an alkyl radical;

R3 represents a hydrogen atom, a halogen atom, a hydroxyl radical or an alkyl or alkoxy radical;

R4 represents a hydrogen atom, a halogen atom or a cyano, CF3 or alkyl radical;

R5 represents a hydrogen atom, a halogen atom, a hydroxyl, cyano, NR7R8, CONR7R8, NR11COR12 radical or a cycloalkyl, alkyl, alkoxy, heterocycloalkyl, phenyl or heteroaryl radical, all these last-mentioned radicals being optionally substituted;

R6 represents a hydrogen atom, a halogen atom or an NR7R8, alkyl or alkoxy radical;

R7 and R8 are such that:

either R7 and R8, which may be identical or different, are such that one of R7 and R8 represents a hydrogen atom or an alkyl radical optionally substituted with one or more radicals, which may be identical or different, selected from the halogen atoms and the hydroxyl and alkoxy radicals;

and the other one of R7 and R8 represents a hydrogen atom or a cycloalkyl, alkyl, heterocycloalkyl, heteroaryl or phenyl radical, all these radicals being optionally substituted;

or R7 and R8 form, together with the nitrogen atom to which they are attached, a cyclic radical formed from 3 to 7 ring members optionally containing one or more other heteroatoms selected from O, S or N, N being optionally substituted with R11, said cyclic radical itself being optionally substituted;

all the alkyl, alkoxy, cycloalkyl, heterocycloalkyl, heteroaryl and aryl radicals, as well as the cyclic radical that R7 and R8 can form together with the nitrogen atom to which they are attached, indicated as optionally substituted, thus being optionally substituted with one or more radicals, which may be identical or different, selected from the halogen atoms and the hydroxyl, cyano, nitro, CF3, NR9R10, NHCOR11, NHSO2R13, COOH, COOalk, CONR9R10, SO2NR9R10, alkoxy, haloalkoxy, alkyl, fluoroalkyl, hydroxyalkyl, cycloalkyl, heterocycloalkyl, heteroaryl and phenyl radicals, these last-mentioned heteroaryl and phenyl radicals themselves being optionally substituted with one or more radicals, which may be identical or different, selected from the halogen atoms and the hydroxyl, NH2, NH(alk), N(alk)2, alkyl, hydroxyalkyl and alkoxy radicals;

R9 and R10 are such that:

either R9 and R10, which may be identical or different, are such that one of R9 and R10 represents a hydrogen atom or an alkyl radical and the other one of R9 and R10 represents a hydrogen atom or an alkyl, phenyl or phenylalkyl radical, themselves optionally substituted with one or more radicals, which may be identical or different, selected from the halogen atoms and the hydroxyl, NH2, NH(alk), N(alk)2, alkyl, hydroxyalkyl and alkoxy radicals;

or R9 and R10 form, together with the nitrogen atom to which they are attached, a pyrrolidinyl, morpholine, piperidyl, azepinyl or piperazinyl radical optionally substituted with an alkyl or phenyl radical, itself optionally substituted with one or more radicals, which may be identical or different, selected from the halogen atoms and the alkyl, hydroxyl, NH2, NH(alk), N(alk)2, alkyl, hydroxyalkyl and alkoxy radicals;

R11 and R12, which may be identical or different, represent a hydrogen atom or an alkyl or phenyl radical;

R13 represents an alkyl or phenyl radical;

all the above alkyl (alk) and alkoxy radicals being linear or branched and containing at most 6 carbon atoms;

said products of formula (I) being in all possible tautomeric and isomeric forms (racemates, enantiomers and diastereoisomers), as well as salts of addition of said products of formula (I) with organic and inorganic acids or with organic and inorganic bases.

When R9 and R10 form, together with the nitrogen atom to which they are attached, a cyclic radical, notably R9 and R10 form, together with the nitrogen atom to which they are attached, a pyrrolidinyl, morpholine, piperidyl or piperazinyl radical optionally substituted with an alkyl radical.

The present invention relates in particular to the products of formula (I) as defined above in which:

X—Y represents NH—C(S), N═C—NR7R8, N═C—SR, N═C—R or N═C—OR;

R1 represents a hydrogen atom or an alkyl or phenyl radical, optionally substituted;

R represents a hydrogen atom; a cycloalkyl, an alkyl, heterocycloalkyl, phenyl, or heteroaryl radical, all these radicals being optionally substituted;

R2 represents a hydrogen atom, a halogen atom or an alkyl radical;

R3 represents a hydrogen atom, a halogen atom, a hydroxyl radical or an alkyl radical;

R4 represents a hydrogen atom, a halogen atom or an alkyl radical;

R5 represents a hydrogen atom; a halogen atom; a hydroxyl, cyano, NR7R8, alkyl, alkoxy, heterocycloalkyl, phenyl, or heteroaryl radical, all these last-mentioned radicals as well as the phenyl residue in NHphenyl and NH(phenylalk) being optionally substituted;

R6 represents a hydrogen atom, a halogen atom, or an NH2, NHalk, N(alk)2, alkyl or alkoxy radical;

R7 and R8 are such that: either R7 and R8, which may be identical or different, are such that one of R7 and R8 represents a hydrogen atom or an alkyl radical; and the other one of R7 and R8 represents a hydrogen atom, or an alkyl or cycloalkyl radical, optionally substituted; or R7 and R8 form, together with the nitrogen atom to which they are attached, a cyclic radical selected from the azetidyl, piperidyl, azepanyl, morpholinyl, thiomorpholinyl, pyrrolidinyl, imidazolidinyl, piperazinyl radicals optionally substituted on the second nitrogen atom with an alkyl or phenyl radical, themselves optionally substituted; and homopiperazinyl, all these cyclic radicals being optionally substituted;

all the alkyl, alkoxy, heterocycloalkyl, heteroaryl and phenyl radicals, as well as the cyclic radical that R7 and R8 can form together with the nitrogen atom to which they are attached being optionally substituted with one or more radicals, which may be identical or different, selected from the halogen atoms and the hydroxyl, NH2, NH(alk), N(alk)2, NHphenyl, NH(phenylalk), alkyl, CF3, alkoxy, OCF3, cycloalkyl, heterocycloalkyl, heteroaryl and phenyl radicals; these last-mentioned heteroaryl and phenyl radicals, as well as the phenyl residue in the NHphenyl and NH(phenylalk) radicals, themselves being optionally substituted with one or more radicals, which may be identical or different, selected from the halogen atoms and the hydroxyl, NH2, NHAlk, N(Alk)2, alkyl, hydroxyalkyl and alkoxy radicals;

all the above alkyl (alk) and alkoxy radicals being linear or branched and containing at most 6 carbon atoms;

said products of formula (I) being in all possible tautomeric and isomeric forms (racemates, enantiomers and diastereoisomers), as well as salts of addition of said products of formula (I) with organic and inorganic acids or with organic and inorganic bases.

In the products of formula (I) and hereinafter:

the term alkyl radical or alk denotes the linear and branched radicals containing at most 12 carbon atoms, such as for example the methyl, ethyl, propyl, isopropyl, butyl, isobutyl, sec-butyl, tert-butyl, pentyl, isopentyl, hexyl, isohexyl and also heptyl, octyl, nonyl and decyl radicals as well as their linear or branched positional isomers; the term notably represents the linear and branched radicals containing at most 6 carbon atoms selected from those defined above and also the linear and branched radicals containing at most 4 carbon atoms selected from those defined above;

the term alkylthio radical denotes the —S-alkyl radicals in which the alkyl radical has the meaning stated above;

the terms haloalkyl and haloalkylthio represent the alkyl and alkylthio radicals as defined above substituted with one or more halogen atoms;

the term hydroxyalkyl radical denotes the alkyl radicals stated above substituted with at least one hydroxyl radical;

the term alkoxy radical denotes the linear and branched radicals containing at most 12 carbon atoms, such as for example the methoxy, ethoxy, propoxy, isopropoxy, linear, secondary or tertiary butoxy; pentoxy or hexoxy radicals as well as their linear or branched positional isomers; the term notably represents the linear and branched radicals containing at most 6 carbon atoms selected from those defined above and also the linear and branched radicals containing at most 4 carbon atoms selected from those defined above;

the terms NH(alk) and N(alk)2 denote amino radicals substituted respectively with one or two alkyl radicals, said alkyl radicals being linear or branched and selected from the alkyl radicals as defined above, preferably containing at most 6 carbon atoms;

in the groups above and hereunder, NR7R8, CONR7R8, NR11COR12, NR9R10, NHCOR11, NHCO2R11, NHCONR9R10, NHSO2R13, CONR9R10 and SO2NR9R10, the radicals R7, R8, R9, R10, R11, R12 and R13 can assume all the values stated for these radicals;

the term halogen atom denotes the chlorine, bromine, iodine or fluorine atoms and preferably the chlorine, bromine or fluorine atom;

the term cycloalkyl radical denotes a saturated carbocyclic radical containing 3 to 10 carbon atoms and thus notably denotes the cyclopropyl, cyclobutyl, cyclopentyl and cyclohexyl radicals and quite particularly the cyclopentyl and cyclohexyl radicals;

the term heterocycloalkyl radical thus denotes a monocyclic or bicyclic carbocyclic radical interrupted by one or more heteroatoms, which may be identical or different, selected from the oxygen, nitrogen or sulphur atoms: we may mention for example the radicals morpholinyl, thiomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, hexahydropyran, oxodihydropyridazinyl radicals, all these radicals being optionally substituted;

the terms aryl and heteroaryl denote unsaturated or partially unsaturated radicals, respectively carbocyclic and heterocyclic, monocyclic or bicyclic, containing at most 12 ring members, and can optionally contain a —C(O) group, the heterocyclic radicals containing one or more heteroatoms which may be identical or different selected from O, N, or S, with N, if necessary, optionally substituted;

the term aryl radical thus denotes monocyclic or bicyclic radicals containing 4 to 12 ring members such as for example the phenyl, naphthyl, biphenyl, indenyl, fluorenyl and anthracenyl radicals, more particularly the phenyl and naphthyl radicals and even more particularly the phenyl radical. It may be noted that a carbocyclic radical containing a —C(O) group is for example the tetralone radical;

the term heteroaryl radical thus denotes monocyclic or bicyclic radicals containing 4 to 12 ring members: monocyclic heteroaryl radicals such as for example the thienyl radicals such as 2-thienyl and 3-thienyl, furyl such as 2-furyl, 3-furyl, pyranyl, pyrrolyl, pyrrolinyl, pyrazolinyl, imidazolyl, pyrazolyl, pyridyl such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, thiatriazolyl, oxadiazolyl, isoxazolyl such as 3- or 4-isoxazolyl, furazanyl, tetrazolyl whether free or salified, all these radicals being optionally substituted, among which more particularly the thienyl radicals such as 2-thienyl and 3-thienyl, furyl such as 2-furyl, pyrrolyl, pyrrolinyl, pyrazolinyl, imidazolyl, pyrazolyl, oxazolyl, isoxazolyl, pyridyl, pyridazinyl, these radicals being optionally substituted; bicyclic heteroaryl radicals such as for example the benzothienyl radicals such as 3-benzothienyl, benzothiazolyl, quinolyl, isoquinolyl, dihydroquinolyl, quinolizinyl, tetrahydroquinolizinyl, quinolone, tetralone, adamentyl, benzofuryl, isobenzofuryl, dihydrobenzofuran, ethylenedioxyphenyl, thianthrenyl, benzopyrrolyl, benzimidazolyl, benzoxazolyl, thionaphthyl, indolyl, azaindolyl, indazolyl, purinyl, thienopyrazolyl, tetrahydroindazolyl, tetrahydrocyclopentapyrazolyl, dihydrofuropyrazolyl, tetrahydropyrrolopyrazolyl, oxotetrahydropyrrolopyrazolyl, tetrahydropyranopyrazolyl, tetrahydropyridinopyrazolyl or oxodihydropyridinopyrazolyl, all these radicals being optionally substituted.

As examples of heteroaryl radicals, we may mention more particularly the pyrimidinyl, pyridyl, pyrrolyl, azaindolyl, indazolyl or pyrazolyl radicals, optionally substituted with one or more substituents which may be identical or different as stated above.

the term phenylalkyl denotes an alkyl radical as defined above in which the alkyl radical is linear or branched, preferably containing at most 4 carbon atoms and the phenyl radical is optionally substituted with one or more radicals as defined previously or hereunder;

The carboxy radical or radicals of the products of formula (I) can be salified or esterified by the various groups known to a person skilled in the art, among which we may mention, for example:

among the salification compounds, inorganic bases such as, for example, an equivalent of sodium, of potassium, of lithium, of calcium, of magnesium or of ammonium or organic bases such as, for example, methylamine, propylamine, trimethylamine, diethylamine, triethylamine, N,N-dimethylethanolamine, tris(hydroxymethyl)aminomethane, ethanolamine, pyridine, pico-line, dicyclohexylamine, morpholine, benzylamine, procaine, lysine, arginine, histidine, N-methylglucamine, among the esterification compounds, the alkyl radicals for forming alkoxycarbonyl groups such as, for example, methoxycarbonyl, ethoxycarbonyl, tert-butoxycarbonyl or benzyloxycarbonyl, and said alkyl radicals can be substituted with radicals selected for example from the halogen atoms, the hydroxyl, alkoxy, acyl, acyloxy, alkylthio, amino or aryl radicals such as, for example, in the chloromethyl, hydroxypropyl, methoxymethyl, propionyloxymethyl, methylthiomethyl, dimethylaminoethyl, benzyl or phenethyl groups.

The salts of addition of the products of formula (I) with organic or inorganic acids can be, for example, the salts formed with hydrochloric, hydrobromic, hydriodic, nitric, sulphuric, phosphoric, propionic, acetic, trifluoroacetic, formic, benzoic, maleic, fumaric, succinic, tartaric, citric, oxalic, glyoxylic, aspartic, ascorbic acids, the alkylmonosulphonic acids such as for example methanesulphonic acid, ethanesulphonic acid, propanesulphonic acid, alkyldisulphonic acids such as for example methanedisulphonic acid, alpha, beta-ethanedisulphonic acid, arylmonosulphonic acids such as benzenesulphonic acid and the aryldisulphonic acids.

It may be recalled that stereoisomerism can be defined broadly as the isomerism of compounds having the same structural formulae, but in which the various groups are arranged differently in space, such as notably in monosubstituted cyclo-hexanes in which the substituent can be in the axial or equatorial position, and the various possible rotational conformations of the derivatives of ethane. However, there is another type of stereoisomerism, due to the different spatial arrangements of substituents that are fixed either on double bonds, or on rings, which is often called geometric isomerism or cis-trans isomerism. The term stereoisomers is used in the present application in its broadest sense and therefore applies to all of the compounds stated above.

The present invention thus relates to the products of formula (I) as defined above in which X—Y represents NH—C(S), N═C—NR7R8, N═C—SR, N═C—R or N═C—OR;

R1 represents a hydrogen atom or an alkyl or phenyl radical, optionally substituted;

R, which may be identical to or different from R1, is selected from the values of R1;

R2 represents a hydrogen atom, a halogen atom or an alkyl radical;

R3 represents a hydrogen atom, a halogen atom, a hydroxyl radical or an alkyl radical;

R4 represents a hydrogen atom, a halogen atom or an alkyl radical;

R5 represents a hydrogen atom, a halogen atom, a hydroxyl radical, an NH2, NHalk, N(alk)2, NR7R8, NHphenyl, NH(phenylalk) radical or an alkyl, heterocycloalkyl, alkoxy, phenyl or heteroaryl radical, these last-mentioned radicals as well as the phenyl residue in NHphenyl and NH(phenylalk) being optionally substituted;

R6 represents a hydrogen atom, a halogen atom, or an NH2, NHalk, N(alk)2, alkyl or alkoxy radical;

R7 and R8 are such that: either R7 and R8, which may be identical or different, are such that one of R7 and R8 represents a hydrogen atom or an alkyl radical;

and the other one of R7 and R8 represents a hydrogen atom, or an alkyl or cycloalkyl radical, optionally substituted;

or R7 and R8 form, together with the nitrogen atom to which they are attached, a cyclic radical containing 4 to 6 ring members selected from azetidyl; piperidyl; morpholinyl; thiomorpholinyl; pyrrolidinyl; imidazolidinyl; piperazinyl; and homopiperazinyl, these radicals being optionally substituted; all the alkyl, alkoxy, heteroaryl and phenyl radicals, as well as the cyclic radical that R7 and R8 can form together with the nitrogen atom to which they are attached, indicated as optionally substituted, thus being optionally substituted with one or more radicals, which may be identical or different, selected from the halogen atoms and the hydroxyl, NH2, NH(alk), N(alk)2, NHphenyl, NH(phenylalk), alkyl, CF3, alkoxy, OCF3, cycloalkyl, heterocycloalkyl, heteroaryl and phenyl radicals; these last-mentioned heteroaryl and phenyl radicals, as well as the phenyl residue in the NHphenyl and NH(phenylalk) radicals, themselves being optionally substituted with one or more radicals, which may be identical or different, selected from the halogen atoms and the hydroxyl, NH2, NHAlk, N(Alk)2, alkyl, hydroxyalkyl and alkoxy radicals;

all the above alkyl (alk) and alkoxy radicals being linear or branched and containing at most 6 carbon atoms;

said products of formula (I) being in all possible tautomeric and isomeric forms (racemates, enantiomers and diastereoisomers), as well as salts of addition of said products of formula (I) with organic and inorganic acids or with organic and inorganic bases.

In the products of formula (I) according to the present invention, the substituents X—Y, R1, R2, R3, R4, R5 and R6 can notably have, independent of one another, the following values i) to vii):

i) notably X—Y represents NH—C(S), N═C—NR7R8 or N═C—R with NR7R8 and R as defined above or hereunder;

ii) notably R1 represents a hydrogen atom or an alkyl or phenyl radical, optionally substituted with N(alk)2, morpholinyl or pyrrolidinyl, alkoxy or phenyl;
iii) notably R2 represents a hydrogen atom, or an alkyl radical;
iv) notably R3 represents a hydrogen atom;
v) notably R4 represents a hydrogen atom or a halogen atom;
vi) notably R5 represents a hydrogen atom; a halogen atom; a hydroxyl, cyano, NH2, NHalk, N(alk)2, NHphenyl, NH(phenylalk), CF3 radical; alkyl radical optionally substituted with phenyl; alkoxy; heterocycloalkyl such as for example morpholinyl; phenyl optionally substituted with a heterocyclic radical such as for example piperazinyl; or heteroaryl such as for example thienyl, these last-mentioned radicals as well as phenyl and the phenyl residue in NHphenyl and NH(phenylalk), being optionally substituted;
vii) notably R6 represents a hydrogen atom or a halogen atom;
all the alkyl, alkoxy, heterocycloalkyl, heteroaryl and phenyl radicals being optionally substituted with one or more radicals which may be identical or different as stated above or hereunder,
it being understood that for each of the values i) to vii), the other substituents of said products of formula (I) can have any one of the values defined above or hereunder,
said products of formula (I) being in all possible tautomeric and isomeric forms (racemates, enantiomers and diastereoisomers), as well as salts of addition of said products of formula (I) with organic and inorganic acids or with organic and inorganic bases.

In the products of formula (I) according to the present invention, in the radical X—Y, R notably represents a hydrogen atom; a cycloalkyl radical; alkyl radical; heterocycloalkyl radical such as notably morpholino, tetrahydropyran; phenyl; or heteroaryl such as notably pyridine, quinoline, quinolizinyl, tetrahydroquinolizinyl, indolyl, thienyl, furanyl, pyrrolyl and pyrazolyl; all these radicals being optionally substituted as stated above or hereunder.

More precisely R represents a hydrogen atom; or a cycloalkyl radical such as notably cyclohexyl; an alkyl radical optionally substituted notably with cycloalkyl such as for example cyclopropyl, cyclobutyl, cyclopentyl, with phenyl or with heteroaryl such as notably pyridine, all these radicals being optionally substituted as stated above or hereunder; heterocycloalkyl such as notably morpholino or tetrahydropyran; phenyl or heteroaryl such as notably pyridine, quinolyl, thienyl, furanyl, pyrrolyl and pyrazolyl optionally substituted as stated above or hereunder.

When the products of formula (I) according to the present invention bear a radical NR7R8, notably R7 and R8 are such that either R7 and R8, which may be identical or different, are such that one of R7 and R8 represents a hydrogen atom or an alkyl radical; and the other one of R7 and R8 represents a hydrogen atom, or an alkyl radical optionally substituted with cycloalkyl; or R7 and R8 form, together with the nitrogen atom to which they are attached, a piperidyl; azepinyl; morpholinyl; pyrrolidinyl; piperazinyl radical optionally substituted on its second nitrogen atom with alkyl or phenyl; these radicals being optionally substituted as stated above or hereunder.

The present invention thus relates to the products of formula (I) as defined above in which
X—Y, R2, R3, R4 and R6 have the meanings stated above,
R1 represents a hydrogen atom or an alkyl radical, optionally substituted;

R5 represents a hydrogen atom, a halogen atom, a hydroxyl, CF3, NH2, NHalk, N(alk)2 radical or an alkyl, alkoxy or phenyl radical, optionally substituted;
the alkyl radical that can be represented by R1 or the alkyl, alkoxy or phenyl radical that can be represented by R5, being optionally substituted with one or more radicals, which may be identical or different, selected from the halogen atoms and the hydroxyl, NHalk, N(alk)2, alkoxy, cycloalkyl, heterocycloalkyl, heteroaryl and phenyl radicals, these last-mentioned heteroaryl and phenyl radicals being optionally substituted with one or more radicals, which may be identical or different, selected from the halogen atoms and the hydroxyl, NH2, NHAlk, N(Alk)2, alkyl, hydroxyalkyl and alkoxy radicals;
R7 and R8 are such that:
either R7 and R8, which may be identical or different, are such that one of R7 and R8 represents a hydrogen atom or an alkyl radical,
and the other one of R7 and R8 represents a hydrogen atom, an alkyl radical optionally substituted with one or more radicals, which may be identical or different, selected from the halogen atoms, the hydroxyl, NH2, NHalk, N(alk)2, NH(phenyl), NH(phenylalk), alkoxy, OCF3, cycloalkyl radicals, and the pyrrolidinyl, piperazinyl, piperidyl, morpholinyl and phenyl radicals, all these last-mentioned cyclic radicals, as well as the phenyl residue in the phenylalkyl radical, themselves being optionally substituted with one or more radicals, which may be identical or different, selected from the halogen atoms and the hydroxyl, NH2, NHAlk, N(alk)2, alkoxy, alkyl and hydroxyalkyl radicals;
or R7 and R8 form, together with the nitrogen atom to which they are attached, a radical preferably selected from the piperidyl, morpholinyl radicals, and the pyrrolidinyl, piperazinyl and homopiperazinyl radicals optionally substituted with one or more radicals, which may be identical or different, selected from the alkyl and phenyl radicals, themselves optionally substituted with one or more radicals selected from the halogen atoms and the hydroxyl, NH2, NHAlk, N(Alk)2, alkoxy and cycloalkyl radicals;
all the above alkyl (alk) and alkoxy radicals being linear or branched and containing at most 6 carbon atoms;
said products of formula (I) being in all possible tautomeric and isomeric forms (racemates, enantiomers and diastereoisomers), as well as salts of addition of said products of formula (I) with organic and inorganic acids or with organic and inorganic bases.

The present invention thus relates to the products of formula (I) as defined above in which
X—Y represents NH—C(S), N=C—NR7R8 or N=C—R,
R7, R8 and R being selected from all the values defined above for R7, R8 and R and the other substituents R1, R2, R3, R4, R5 and R6 of said products of formula (I) being selected from all the values defined above respectively for R1, R2, R3, R4, R5 and R6,
said products of formula (I) being in all possible tautomeric and isomeric forms (racemates, enantiomers and diastereoisomers), as well as salts of addition of said products of formula (I) with organic and inorganic acids or with organic and inorganic bases.

The present invention thus relates to the products of formula (I) as defined above in which
X—Y represents NH—C(S), N=C—NR7R8 or N=C—R;
R1 represents a hydrogen atom or an alkyl radical optionally substituted with one or more radicals, which may be identical or different, selected from the halogen atoms and the N(alk)2 and alkoxy radicals;

R, which may be identical to or different from R1, is selected from the values of R1;

R2 represents a hydrogen atom, a halogen atom or an alkyl radical;

R3 represents a hydrogen atom or an alkyl radical;

R4 represents a hydrogen atom or a halogen atom,

R5 represents a hydrogen atom, a halogen atom or a hydroxyl, NH2, NHalk, N(alk)2, alkyl, alkoxy or phenyl radical, the alkyl radical being optionally substituted with an alkoxy, N(alk)2 or heterocycloalkyl radical and the phenyl radical being optionally substituted with one or more radicals, which may be identical or different, selected from the halogen atoms and the hydroxyl, NH2, NHalk, N(alk)2, alkyl and alkoxy radicals;

R6 represents a hydrogen atom, a halogen atom or an alkyl radical;

and R7 and R8 are such that:

either R7 and R8, which may be identical or different, are such that one of R7 and R8 represents a hydrogen atom or an alkyl radical, and the other one of R7 and R8 represents an alkyl radical optionally substituted with a cycloalkyl radical;

or R7 and R8 form, together with the nitrogen atom to which they are attached, a pyrrolidinyl, morpholine, piperidyl or piperazinyl radical optionally substituted with an alkyl radical;

said products of formula (I) being in all possible tautomeric and isomeric forms (racemates, enantiomers and diastereoisomers), as well as salts of addition of said products of formula (I) with organic and inorganic acids or with organic and inorganic bases.

In the products of formula (I) as defined above, we may note quite particularly the products for which R3 represents a hydrogen atom, the other substituents R1, R2, R4, R5, R6 and X—Y of said products of formula (I) being selected from any one of the values defined above, said products of formula (I) being in all possible tautomeric and isomeric forms (racemates, enantiomers and diastereoisomers), as well as salts of addition of said products of formula (I) with organic and inorganic acids or with organic and inorganic bases.

The present invention thus relates to the products of formula (I) as defined above in which X—Y represents NH—C(S), N═C—NR7R8 or N═C—R;

R1 and R2, which may be identical or different, represent a hydrogen atom or an alkyl radical;

R3 represents a hydrogen atom;

R4, R5 and R6, which may be identical or different, represent a hydrogen atom or a halogen atom;

R7 and R8 represent the values defined in any one of the above claims;

all the above alkyl (alk) radicals being linear or branched and containing at most 4 carbon atoms; said products of formula (I) being in all possible tautomeric and isomeric forms (racemates, enantiomers and diastereoisomers), as well as salts of addition of said products of formula (I) with organic and inorganic acids or with organic and inorganic bases.

The present invention relates notably to the products of formula (I) as defined above in which X—Y represents N═C—NR7R8 or N═C—R, R7, R8 and R being selected from all the values defined above for R7, R8 and R and the other substituents R1, R2, R3, R4, R5 and R6 of said products of formula (I) being selected from all the values defined above respectively for R1, R2, R3, R4, R5 and R6, said products of formula (I) being in all possible tautomeric and isomeric forms (racemates, enantiomers and diastereoisomers), as well as salts of addition of said products of formula (I) with organic and inorganic acids or with organic and inorganic bases.

The present invention relates notably to the products of formula (I) as defined above in which X—Y represents N═C—NR7R8, R7 and R8 being selected from all the values defined above for R7 and R8 and the other substituents R1, R2, R3, R4, R5 and R6 of said products of formula (I) being selected from all the values defined above respectively for R1, R2, R3, R4, R5 and R6, said products of formula (I) being in all possible tautomeric and isomeric forms (racemates, enantiomers and diastereoisomers), as well as salts of addition of said products of formula (I) with organic and inorganic acids or with organic and inorganic bases.

The present invention relates notably to the products of formula (I) as defined above in which X—Y represents N═C—R, R being selected from all the values defined above for R7, R8 and R and the other substituents R1, R2, R3, R4, R5 and R6 of said products of formula (I) being selected from all the values defined above respectively for R1, R2, R3, R4, R5 and R6, said products of formula (I) being in all possible tautomeric and isomeric forms (racemates, enantiomers and diastereoisomers), as well as salts of addition of said products of formula (I) with organic and inorganic acids or with organic and inorganic bases.

The present invention relates notably to the products of formula (I) as defined above in which X—Y represents N═C—OR, R being selected from all the values defined above for R7, R8 and R and the other substituents R1, R2, R3, R4, R5 and R6 of said products of formula (I) being selected from all the values defined above respectively for R1, R2, R3, R4, R5 and R6, said products of formula (I) being in all possible tautomeric and isomeric forms (racemates, enantiomers and diastereoisomers), as well as salts of addition of said products of formula (I) with organic and inorganic acids or with organic and inorganic bases.

The present invention relates more particularly to the products of formula (I) as defined above, having the following names:

(5Z)-5-(1H-pyrrolo[2,3-b]pyridin-3-ylmethylene)-2-thioxoimidazolidin-4-one (5Z)-5-[(5-chloro-1H-pyrrolo[2,3-b]pyridin-3-yl)methylene]-2-thioxoimidazolidin-4-one (5Z)-2-[(cyclopropylmethyl)amino]-5-(1H-pyrrolo[2,3-b]pyridin-3-ylmethylene)-3,5-dihydro-4H-imidazol-4-one (5Z)-5-[(5-chloro-1H-pyrrolo[2,3-b]pyridin-3-yl)methylene]-2-[(cyclopropylmethyl)amino]-3,5-dihydro-4H-imidazol-4-one (5Z)-5-[(6-chloro-1H-pyrrolo[2,3-b]pyridin-3-yl)methylene]-2-[(cyclopropylmethyl)amino]-3,5-dihydro-4H-imidazol-4-one (5Z)-2-[(cyclopropylmethyl)amino]-3-methyl-5-(1H-pyrrolo[2,3-b]pyridin-3-ylmethylene)-3,5-dihydro-4H-imidazol-4-one (5Z)-2-butyl-5-(1H-pyrrolo[2,3-b]pyridin-3-ylmethylene)-3,5-dihydro-4H-imidazol-4-one (5Z)-2-azepan-1-yl-5-[(5-chloro-1H-pyrrolo[2,3-b]pyridin-3-yl)methylidene]-3,5-dihydro-4H-imidazol-4-one (5Z)-5-[(5-chloro-1H-pyrrolo[2,3-b]pyridin-3-yl)methylidene]-2-piperidin-1-yl-3,5-dihydro-4H-imidazol-4-one (5Z)-5-[(5-chloro-1H-pyrrolo[2,3-b]pyridin-3-yl)methylidene]-2-[methyl(2-methylpropyl)amino]-3,5-dihydro-4H-imidazol-4-one (5Z)-5-[(5-bromo-1H-pyrrolo[2,3-b]pyridin-3-yl)methylidene]-2-[(cyclopropylmethyl)amino]-3,5-dihydro-4H-imidazol-4-one (5Z)-2-[(cyclopropylmethyl)amino]-5-[(5-methoxy-1H-pyrrolo[2,3-b]pyridin-3-yl)methylidene]-3,5-dihydro-4H-imidazol-4-one (5Z)-2-[(cyclopropylmethyl)amino]-5-[(5-fluoro-1H-pyrrolo[2,3-b]pyridin-3-yl)methylidene]-3,5-dihydro-4H-imidazol-4-one (5Z)-2-azepan-1-yl-5-[(5-fluoro-1H-pyrrolo[2,3-b]pyridin-3-yl)methylidene]-3,5-dihydro-4H-imidazol-4-one 3-[(Z)-{2-[(cyclopropylmethyl)amino]-5-oxo-1,5-dihydro-4H-imidazol-4-ylidene}methyl]-1H-pyrrolo[2,3-b]pyridine-5-carbonitrile (5Z)-2-[(cyclopropylmethyl)amino]-5-[(5-phenyl-1H-pyrrolo[2,3-b]pyridin-3-yl)methylidene]-3,5-dihydro-4H-imidazol-4-one (5Z)-2-[(cyclopropylmethyl)amino]-5-{[5-(trifluoromethyl)-1H-pyrrolo[2,3-b]pyridin-3-yl]methylidene}-3,5-dihydro-4H-imidazol-4-one (5Z)-5-[(5-chloro-1H-pyrrolo[2,3-b]pyridin-3-yl)methylidene]-2-(methylsulphanyl)-3,5-dihydro-4H-imidazol-4-one (5Z)-2-butyl-5-[(5-chloro-1H-pyrrolo[2,3-b]pyridin-3-yl)methylidene]-3,5-dihydro-4H-imidazol-4-one (5Z)-2-(3-methylbutyl)-5-(1H-pyrrolo[2,3-b]pyridin-3-ylmethylidene)-3,5-dihydro-4H-imidazol-4-one (5Z)-2-cyclohexyl-5-(1H-pyrrolo[2,3-b]pyridin-3-ylmethylidene)-3,5-dihydro-4H-imidazol-4-one (5Z)-5-[(5-chloro-1H-pyrrolo[2,3-b]pyridin-3-yl)methylidene]-3-methyl-2-(tetrahydro-2H-pyran-4-yl)-3,5-dihydro-4H-imidazol-4-one (5Z)-5-[(5-chloro-1H-pyrrolo[2,3-b]pyridin-3-yl)methylidene]-3-methyl-2-(2-methylpropyl)-3,5-dihydro-4H-imidazol-4-one (5Z)-2-(cyclopropylmethyl)-5-(5-chloro-1H-pyrrolo[2,3-b]pyridin-3-ylmethylidene)-3,5-dihydro-4H-imidazol-4-one (5Z)-2-(1-methylethyl)-5-(5-chloro-1H-pyrrolo[2,3-b]pyridin-3-ylmethylidene)-3,5-dihydro-4H-imidazol-4-one (5Z)-2-[benzyl(methyl)amino]-5-[(5-chloro-1H-pyrrolo[2,3-b]pyridin-3-yl)methylidene]-3,5-dihydro-4H-imidazol-4-one (5Z)-5-[(5-chloro-1H-pyrrolo[2,3-b]pyridin-3-yl)methylidene]-2-[(2-methoxyethyl)(methyl)amino]-3,5-dihydro-4H-imidazol-4-one said products of formula (I) being in all possible isomeric forms: racemates, enantiomers and diastereoisomers, as well as salts of addition of said products of formula (I) with organic and inorganic acids or with organic and inorganic bases.

The products of formula (I) as defined above can be prepared by the general methods known by a person skilled in the art and more particularly can be prepared using the methods of synthesis described in the following Schemes 1 to 7.

The present invention thus also relates to methods of preparation of the products of formula (I), and notably the methods defined hereunder in Schemes 1 to 7 which are used for the preparation of compounds described in tables presented below.

The tables and schemes that follow are related as follows:
Tables 1, 2 and 4 describe products of formula (I) that can be prepared according to Scheme 1
Table 6 describes products of formula (I) that can be prepared according to Scheme 2
Table 3 describes a product of formula (I) that can be prepared according to Scheme 3
Table 5 describes products of formula (I) that can be prepared according to Schemes 3 and 5
Table 7 describes products of formula (I) that can be prepared according to Scheme 6 or 7
Table 8 describes products of formula (I) that can be prepared according to Schemes 1 to 7

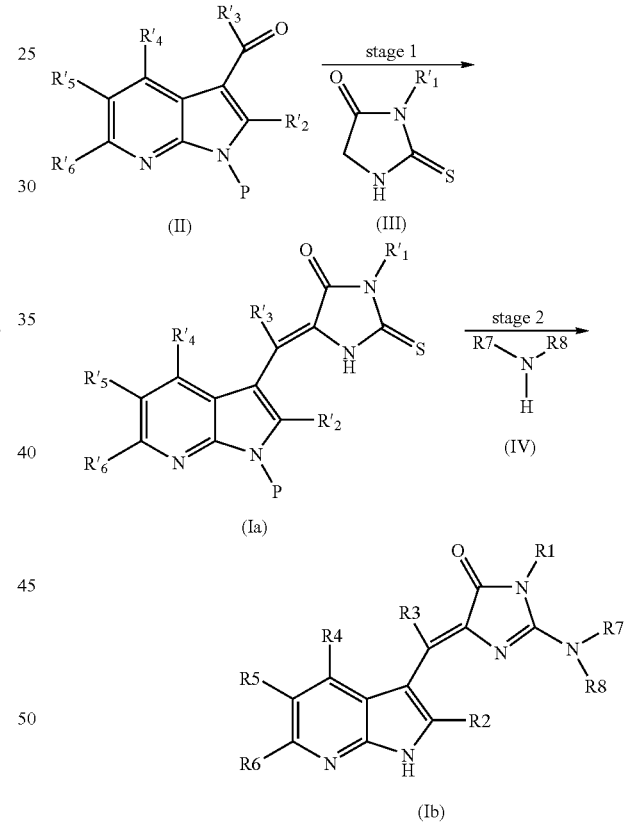

Scheme 1: The case when X-Y equals N═C—NR7R8 and NH—C (S):

In a first stage, the (5Z)-5-[(1H-pyrrolo[2,3-b]pyridin-3-yl)methylene]-2-thioxoimidazolidin-4-ones (Ia) are obtained by Knoevenagel reaction between a 2-thioxoimidazolidin-4-one (III) and an aldehyde, ketone or ester of formula (II) derived from 1H-pyrrolo[2,3-b]pyridine, in the presence of a base such as piperidine in a solvent such as ethanol. The temperature of choice for carrying out this reaction is between room temperature and the reflux temperature. All other usual conditions for a reaction of the Knoevenagel type can be used.

Table 1 gives examples of compounds (Ia) prepared according to Scheme 1:

TABLE 1

| Example (Ia) | Compound (II) | Compound of formula (III) | Compound of formula (Ia) |
|---|---|---|---|
| 1 | IIa | | |
| 2 | IIb | | |
| 3 | IIc | | |
| 4 | IId | | |
| 5 | IIe | | |
| 6 | IIa | | |

TABLE 1-continued

| Example (Ia) | Compound (II) | Compound of formula (III) | Compound of formula (Ia) |
|---|---|---|---|
| 13 | IIf | | |
| 14 | IIg | | |
| 15 | IIh | | |
| 16 | IIi | | |
| 17 | IIj | | |
| 18 | IIk | | |

TABLE 1-continued
| Example (Ia) | Compound (II) | Compound of formula (III) | Compound of formula (Ia) |
|---|---|---|---|
| 19 |  IIl | 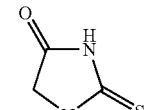 | 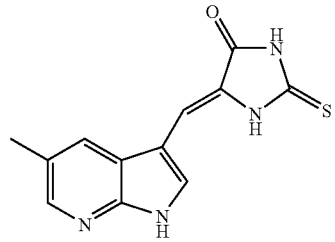 |
| 20 | 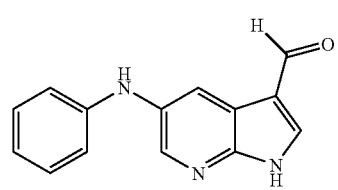 IIm | 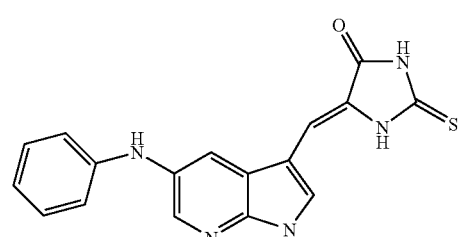 | 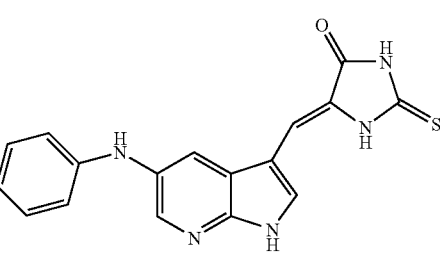 |
| 21 | 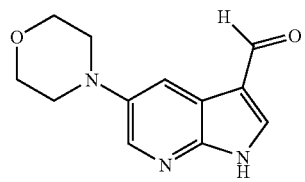 IIn | 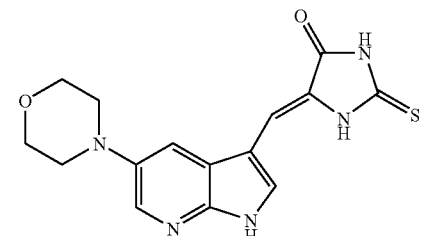 | 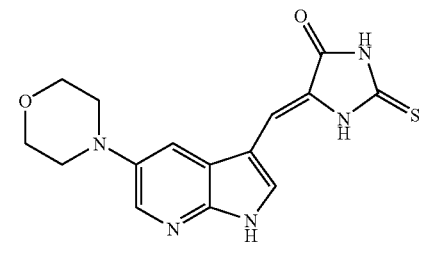 |
| 22 | 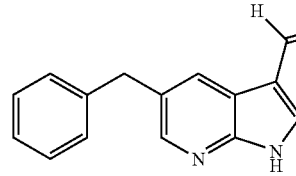 IIo | 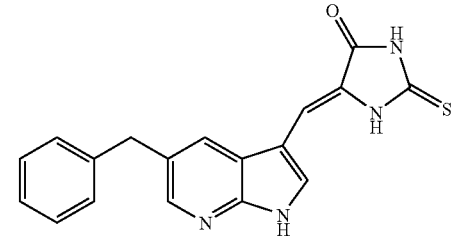 | 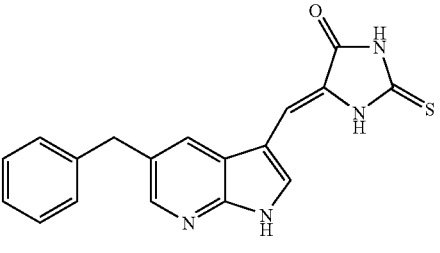 |
| 23 | 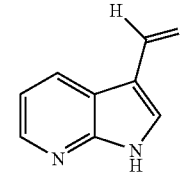 IIa | 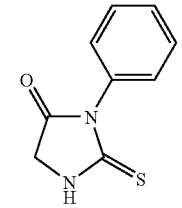 | 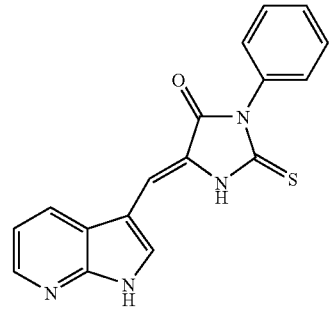 |

In a second stage, the (5Z)-5-[(1H-pyrrolo[2,3-b]pyridin-3-yl)methylene]-2-amino-3,5-dihydro-4H-imidazol-4-ones (Ib) are obtained by reaction between (5Z)-5-[(1H-pyrrolo[2,3-b]pyridin-3-yl)methylene]-2-thioxoimidazolidin-4-one (Ia) and a primary or secondary amine of general structure (IV) (with R7 and R8 as defined in general formula (I) for example in ethanol at a temperature varying from 120 to 170° C. in a sealed tube under microwave irradiation.

Table 2 gives examples of compounds (Ib) prepared according to Scheme 1:

TABLE 2

| Example (Ib) | Compound (Ia) | Amine (IV) | Compound of formula (Ib) |
|---|---|---|---|
| 7 | | | |
| 8 | | | |
| 9 | | | |
| 10 | | | |
| 11 | | | |

TABLE 2-continued
| Example (Ib) | Compound (Ia) | Amine (IV) | Compound of formula (Ib) |
|---|---|---|---|
| 12 | 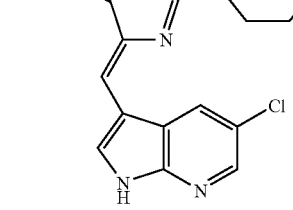 | 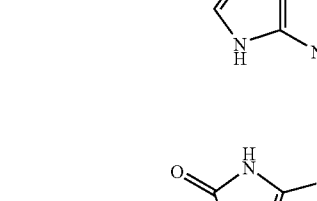 | 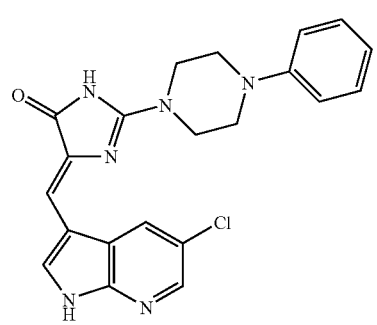 |
Table 4 gives examples of compounds I(b) prepared according to Scheme 1: these products of formula (I) are described hereunder as examples in the experimental section.
TABLE 4
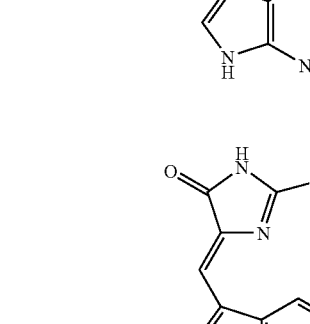
TABLE 4-continued
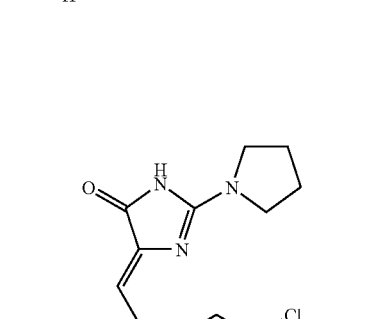
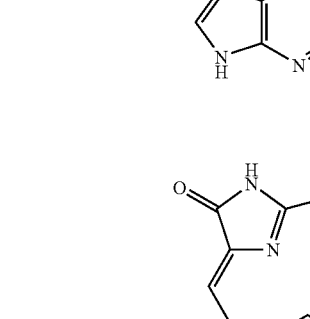

TABLE 4-continued
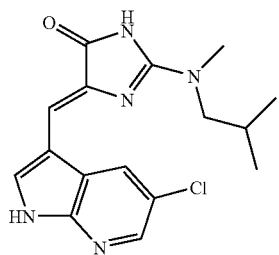
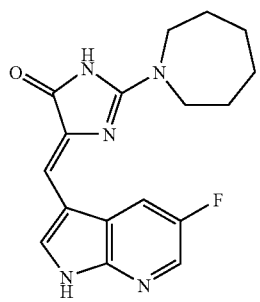
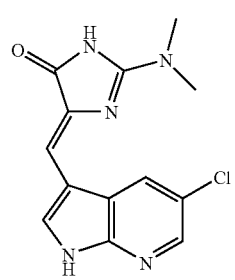
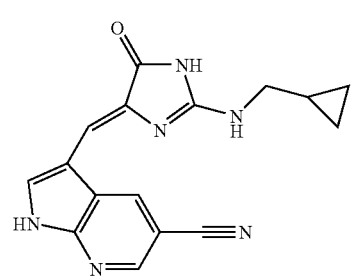
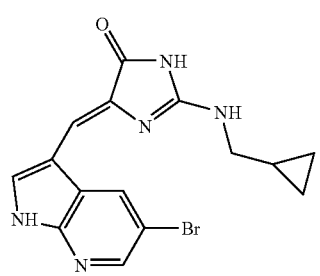
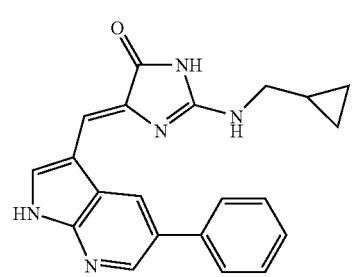
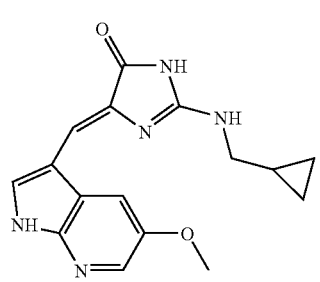
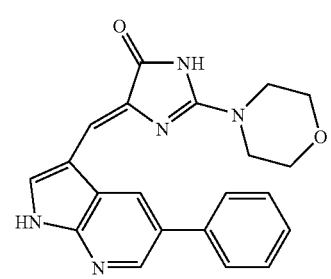
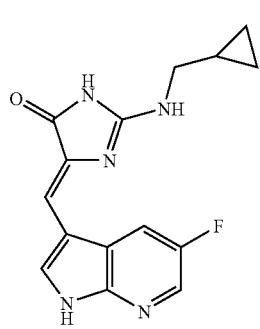
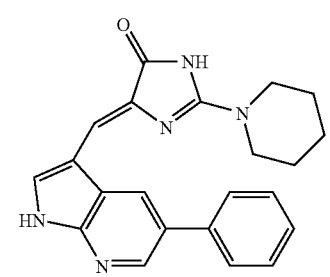

TABLE 4-continued
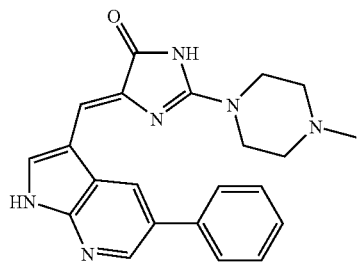
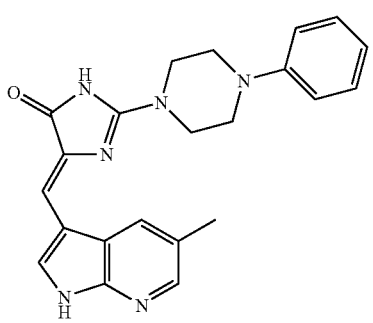
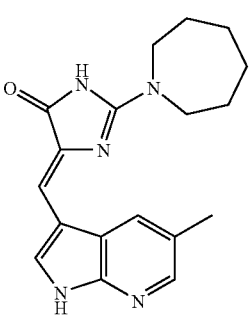
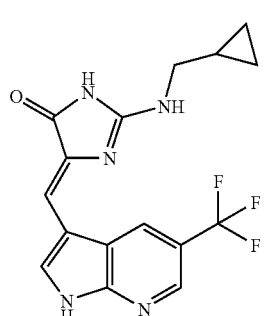
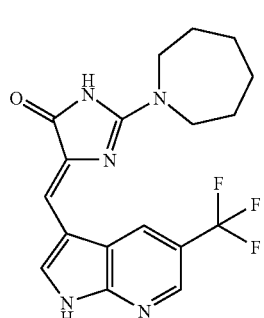
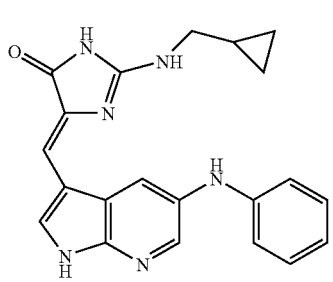

TABLE 4-continued
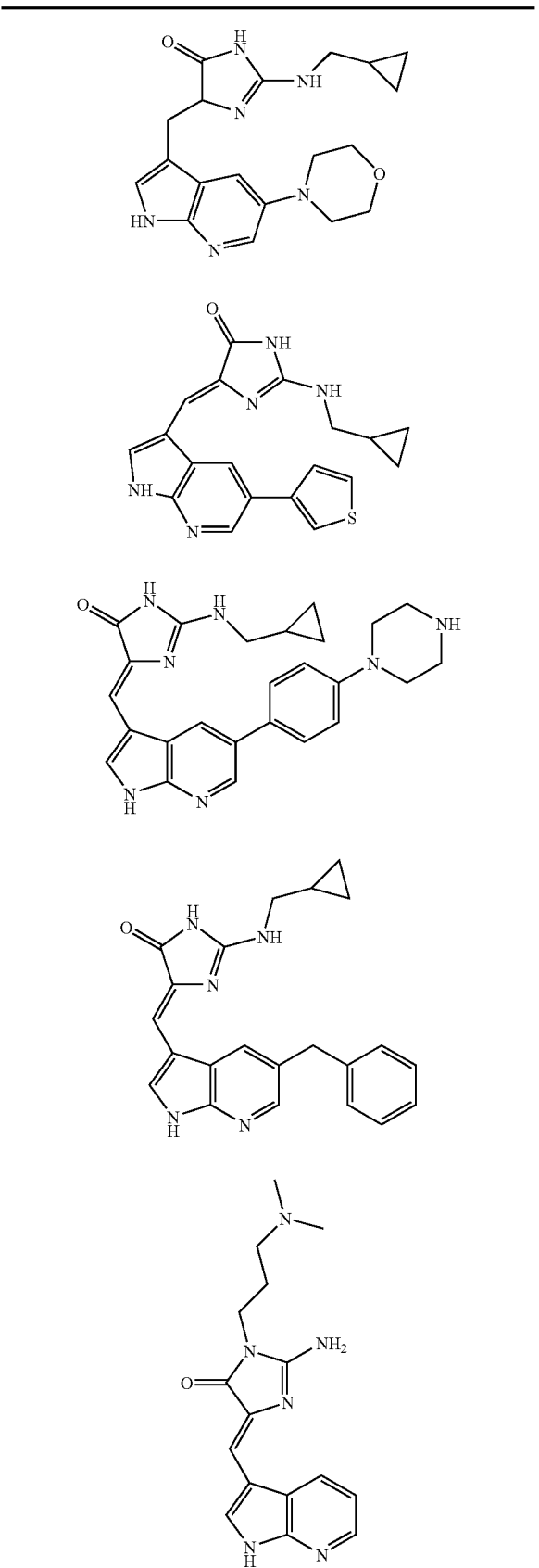
TABLE 4-continued
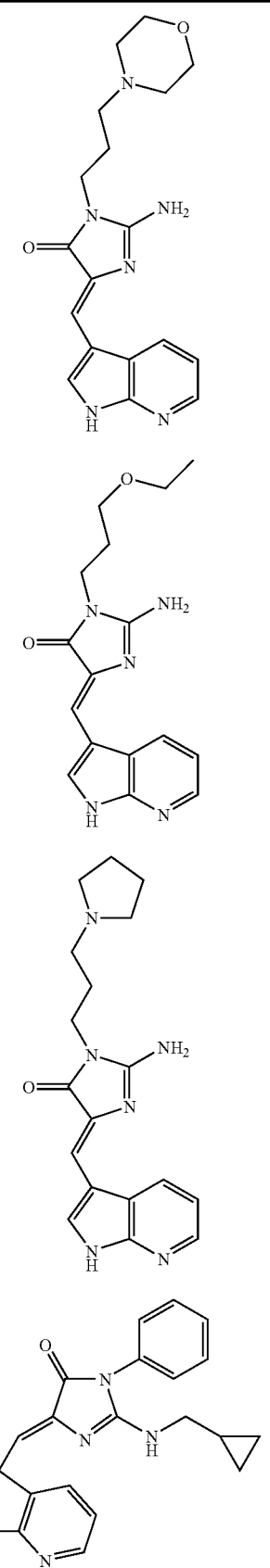

TABLE 4-continued

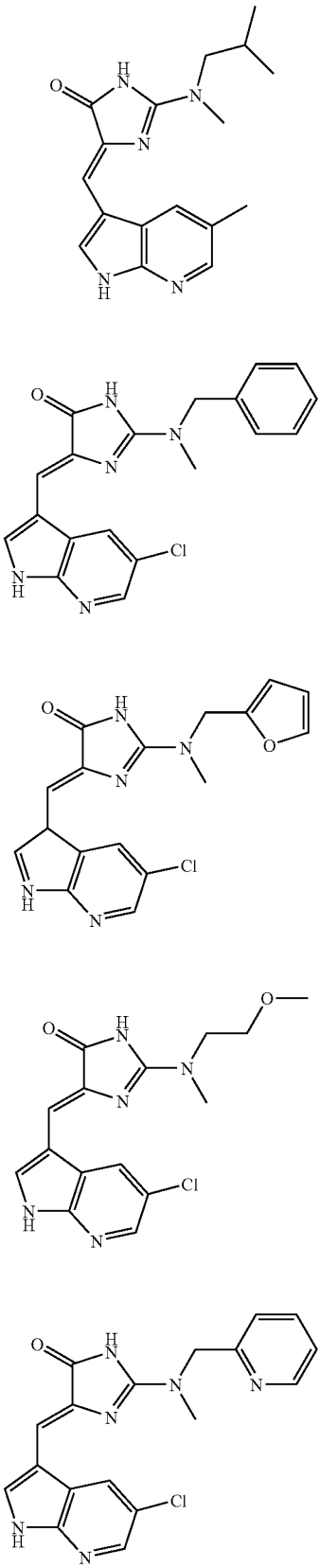

Scheme 2: The case when X-Y equals N=C—SR and N=C—NR7R8:

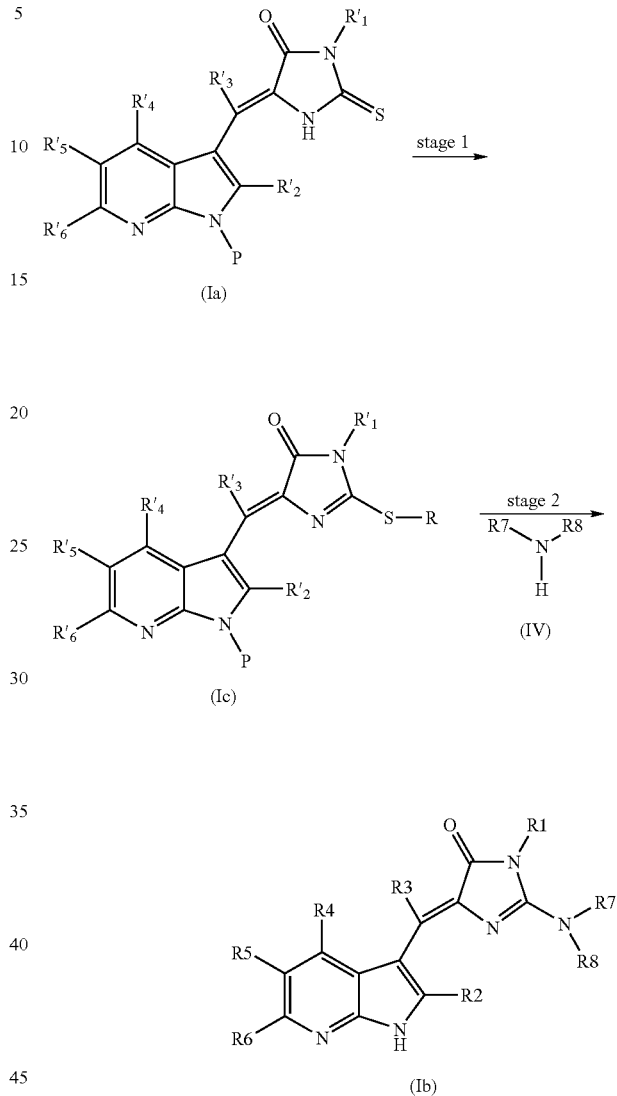

Alternatively, the (5Z)-5-[(1H-pyrrolo[2,3-b]pyridin-3-yl)methylene]-2-amino-3,5-dihydro-4H-imidazol-4-ones (Ic) can be prepared according to Scheme 2. The (5Z)-5-[(1H-pyrrolo[2,3-b]pyridin-3-yl)methylene]-2-thioxoimidazolidin-4-ones (Ia) are reacted with an alkylating agent (preferably, for example, methyl iodide) in the presence of a base such as diisopropylethylamine or sodium hydroxide, to give a thioalkylated derivative (Ic). The thioalkyl group is finally replaced in a second stage with an amine R7R8NH, to obtain the derivatives (Ib). Said replacement is carried out in a solvent such as acetonitrile or ethanol, at a temperature between room temperature and the reflux temperature, or alternatively in a sealed tube under microwave irradiation.

Table 6 gives examples of compounds I(c) prepared according to Scheme 2: these products of formula (Ic) are described hereunder as examples in the experimental section.

TABLE 6

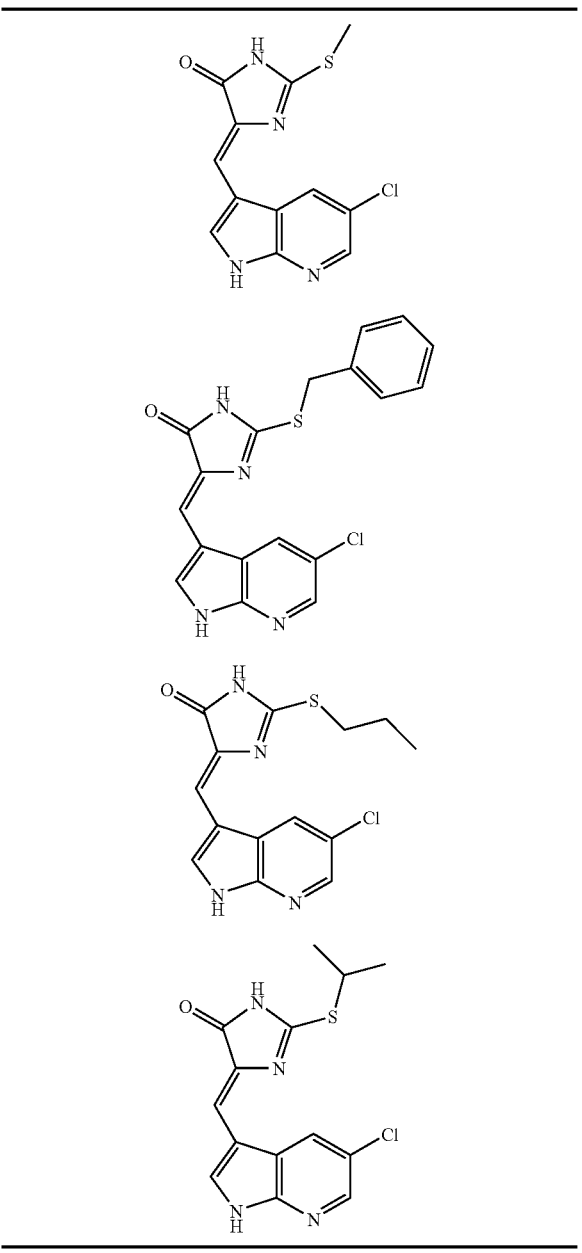

Scheme 3: The case when X-Y equals N═C─R; 1st synthetic route:

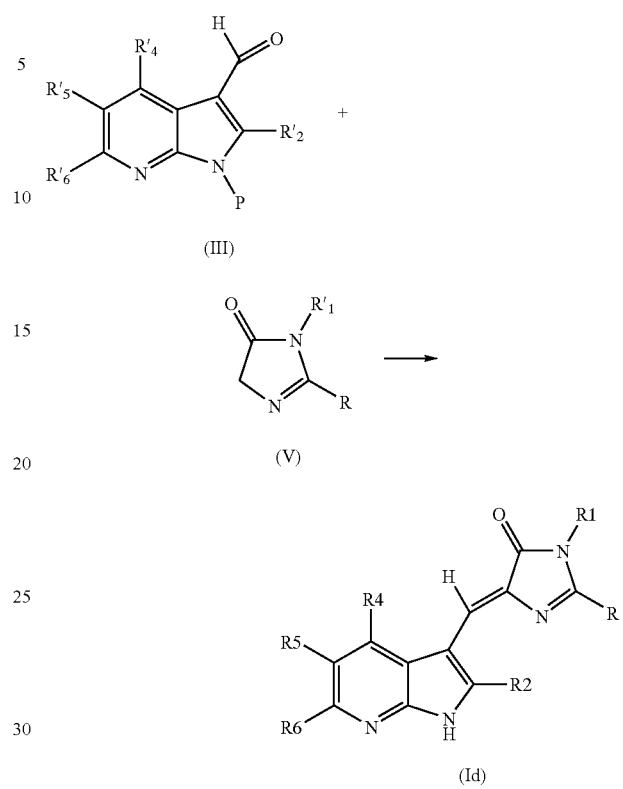

The (5Z)-5-[(1H-pyrrolo[2,3-b]pyridin-3-yl)methylene]-3,5-dihydro-4H-imidazolidin-4-ones (Id) are obtained by Knoevenagel reaction between an imidazolidin-4-one (V) and an aldehyde, ketone or ester of formula (II) derived from 1H-pyrrolo[2,3-b]pyridine, in the presence of a base such as piperidine in a solvent such as ethanol, according to Scheme 3. The temperature of choice for carrying out this reaction is between room temperature and the reflux temperature. All other usual conditions for a reaction of the Knoevenagel type, such as acidic conditions, can be used. The imidazolidin-4-ones (V) can be prepared according to J. Org. Chem. 1999, 64(22), 8084.

An example of preparation of a product of formula (I) according to Scheme 3 is given in the experimental section hereunder as Example 13 as presented in Table 3.

Scheme 4: The case when X-Y equals N=C—OR

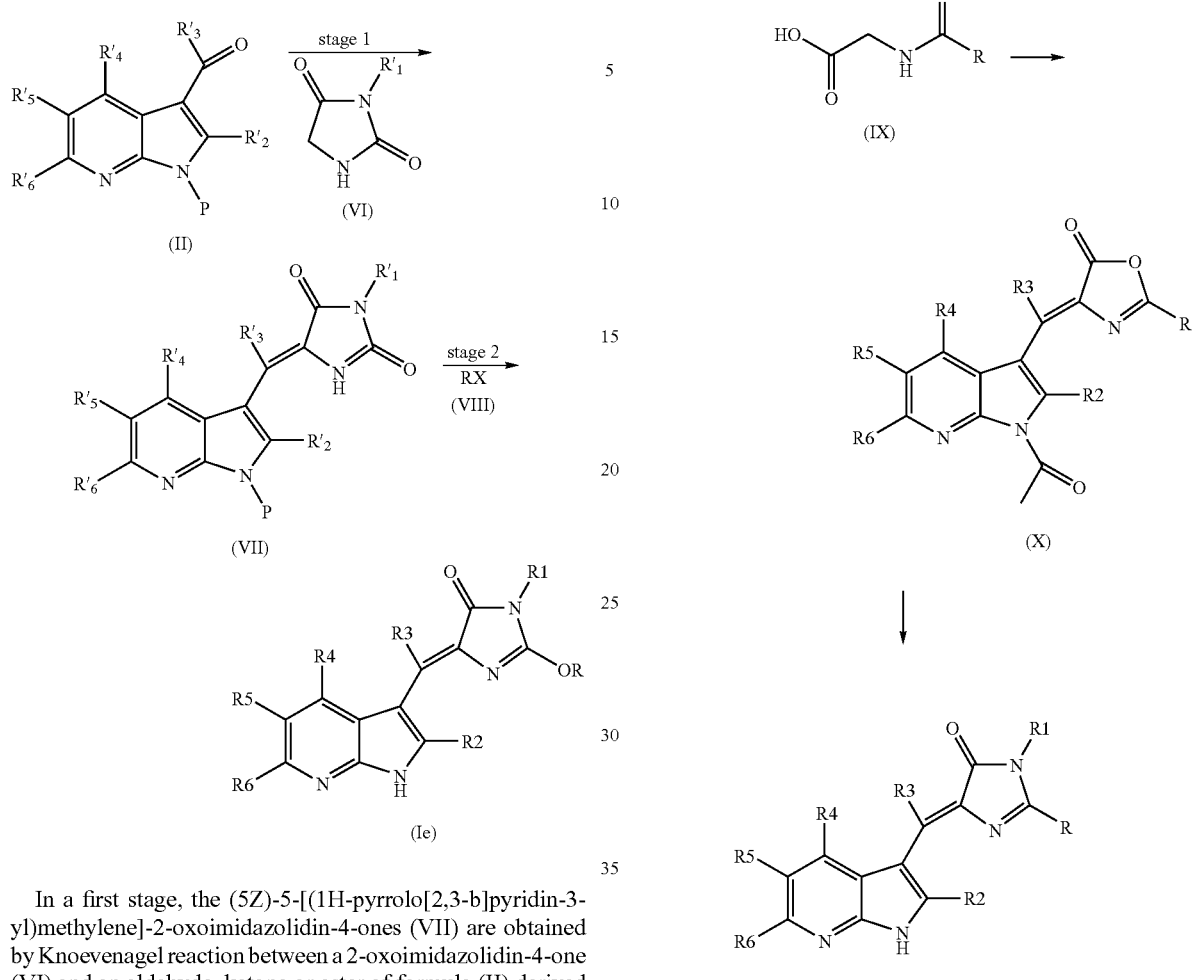

In a first stage, the (5Z)-5-[(1H-pyrrolo[2,3-b]pyridin-3-yl)methylene]-2-oxoimidazolidin-4-ones (VII) are obtained by Knoevenagel reaction between a 2-oxoimidazolidin-4-one (VI) and an aldehyde, ketone or ester of formula (II) derived from 1H-pyrrolo[2,3-b]pyridine, in the presence of a base such as piperidine in a solvent such as ethanol, according to Scheme 4. The temperature of choice for carrying out this reaction is between room temperature and reflux. Any other usual conditions for a reaction of the Knoevenagel type, such as acidic conditions, can be used.

In a second stage, the (5Z)-5-[(1H-pyrrolo[2,3-b]pyridin-3-yl)methylene]-2-alkoxy-3,5-dihydro-4H-imidazol-4-ones (Ie) are obtained by reaction between the (5Z)-5-[(1H-pyrrolo[2,3-b]pyridin-3-yl)methylene]-2-oxoimidazolidin-4-ones (VII) and an alkylating agent RX (VIII) in an inert solvent at a temperature varying from room temperature to reflux. Alkylating agents VIII that are known to promote O-alkylation, such as halides or salts of oxonium tetrafluoroborate are preferred.

Scheme 5: The case when X-Y equals N=C—R: 2nd synthetic route:

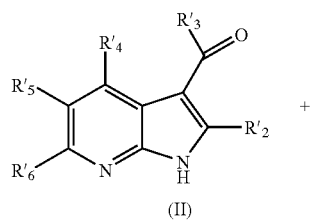

Alternatively, the (5Z)-5-[(1H-pyrrolo[2,3-b]pyridin-3-yl)methylene]-3,5-dihydro-4H-imidazolidin-4-ones (Id) are obtained from an oxazolone of formula (X). In a first stage, the cyclo-condensation of an N-acylated amide derivative of glycine (IX) on an aldehyde, ketone or ester of formula (II), in the presence of a base such as sodium acetate in acetic anhydride and at a temperature between room temperature and the reflux temperature, gives an oxazolone of formula (X). This reaction with indole derivatives has been described: J. Am. Chem. Soc. 1946, 647. In a second stage, the reaction of the oxazolone (X) with an excess of amine of formula R1NH2, or of ammonia, gives an imidazolone (Id). This reaction is carried out in a solvent such as methanol or ethanol, at a temperature between room temperature and the reflux temperature. Alternatively, this reaction can be carried out in a sealed tube under microwave irradiation, at a temperature between 80° C. and 200° C.

Table 5 The products of formula (I) in Table 5 can be prepared according to Scheme 3 or 5 above and are described as examples in the experimental section hereunder.

TABLE 5
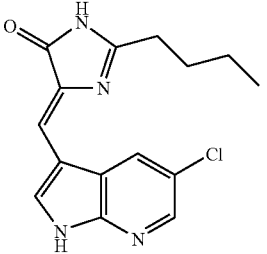
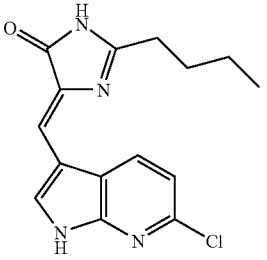
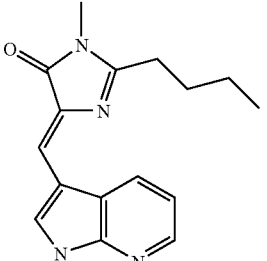
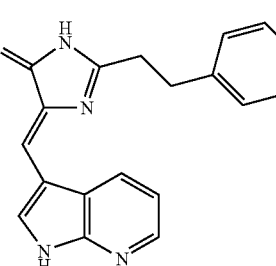
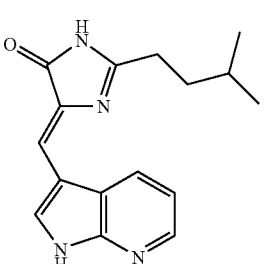
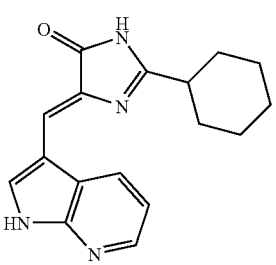
TABLE 5-continued
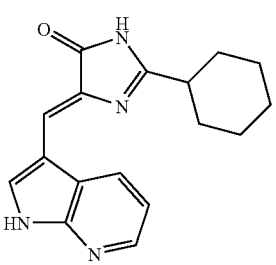
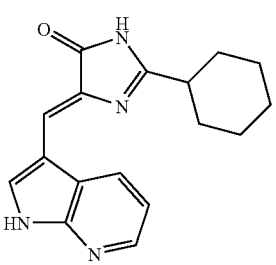
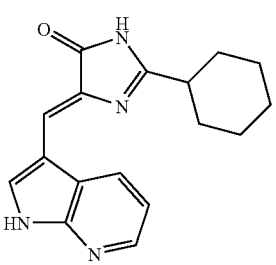
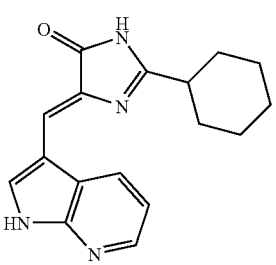
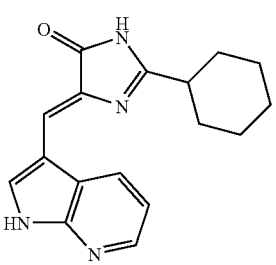

TABLE 5-continued
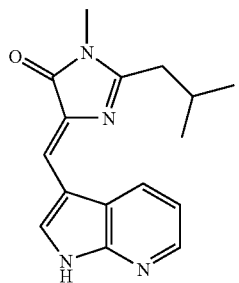
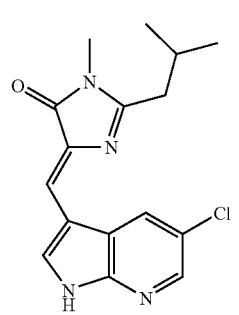
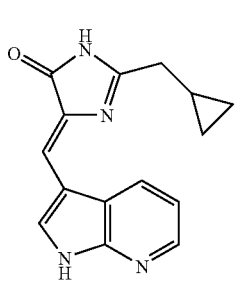
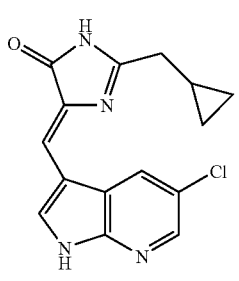
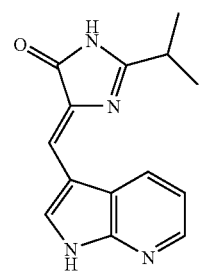
TABLE 5-continued
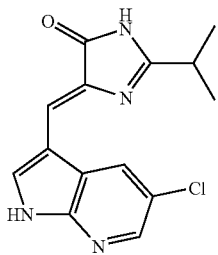
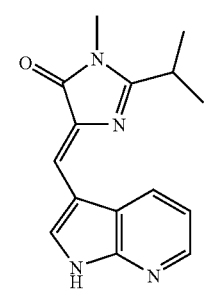
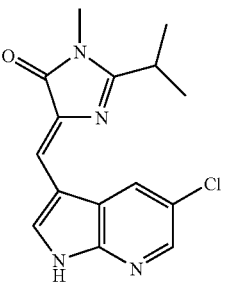
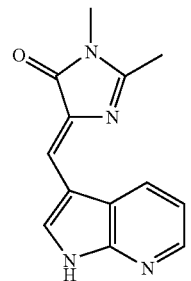
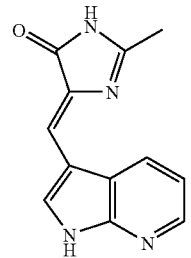

TABLE 5-continued
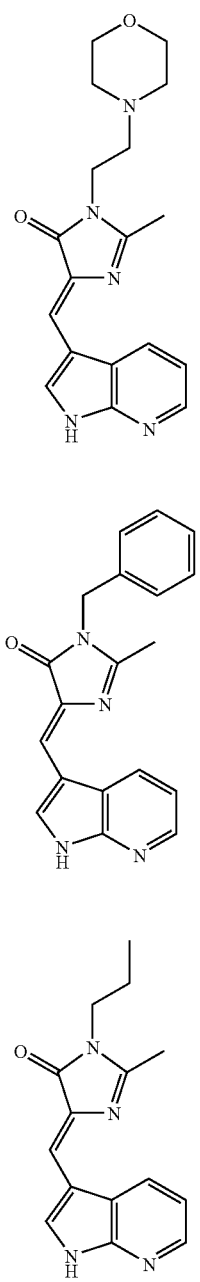
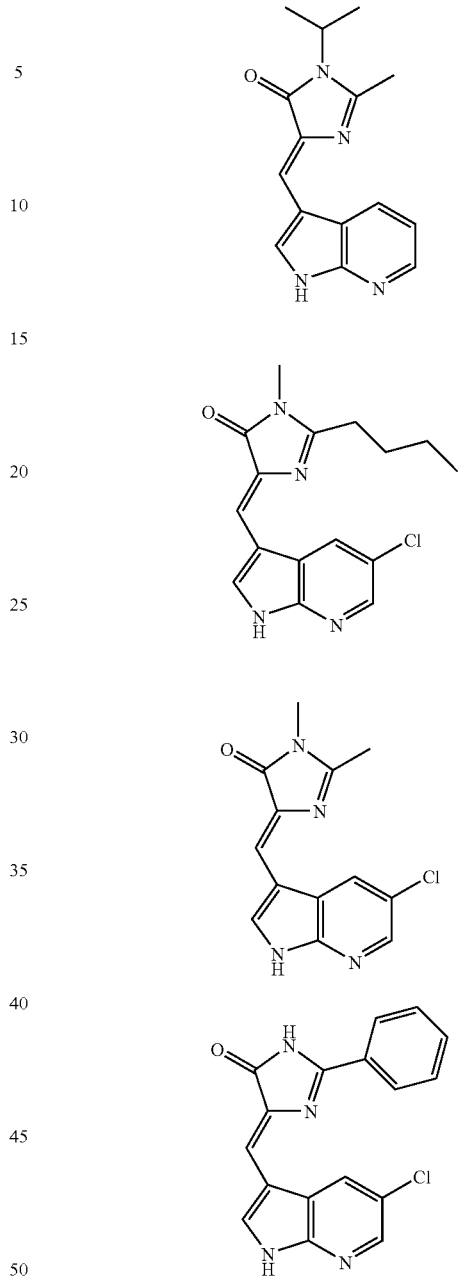
Scheme 6: The case when X-Y equals N=C—OR
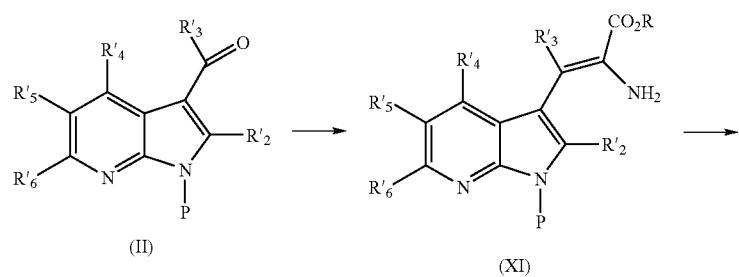

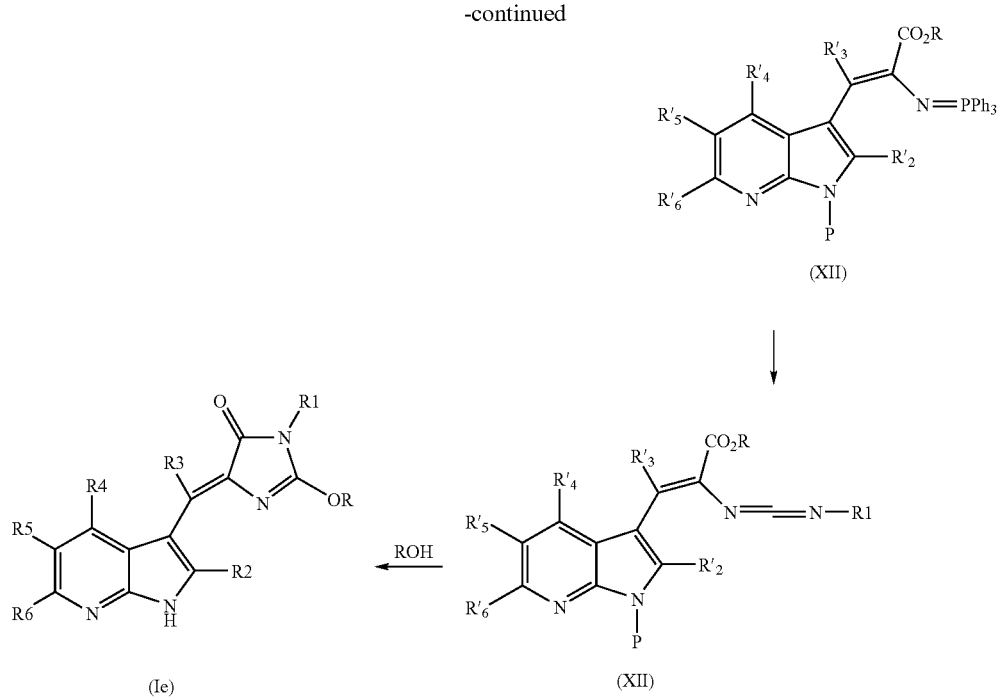

The compounds of type (Ie) can be prepared by analogy with the derivatives of imidazopyridines described for example in J. Org. Chem. 2001, 66(20), 6576-6584.

Scheme 7: The case when X-Y equals N═C—OR

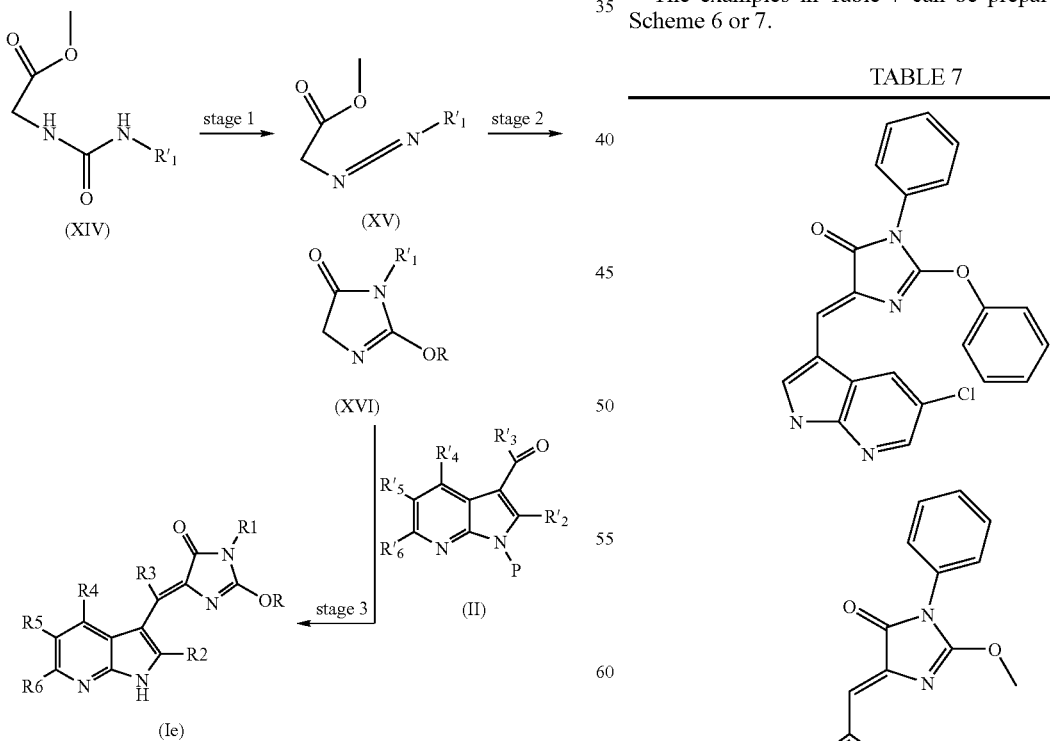

Alternatively, the molecules of type (Ie) can be prepared by first forming the imidazolone according to a method similar to that described for example in Bull. Korean Chem. Soc. 2007, 28(6), 913-914. In a first stage, the dehydration of a urea (XIV), with for example bromine and triphenylphosphine, gives a carbodiimide of formula (XV). In a second stage, addition of an alcohol and cyclization gives the imidazolone of formula (XVI). Finally, condensation on an aldehyde or ketone of formula (II) gives a compound (Ie).

The examples in Table 7 can be prepared according to Scheme 6 or 7.

TABLE 7

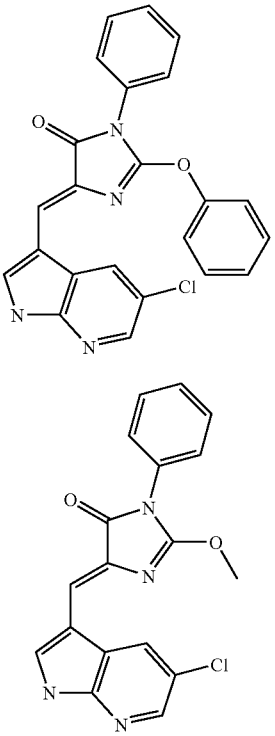

TABLE 7-continued
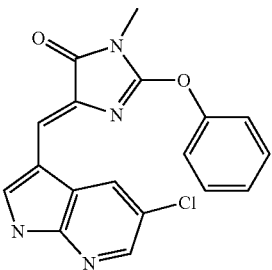
Table 8: the compounds in Table 8 can be prepared according to the methods described above in Schemes 1 to 7:
TABLE 8
examples of compounds I
| Compound | Example | Prepared according to scheme | NMR (400 MHz, DMSO-d6) |
|---|---|---|---|
|  | 100 | 1 | 1.59-2.36 (m, 10 H); 3.10 (b s, 1 H); 3.48 (b s, 2 H); 6.59 (s, 1 H); 8.14 (b s, 1 H); 8.23 (s, 1 H); 9.06 (b s, 1 H); 12.19 (b s, 1 H). |
|  | 101 | 1 | 0.06-0.55 (m, 4 H), 1.03 (m, 1 H), 2.28 (s, 3 H), 3.13 (m, 2 H), 6.64 (s, 1 H), 7.15 (m l, 1 M), 7.20-7.38 (m, 4 H), 8.16 (s l, 1 H), 8.19 (s l, 1 H), 8.90 (s l, 1 H), 10.4 (m l, 1 H), 12.01 (m l, 1 H). |
|  | 102 | 1 | 0.03-0.49 (m, 4 H), 1.04 (m, 1 H), 3.16 (m l, 2 H), 6.61 (s, 1 H), 7.20 (m l, 1 H), 7.38-7.63 (m, 4 H), 8.14 (s l, 1 H), 8.28 (s l, 1 H), 9.10 (m l, 1 H), 10.4 (m l, 1 H), 12.08 (m l, 1 H). |

TABLE 8-continued examples of compounds I

| Compound | Example | Prepared according to scheme | NMR (400 MHz, DMSO-d6) |
|---|---|---|---|
| | 103 | 1 | 0.94 (d, J = 6.2 Hz, 3 H), 1.16 (m, 2 H), 1.55-1.77 (m, 3 H), 3.03 (m, 2 H), 4.13 (m, 2 H), 6.62 (s, 1 H), 8.19 (s, 1 H), 8.23 (d, J = 2.5 Hz, 1 H), 9.03 (m l, 1 H), 10.4-12.5 (m l, 2 H). |
| | 104 | 1 | 1.70 (m, 2 H), 1.89 (m, 2 H), 2.85 (tt, J = 12.2, 3.7 Hz, 1 H), 3.15 (m, 2 H), 4.33 (m, 2 H), 6.65 (s, 1 H), 7.13-7.36 (m, 5 H), 8.23 (m, 2 H), 9.0 (s l, 1 H), 12.1 (s l, 1 H). |
| | 105 | 1 | 3.07 (m, 4 H), 3.74 (m, 4 H), 3.82 (s, 3 H), 6.69 (s, 1 H), 6.81-7.06 (m, 4 H), 8.24 (d, J = 2.3 Hz, 1 H), 8.26 (s, 1 H), 8.93 (s l, 1 H), 11.20 (m l, 1 H), 12.15 (m l, 1 H). |
| | 106 | 1 | 2.22 (s, 6 H), 3.24 (m, 4 H), 3.73 (m, 4 H), 6.48 (s l, 1 H), 6.64 (s l, 2 H), 6.69 (s, 1 H), 8.25 (m, 2 H), 8.96 (s l, 1 H), 11.20 (m l, 1 H), 12.25 (m l, 1 H). |
| | 107 | 1 | 4.58 (d, J = 5.7 Hz, 2 H), 6.64 (s l, 1 H), 7.08 (m, 2 H), 7.20 (t, J = 74.5 Hz, 1 H), 7.22 (s l, 1 H), 7.31 (d l, J = 7.8 Hz, 1 H), 7.43 (t, J = 7.8 Hz, 1 H), 7.76 (m l, 1 H), 8.17 (s l, 1 H), 8.22 (d l, J = 5.2 Hz, 1 H), 8.58 (d l, J = 7.9 Hz, 1 H), 10.7 (m l, 1 H), 11.92 (s l, 1 H). |

TABLE 8-continued examples of compounds I

| Compound | Example | Prepared according to scheme | NMR (400 MHz, DMSO-d6) |
|---|---|---|---|
| (structure) | 108 | 2 | 1.47-1.97 (m, 8 H), 2.96 (s l, 3 H), 4.62 (m, 1 H), 6.58 (s l, 1 H), 8.14 (s l, 1 H), 8.22 (s l, 1 H), 9.22 (s l, 1 H), 11.07 (m l, 1 H), 12.16 (s l, 1 H). |
| (structure) | 109 | 2 | 0.34 (m, 2 H), 0.52 (m, 2 H), 0.93 (t, J = 8 Hz, 3 H), 1.15 (m, 1 H), 1.68 (q, J = 8 Hz, 2 H), 3.42 (d, J = 8 Hz, 2 H), 3.50 (m, 2 H), 6.56 (s, 1 H), 8.07 (s, 1 H), 8.20 (s, 1 H), 9.09 (s, 1 H), 10.9 (l, 1 H), 11.9 (s l, 1 H). |
| (structure) | 110 | 1 | 0.85 (d, J = 6.8 Hz, 6 H), 2.01 (m, 1 H), 3.10 (s, 3 H), 3.26 (d, J = 6.8 Hz, 2 H), 6.71 (s, 1 H), 7.37 (t, J = 7.6 Hz, 1 H), 7.48 (t, J = 7.6 Hz, 2 H), 7.75 (d, J = 7.6 Hz, 2 H), 8.20 (d, J = 2.9 Hz, 1 H), 8.54 (d, J = 2 Hz, 1 H), 9.08 (s l, 1 H), 11.05 (s l, 1 H), 12.0 (s l, 1 H). |
| (structure) | 111 | 1 | 1.55-2.30 (m, 10 H), 3.10 (s, 3 H), 3.40-3.60 (m, 2 H), 6.71 (s, 1 H), 7.36 (t, J = 7.7 Hz, 1 H), 7.48 (t, J = 7.7 Hz, 2 H), 7.77 (d, J = 7.7 Hz, 2 H), 8.21 (m l, 1 H), 8.55 (s l, 1 H), 9.09 (m l, 1 H), 11.07 (m l, 1 H), 12.05 (m l, 1 H). |
| (structure) | 112 | 1 | 2.40 (m, 6 H), 3.50 (m, 2 H), 3.56 (m, 4 H), 6.72 (s, 1 H), 6.88 (s l, 1 H), 7.37 (t, J = 7.6 Hz, 1 H), 7.49 (t, J = 7.6 Hz, 2 H), 7.78 (d, J = 7.6 Hz, 2 H), 8.20 (s, 1 H), 8.55 (s, 1 H), 9.11 (s, 1 H), 10.4 (s l, 1 H), 12.0 (s l, 1 H). |

TABLE 8-continued
examples of compounds I
| Compound | Example | Prepared according to scheme | NMR (400 MHz, DMSO-d6) |
|---|---|---|---|
| 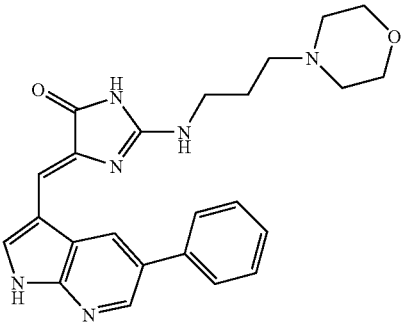 | 113 | 1 | 1.72 (m, 2 H), 2.31 (m, 6 H), 3.41 (m, 2 H), 3.56 (m, 4 H), 6.71 (s, 1 H), 7.12 (s l, 1 H), 7.37 (t, J = 7.6 Hz, 1 H), 7.49 (t, J = 7.6 Hz, 2 H), 7.78 (d, J = 7.6 Hz, 2 H), 8.18 (s, 1 H), 8.55 (s, 1 H), 9.13 (s, 1 H), 10.5 (s l, 1 H), 12.0 (s l, 1 H). |
| 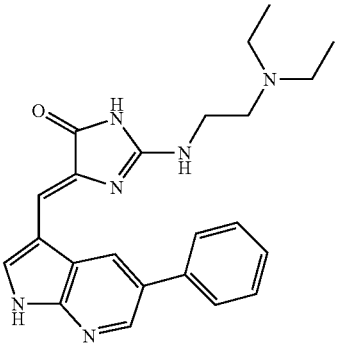 | 114 | 1 | 0.97 (t, J = 7 Hz, 6 H), 2.50 (m, 4 H), 2.61 (t, J = 6.4 Hz, 2 H), 3.43 (m, 2 H), 6.73 (s, 1 H), 6.82 (s l, 1 H), 7.38 (t, J = 8 Hz, 1 H), 7.49 (t, J = 8 Hz, 2 H), 7.79 (d, J = 8 Hz, 2 H), 8.21 (s, 1 H), 8.56 (s, 1 H), 9.05 (s, 1 H), 10.49 (s l, 1 H), 12.06 (s l, 1 H). |
| 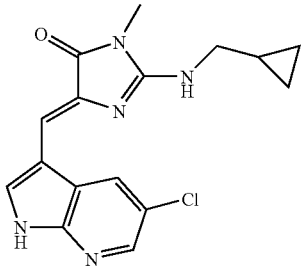 | 115 | 1 | 0.35 (m, 2 H), 0.52 (m, 2 H), 1.24 (m, 1 H), 3.07 (s, 3 H), 3.35 (t, J = 7 Hz, 2 H), 6.73 (s, 1 H), 7.65 (t, J = 6 Hz, 1 H), 8.19 (d, J = 2 Hz, 1 H), 8.24 (d, J = 2 Hz, 1 H), 9.28 (d, J = 2 Hz, 1 H), 12.2 (s l, 1 H). |
| 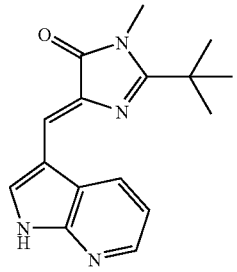 | 116 | 5 | 1.43 (s, 9 H); 3.30 (s, 3 H); 7.19 (dd, J = 8.1, 4.6 Hz, 1 H); 7.35 (s, 1 H); 8.29 (dd, J = 4.6, 1.5 Hz, 1 H), 8.38 (s, 1 H), 9.07 (d l, J = 8.1 Hz, 1 H), 12.4 (b, 1 H). |
| 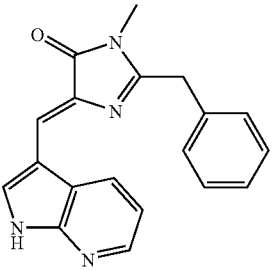 | 117 | 5 | 3.10 (s, 3 H), 4.10 (s, 2 H), 7.00 (dd, J = 7.9, 4.7 Hz, 1 H), 7.29 (s, 1 H), 7.31-7.48 (m, 5 H), 8.24 (dd, J = 4.7, 1.4 Hz, 1 H), 8.29 (d, J = 2.2 Hz, 1 H), 8.81 (dd, J = 7.9, 1.4 Hz, 1 H), 12.3 (m l, 1 H). |

TABLE 8-continued examples of compounds I

| Compound | Example | Prepared according to scheme | NMR (400 MHz, DMSO-d6) |
|---|---|---|---|
| (5-chloro-7-azaindole linked via methylidene to 2-cyclopropyl-imidazolinone, NH) | 118 | 3 | 1.12 (d, J = 6.6 Hz, 4 H), 1.85 (q, J = 6.6 Hz, 1 H), 7.06 (s, 1 H), 8.28 (d, J = 2.6 Hz, 1 H), 8.32 (s, 1 H), 9.25 (d, J = 2.6 Hz, 1 H), 11.22 (m l, 1 H), 12.36 (m l, 1 H). |
| (7-azaindole linked via methylidene to 2-cyclopropyl-imidazolinone, NH) | 119 | 3 | 1.06-1.13 (m, 4 H), 1.87 (m, 1 H), 7.08 (s, 1 H), 7.18 (dd, J = 8.1, 4.6 Hz, 1 H), 8.28 (dd, J = 4.6, 1.5 Hz, 1 H), 8.31 (s, 1 H), 8.83 (dd, J = 8.1, 1.5 Hz, 1 H), 11.7 (m l, 1 H), 12.33 (m l, 1 H). |
| (7-azaindole linked via methylidene to 2-cyclopropyl-N-methyl-imidazolinone) | 120 | 3 | 1.10-1.19 (m, 4 H), 2.06 (m, 1 H), 3.23 (s, 3 H), 7.19 (dd, J = 7.8, 4.9 Hz, 1 H), 7.22 (s, 1 H), 8.29 (dd, J = 4.9, 1.5 Hz, 1 H), 8.32 (s, 1 H), 8.86 (dd, J = 7.8, 1.5 Hz, 1 H), 12.35 (s l, 1 H). |
| (5-chloro-7-azaindole linked via methylidene to 2-cyclopropyl-N-methyl-imidazolinone) | 121 | 3 | 1.17 (d, J = 6.6 Hz, 4 H), 2.08 (q, J = 6.6 Hz, 1 H), 3.23 (s, 3 H), 7.21 (s, 1 H), 8.29 (d, J = 2.6 Hz, 1 H), 8.33 (s, 1 H), 9.32 (d, J = 2.6 Hz, 1 H), 12.58 (s l, 1 H). |
| (7-azaindole linked via methylidene to 2-tert-butyl-imidazolinone, NH) | 122 | 3 | 1.33 (s, 9 H), 7.18 (m, 1 H), 7.20 (s, 1 H), 8.29 (m, 1 H), 8.35 (s, 1 H), 9.02 (d, J = 8 Hz, 1 H), 11.2 (s l, 1 H), 12.3 (s l, 1 H). |

TABLE 8-continued examples of compounds I

| Compound | Example | Prepared according to scheme | NMR (400 MHz, DMSO-d6) |
|---|---|---|---|
| (structure) | 123 | 3 | 1.37 (s, 9 H), 7.17 (s, 1 H), 8.28 (d, J = 2 Hz, 1 H), 8.32 (s, 1 H), 9.55 (s, 1 H), 11.2 (s l, 1 H), 12.5 (s l, 1 H). |
| (structure) | 124 | 6 | 6.89 (m, 1 H), 7.32 (s, 1 H), 7.35-7.7 (m, 10 H), 8.09 (s, 1 H), 8.21 (s, 1 H), 8.60 (d, J = 8.6 Hz, 1 H), 12.25 (s l, 1 H). |
| (structure) | 125 | 7 | 3.20 (s, 3 H), 6.90 (s, 1 H), 7.21 (s, 1 H), 7.3-7.7 (m, 5 H), 8.04 (s, 1 H), 8.20 (s, 1 H), 8.59 (d, J = 7.6 Hz, 1 H), 12.2 (s l, 1 H). |
| (structure) | 126 | 2 | 2.81 (s, 3 H), 3.13 (s, 3 H), 7.22 (s, 1 H), 8.32 (d, J = 2 Hz, 1 H), 8.43 (s, 1 H), 9.36 (d, J = 2 Hz, 1 H), 12.60 (s l, 1 H). |
| (structure) | 127 | 2 | 3.10 (s, 3 H), 4.11 (d, J = 6.8 Hz, 2 H), 5.23 (d, J = 10 Hz, 1 H), 5.45 (d, J = 19 Hz, 1 H), 6.10 (m, 1 H), 7.22 (s, 1 H), 8.30 (d, J = 2 Hz, 1 H), 8.43 (s, 1 H), 9.25 (d, J = 2 Hz, 1 H), 12.6 (s l, 1 H). |

TABLE 8-continued examples of compounds I

| Compound | Example | Prepared according to scheme | NMR (400 MHz, DMSO-d6) |
|---|---|---|---|
|  | 128 | 2 | 1.57 (d, J = 6.6 Hz, 6 H), 3.07 (s, 3 H), 4.20 (m, 1 H), 7.19 (s, 1 H), 8.32 (d, J = 2 Hz, 1 H), 8.39 (s, 1 H), 9.37 (d, J = 2 Hz, 1 H), 12.6 (s l, 1 H). |
|  | 129 | 2 | 2.47 (m, 4 H), 2.79 (t, J = 6.8 Hz, 2 H), 3.10 (s, 3 H), 3.60 (m, 6 H), 7.22 (s, 1 H), 8.31 (d, J = 2 Hz, 1 H), 8.44 (s, 1 H), 9.18 (d, J = 2 Hz, 1 H), 12.6 (s l, 1 H). |

Said products obtained by the above schemes can be products of formula (I) or alternatively, to obtain products of formula (I) or for transformation to other products of formula (I), can be submitted, if desired and if necessary, in any order, to one or more transformation reactions known by a person skilled in the art, for example the following reactions:

a) a reaction of esterification or of amidation of an acid function,
b) if applicable, a reaction of oxidation of an alkylthio group to the corresponding sulphoxide or sulphone,
c) a reaction of reduction of the free or esterified carboxy function to an alcohol function,
d) a reaction of transformation of an alkoxy function to a hydroxyl function, or alternatively of a hydroxyl function to an alkoxy function,
e) a reaction of elimination of the protecting groups that protected reactive functions may be carrying,
f) a reaction of salification with an inorganic or organic acid or with a base to obtain the corresponding salt,
g) a reaction for resolving racemic forms to resolved products, said products of formula (I) thus obtained being in all possible isomeric forms: racemates, enantiomers and diastereoisomers.

It should be noted that said reactions of transformation of substituents into others substituents can also be carried out on the starting products as well as on the intermediates as defined above before continuing the synthesis according to the reactions stated in the method described above.

The methods described in the above schemes can be carried out according to the usual conditions known by a person skilled in the art and notably according to the reaction conditions described hereunder for preparation of the examples of the present application.

Among the starting products used for preparation of the products of formula (I) according to the present invention, some are available commercially or can be prepared according to the usual methods known by a person skilled in the art.

It is also possible, notably, to prepare some starting products from products that are known or are available commercially, for example by submitting them to one or more reactions known by a person skilled in the art.

The experimental section hereunder gives examples of said starting products.

For preparation of the products of formula (I) according to the present invention, the various reactive functions that can be carried by some compounds of the reactions defined above can, if necessary, be protected: this relates for example to free hydroxyl, acyl, carboxy radicals or alternatively amino and monoalkylamino radicals which can be protected with appropriate protecting groups.

We may mention the following list, which is not exhaustive, of examples of protection of reactive functions:

hydroxyl groups can be protected for example with alkyl radicals such as tert-butyl, trimethylsilyl, tert-butyldimethylsilyl, methoxy-methyl, tetrahydropyranyl, benzyl or acetyl, amino groups can be protected for example with acetyl, trityl, benzyl, tert-butoxycarbonyl, BOC, benzyloxycarbonyl, phthalimido or other radicals known in peptide chemistry, acyl groups such as the formyl group can be protected for example in the form of cyclic or acyclic ketals or thioketals such as dimethyl or diethylketal or ethylene dioxyketal, or diethylthioketal or ethylenedithioketal, the acid functions of the products described above can, if desired, be amidated with a primary or secondary amine for example in methylene chloride in the presence, for example, of 1-ethyl-3-(dimethylaminopropyl) carbodiimide hydrochloride at room temperature, the acid functions can be protected for example in the form of esters formed with easily cleavable esters such as benzyl or tert-butyl esters or the esters known in peptide chemistry.

Notably, NH or 1H-pyrrolo[2,3-b]pyridine can be protected if necessary with paratoluenesulphonyl, phenylsulphonyl, acetyl, triisopropylsilyl, tert-butyldimethylsilyl or trimethylsilylethoxymethyl.

Reactions a) to g) can be carried out, for example, as stated hereunder.

a) The products described above can if desired undergo, on any carboxy functions present, reactions of esterification or amidation, which can be carried out according to the usual methods known by a person skilled in the art. The reactions of amidation can notably be carried out in the presence of a coupling agent such as a carbodiimide derivative. We may mention as examples N-(3-dimethylaminopropyl), N'-ethyl-carbodiimide (EDCI), N,N'-diisopropyl-carbodiimide (DIC) or N,N'-dicyclohexyl-carbodiimide.

b) Any alkylthio groups in the products described above can, if desired, be transformed into the corresponding sulphoxide or sulphone functions in the usual conditions known by a person skilled in the art, for example with peracids such as peracetic acid or metachloroperbenzoic acid or alternatively with ozone, oxone, sodium periodate in a solvent such as methylene chloride or dioxan at room temperature.

Production of the sulphoxide function can be promoted with an equimolar mixture of the product containing an alkylthio group and of the reagent such as notably a peracid.

Production of the sulphone function can be promoted with a mixture of the product containing an alkylthio group with an excess of the reagent such as notably a peracid.

c) Any free or esterified carboxy functions in the products described above can, if desired, be reduced to an alcohol function by the methods known to a person skilled in the art: any esterified carboxy functions can, if desired, be reduced to an alcohol function by the methods known by a person skilled in the art and notably with lithium and aluminium hydride in a solvent such as tetrahydrofuran or alternatively dioxan or ethyl ether.

Any free carboxy functions in the products described above can, if desired, be reduced to an alcohol function notably with boron hydride.

d) Any alkoxy functions such as notably methoxy in the products described above can, if desired, be transformed to hydroxyl functions in the usual conditions known by a person skilled in the art, for example with boron tribromide in a solvent such as methylene chloride, with pyridine hydrobromide or hydrochloride or alternatively with hydrobromic or hydrochloric acid in water or trifluoroacetic acid under reflux.

It is to be understood that the reactions described above can be carried out as stated or alternatively, if applicable, according to other usual methods known by a person skilled in the art.

e) The elimination of protecting groups, for example those stated above, can be carried out in the usual conditions known to a person skilled in the art, notably by acid hydrolysis carried out with an acid such as hydrochloric, benzenesulphonic or para-toluenesulphonic, formic or trifluoroacetic acid or alternatively by catalytic hydrogenation.

The phthalimido group can be eliminated with hydrazine.

A list of various protecting groups that can be used is given for example in patent BF 2 499 995.

f) The products described above can, if desired, undergo reactions of salification for example by an inorganic or organic acid or by an inorganic or organic base according to the usual methods known by a person skilled in the art: said reaction of salification can be performed for example in the presence of hydrochloric acid or alternatively tartaric, citric or methanesulphonic acid, in an alcohol such as ethanol or methanol.

g) Any optically active forms of the products described above can be prepared by resolution of racemates according to the usual methods known by a person skilled in the art.

The products of formula (I) as defined above as well as their salts of addition with acids display interesting pharmacological properties notably on account of their kinase inhibiting properties as mentioned above.

It should be noted that as certain protein kinases play a key role in the initiation, development and completion of the events of the cell cycle, molecules that inhibit said kinases are likely to limit undesirable cellular proliferation such as that observed in cancers, and can be used in the prevention, control or treatment of neurodegenerative diseases such as Alzheimer's disease or neuronal apoptosis.

The products of the present invention can notably be used for the treatment of tumours.

The products of the invention can thus also enhance the therapeutic effects of antitumour agents currently used.

The products of formula (I) of the present invention therefore possess quite particularly antiproliferative properties.

These properties justify their application in therapeutics and the invention relates in particular to the products of formula (I) as defined above as medicinal products, said products of formula (I) being in all possible isomeric forms: racemates, enantiomers and diastereoisomers, as well as salts of addition of said products of formula (I) with pharmaceutically acceptable inorganic and organic acids or inorganic and organic bases.

The invention relates in particular to, as medicinal products, the products described hereunder in the examples and notably the products having the following names:

(5Z)-5-(1H-pyrrolo[2,3-b]pyridin-3-ylmethylene)-2-thioxoimidazolidin-4-one (5Z)-5-[(5-chloro-1H-pyrrolo[2,3-b]pyridin-3-yl)methylene]-2-thioxoimidazolidin-4-one (5Z)-2-[(cyclopropylmethyl)amino]-5-(1H-pyrrolo[2,3-b]pyridin-3-ylmethylene)-3,5-dihydro-4H-imidazol-4-one (5Z)-5-[(5-chloro-1H-pyrrolo[2,3-b]pyridin-3-yl)methylene]-2-[(cyclopropylmethyl)amino]-3,5-dihydro-4H-imidazol-4-one (5Z)-5-[(6-chloro-1H-pyrrolo[2,3-b]pyridin-3-yl)methylene]-2-[(cyclopropylmethyl)amino]-3,5-dihydro-4H-imidazol-4-one (5Z)-2-[(cyclopropylmethyl)amino]-3-methyl-5-(1H-pyrrolo[2,3-b]pyridin-3-ylmethylene)-3,5-dihydro-4H-imidazol-4-one (5Z)-2-butyl-5-(1H-pyrrolo[2,3-b]pyridin-3-ylmethylene)-3,5-dihydro-4H-imidazol-4-one (5Z)-2-azepan-1-yl-5-[(5-chloro-1H-pyrrolo[2,3-b]pyridin-3-yl)methylidene]-3,5-dihydro-4H-imidazol-4-one (5Z)-5-[(5-chloro-1H-pyrrolo[2,3-b]pyridin-3-yl)methylidene]-2-piperidin-1-yl-3,5-dihydro-4H-imidazol-4-one (5Z)-5-[(5-chloro-1H-pyrrolo[2,3-b]pyridin-3-yl)methylidene]-2-[methyl(2-methylpropyl)amino]-3,5-dihydro-4H-imidazol-4-one (5Z)-5-[(5-bromo-1H-pyrrolo[2,3-b]pyridin-3-yl)methylidene]-2-[(cyclopropylmethyl)amino]-3,5-dihydro-4H-imidazol-4-one (5Z)-2-[(cyclopropylmethyl)amino]-5-[(5-methoxy-1H-pyrrolo[2,3-b]pyridin-3-yl)methylidene]-3,5-dihydro-4H-imidazol-4-one (5Z)-2-[(cyclopropylmethyl)amino]-5-[(5-fluoro-1H-pyrrolo[2,3-b]pyridin-3-yl)methylidene]-3,5-dihydro-4H-imidazol-4-one (5Z)-2-azepan-1-yl-5-[(5-fluoro-1H-pyrrolo[2,3-b]pyridin-3-yl)methylidene]-3,5-dihydro-4H-imidazol-4-one 3-[(Z)-{2-[(cyclopropylmethyl)amino]-5-oxo-1,5-dihydro-4H-imidazol-4-ylidene}methyl]-1H-pyrrolo[2,3-b]pyridine-5-carbonitrile (5Z)-2-[(cyclopropylmethyl)amino]-5-[(5-phenyl-1H-pyrrolo[2,3-b]pyridin-3-yl)methylidene]-3,5-dihydro-4H-imidazol-4-one (5Z)-2-[(cyclopropylmethyl)amino]-5-{[5-(trifluoromethyl)-1H-pyrrolo[2,3-b]pyridin-3-yl]methylidene}-3,5-dihydro-4H-imidazol-4-one (5Z)-5-[(5-chloro-1H-pyrrolo[2,3-b]pyridin-3-yl)methylidene]-2-(methylsulphanyl)-3,5-dihydro-4H-imidazol-4-one (5Z)-2-butyl-5-[(5-chloro-1H-pyrrolo[2,3-b]pyridin-3-yl)methylidene]-3,5-dihydro-4H-imidazol-4-one (5Z)-2-(3-methylbutyl)-5-(1H-pyrrolo[2,3-b]pyridin-3-ylmethylidene)-3,5-dihydro-4H-imidazol-4-one (5Z)-2-cyclohexyl-5-(1H-pyrrolo[2,3-b]pyridin-3-ylmethylidene)-3,5-dihydro-4H-imidazol-4-one (5Z)-5-[(5-chloro-1H-pyrrolo[2,3-b]pyridin-3-yl)methylidene]-3-methyl-2-(tetrahydro-2H-pyran-4-yl)-3,5-dihydro-4H-imidazol-4-one (5Z)-5-[(5-chloro-1H-pyrrolo[2,3-b]pyridin-3-yl)methylidene]-3-methyl-2-(2-methylpropyl)-3,5-dihydro-4H-imidazol-4-one (5Z)-2-(cyclopropylmethyl)-5-(5-chloro-1H-pyrrolo[2,3-b]pyridin-3-ylmethylidene)-3,5-dihydro-4H-imidazol-4-one (5Z)-2-(1-methylethyl)-5-(5-chloro-1H-pyrrolo[2,3-b]pyridin-3-ylmethylidene)-3,5-dihydro-4H-imidazol-4-one (5Z)-2-[benzyl(methyl)amino]-5-[(5-chloro-1H-pyrrolo[2,3-b]pyridin-3-yl)methylidene]-3,5-dihydro-4H-imidazol-4-one (5Z)-5-[(5-chloro-1H-pyrrolo[2,3-b]pyridin-3-yl)methylidene]-2-[(2-methoxyethyl)(methyl)amino]-3,5-dihydro-4H-imidazol-4-one (5Z)-2-azepan-1-yl-5-[(5-chloro-1H-pyrrolo[2,3-b]pyridin-3-yl)methylidene]-3,5-dihydro-4H-imidazol-4-one (5Z)-5-[(5-chloro-1H-pyrrolo[2,3-b]pyridin-3-yl)methylidene]-2-piperidin-1-yl-3,5-dihydro-4H-imidazol-4-one (5Z)-5-[(5-chloro-1H-pyrrolo[2,3-b]pyridin-3-yl)methylidene]-2-[methyl(2-methylpropyl)amino]-3,5-dihydro-4H-imidazol-4-one (5Z)-5-[(5-bromo-1H-pyrrolo[2,3-b]pyridin-3-yl)methylidene]-2-[(cyclopropylmethyl)amino]-3,5-dihydro-4H-imidazol-4-one (5Z)-2-[(cyclopropylmethyl)amino]-5-[(5-methoxy-1H-pyrrolo[2,3-b]pyridin-3-yl)methylidene]-3,5-dihydro-4H-imidazol-4-one (5Z)-2-[(cyclopropylmethyl)amino]-5-[(5-fluoro-1H-pyrrolo[2,3-b]pyridin-3-yl)methylidene]-3,5-dihydro-4H-imidazol-4-one (5Z)-2-azepan-1-yl-5-[(5-fluoro-1H-pyrrolo[2,3-b]pyridin-3-yl)methylidene]-3,5-dihydro-4H-imidazol-4-one 3-[(Z)-{2-[(cyclopropylmethyl)amino]-5-oxo-1,5-dihydro-4H-imidazol-4-ylidene}methyl]-1H-pyrrolo[2,3-b]pyridine-5-carbonitrile said products of formula (I) being in all possible isomeric forms: racemates, enantiomers and diastereoisomers, as well as salts of addition of said products of formula (I) with pharmaceutically acceptable inorganic and organic acids or inorganic and organic bases.

The invention also relates to pharmaceutical compositions containing, as active principle, at least one of the products of formula (I) as defined above or a pharmaceutically acceptable salt of this product or a prodrug of this product and, if applicable, a pharmaceutically acceptable carrier.

The invention thus extends to pharmaceutical compositions containing, as active principle, at least one of the medicinal products as defined above.

Said pharmaceutical compositions of the present invention can also, if applicable, contain active principles of other antimitotic medicinal products such as notably those based on taxol, cisplatin, DNA intercalating agents and others.

These pharmaceutical compositions can be administered orally, parenterally or locally by topical application on the skin and the mucosae or by intravenous or intramuscular injection.

These compositions can be solid or liquid and can be in all the pharmaceutical forms commonly used in human medicine, for example plain or coated tablets, pills, lozenges, capsules, drops, granules, injectable preparations, ointments, creams or gels; they are prepared according to the usual methods. The active principle can be incorporated in them with the excipients usually employed in said pharmaceutical compositions, such as talc, gum arabic, lactose, starch, magnesium stearate, cocoa butter, aqueous or non-aqueous vehicles, fats of animal or vegetable origin, paraffinic derivatives, glycols, various wetting agents, dispersants or emulsifiers, preservatives.

The usual posology, which varies according to the product used, the subject treated and the disorder in question, can be for example from 0.05 to 5 g per day in an adult, or preferably from 0.1 to 2 g per day.

The present invention also relates to the use of the products of formula (I) as defined above or of pharmaceutically acceptable salts of these products for the preparation of a medicinal product intended to inhibit the activity of a protein kinase.

The present invention also relates to the use of products of formula (I) as defined above for the preparation of a medicinal product intended for the treatment or prevention of a disease characterized by disturbance of the activity of a protein kinase.

Said medicinal product can notably be intended for the treatment or prevention of a disease in a mammal.

The present invention also relates to the use as defined above in which the protein kinase is a serine-threonine protein kinase.

The present invention notably relates to the use defined above in which the protein kinase is Cdc7.

The present invention also relates to the use defined above in which the protein kinase is in a cell culture.

The present invention also relates to the use defined above in which the protein kinase is in a mammal.

The present invention relates in particular to the use of a product of formula (I) as defined above for the preparation of a medicinal product intended for the treatment or prevention of a disease selected from the following group: disorders of proliferation of blood vessels, fibrotic disorders, disorders of proliferation of mesangial cells, metabolic disorders, allergies, asthmas, thromboses, diseases of the nervous system, retinopathy, psoriasis, rheumatoid arthritis, diabetes, muscular degeneration and cancers.

The present invention relates more particularly to the use of a product of formula (I) as defined above for the preparation of a medicinal product intended for the treatment or prevention of a disease selected from the following group: disorders of proliferation of mesangial cells, psoriasis, rheumatoid arthritis, diabetes, muscular degeneration and cancers.

The present invention relates quite particularly to the use of a product of formula (I) as defined above for the preparation of a medicinal product intended for the prevention or treatment of diseases associated with uncontrolled cellular proliferation, for the preparation of a medicinal product intended for the treatment of diseases in oncology and notably intended for the treatment of cancers.

Among these cancers, we are notably interested in the treatment of solid tumours, and the treatment of cancers that are resistant to cytotoxic agents.

Among these cancers, we are notably interested in the treatment of cancers of the breast, stomach, ovaries, colon, lung, brain, larynx, lymphatic system, urogenital tract including bladder and prostate, cancers of the bones and of the pancreas, and quite particularly treatment of cancers of the breast, of the colon or of the lung.

The present invention also relates to the use of the products of formula (I) as defined above for the preparation of medicinal products intended for the chemotherapy of cancers.

Said medicinal products intended for the chemotherapy of cancers can be used alone or in combination.

The products of the present application can notably be administered alone or in combination with chemotherapy or radiotherapy or alternatively in combination for example with other therapeutic agents.

Said therapeutic agents can be antitumour agents that are currently used.

As kinase inhibitors, we may mention butyrolactone, flavopiridol and 2(2-hydroxyethyl-amino)-6-benzylamino-9-methylpurine, called olomucin.

The present invention relates in particular to the products of formula (I) as defined above as inhibitors of Cdc7.

The present invention relates quite particularly to the products of formula (I) which constitute Examples 1 to 99 of the present invention.

The 99 products that follow thus illustrate formula (I) of the present invention more precisely, though without limiting it.

In the preparation of the 99 products given as examples in the present application, the following devices were used:

$^1$H-NMR spectrum at 400 MHz on BRUKER AVANCE DRX-400 spectrometer with chemical shifts (δ in ppm), in the solvent dimethylsulphoxide-$d_6$ (DMSO-$d_6$) referenced at 2.50 ppm at a temperature of 303K.

$^1$H-NMR spectrum at 300 MHz on BRUKER AVANCE DPX-300 spectrometer with chemical shifts (δ in ppm), in the solvent dimethylsulphoxide-$d_6$ (DMSO-$d_6$) referenced at 2.50 ppm at a temperature of 303K.

LC-MS-DAD-ELSD analysis (MS: Waters ZQ; electrospray mode +/−; mass-to-charge ratio m/z=100-1200; LC: Agilent HP 1100; LC column: X Bridge, 18C Waters 3.0×50 mm-2.5 μm; LC furnace: 60° C.; flow rate of mobile phase: 1.1 ml/minute.

Eluents: A: Water+0.1% formic acid, B: acetonitrile with the following gradient:

| Time | A % | B % |
| --- | --- | --- |
| 0.0 | 95 | 5.0 |
| 5.0 | 5.0 | 100 |
| 5.5 | 5.0 | 100 |
| 6.5 | 95.0 | 5.0 |
| 7.0 | 95.0 | 5.0 |

DAD: wavelength considered λ = 210-400 nm
ELSD: Sedere SEDEX 85
SM-EI-CI-Direct injection-DCI analysis (EI = electron-impact ionization, CI: chemical ionization, DCI: desorption chemical ionization) (MS: Finnigan SSQ7000); energy of the electrons: 70 eV; mass-to-charge ratio m/z = 29-900; temperature of ionization source = 70° C.; reactant gas in CI: ammonia.

(1): Routine LC/MS analysis:
Mass detector: ZQ (Waters)
LC: column: X Bridge 18C Waters 3.0×50 mm−2.5 μm; flow=1.1 ml/minute.

Eluents: A: Water+0.1% formic acid, B: Acetonitrile with the following gradient:

| Time | A % | B % |
| --- | --- | --- |
| 0.0 | 95 | 5.0 |
| 5.0 | 5.0 | 100 |
| 5.5 | 5.0 | 100 |
| 6.5 | 95.0 | 5.0 |
| 7.0 | 95.0 | 5.0 |

DAD: wavelength considered λ = 200-400 nm
ELSD: Sedere SEDEX 85

(2): Microwaves: BIOTAGE INITIATOR MICROWAVE SYNTHESIZER

Maximum irradiation power 300 watts

It should be noted that in the examples described below, the compounds 1H-pyrrolo[2,3-b]pyridine-3-carbaldehydes (II) can be obtained from 1H-pyrrolo[2,3-b]pyridine derivatives by reaction with 1,3,5,7-tetraazatricyclo[3.3.1.1~3,7~]decane (A. Verbiscar J. Med. Chem. 1972, 15, 149) or by the Vilsmeier reaction (M-C Viaud et al. Heterocycles. 1999, 50, 1065).

EXAMPLE 1

(5Z)-5-(1H-pyrrolo[2,3-b]pyridin-3-ylmethylene)-2-thioxoimidazolidin-4-one (5Z)-5-(1H-pyrrolo[2,3-b]pyridin-3-ylmethylene)-2-thioxoimidazolidin-4-one can be prepared as follows:
Add 0.1 cm³ of piperidine and 400 mg of 2-thioxoimidazolidin-4-one to a suspension of 500 mg of 1H-pyrrolo[2,3-b]pyridine-3-carbaldehyde in 10 cm³ of ethanol. Reflux the reaction mixture
the solid goes into solution. After heating for thirty minutes, a precipitate forms. Turn off the heating and filter the reaction mixture at a temperature close to 25° C. 561 mg of (5Z)-5-(1H-pyrrolo[2,3-b]pyridin-3-ylmethylene)-2-thioxoimidazolidin-4-one is obtained in the form of orange powder with the following characteristics:
¹H-NMR spectrum at 400 MHz: 6.80 (s: 1H); 7.20 (dd, J=5 and 8 Hz: 1H); from 8.26 to 8.34 (m: 2H); 8.55 (s: 1H); from 11.7 to 12.2 (m spread out: 2H); from 12.3 to 12.6 (m spread out: 1H) Mass spectrum: LC-MS-DAD-ELSD: 243(−)=(M−H)(−); 245(+)=(M+H)(+)

EXAMPLE 2

(5Z)-5-[(4-chloro-1H-pyrrolo[2,3-b]pyridin-3-yl)methylene]-2-thioxoimidazolidin-4-one a) (5Z)-5-[(4-chloro-1H-pyrrolo[2,3-b]pyridin-3-yl)methylene]-2-thioxoimidazolidin-4-one can be prepared as in Example 1 but from 182 mg of 4-chloro-1H-pyrrolo[2,3-b]pyridine-3-carbaldehyde in 3 cm³ of ethanol, 117 mg of 2-thioxoimidazolidin-4-one and 0.1 cm³ of piperidine. After refluxing for two hours, 250 mg of a mixture containing 60% of (5Z)-5-[(4-chloro-1H-pyrrolo[2,3-b]pyridin-3-yl)methylene]-2-thioxoimidazolidin-4-one is obtained in the form of orange powder. The characteristics of the isomer (5Z) are as follows:
¹H-NMR spectrum at 400 MHz: 7.26 (s: 1H); 7.30 (m: 1H); 8.24 (d, J=5 Hz: 1H); 8.58 (s: 1 H); from 11.5 to 13.0 (m very broad: 3H)
Mass spectrum: LC-MS-DAD-ELSD: 243(−)=(M−H)(−); 245(+)=(M+H)(+)
b) 4-chloro-1H-pyrrolo[2,3-b]pyridine-3-carbaldehyde
4-chloro-1H-pyrrolo[2,3-b]pyridine-3-carbaldehyde can be prepared as follows:
Add 1.4 g of 1,3,5,7-tetraazatricyclo[3.3.1.1~3,7~]decane to a suspension of 1 g of 4-chloro-1H-pyrrolo[2,3-b]pyridine in a mixture of 7 cm³ of water and 3.5 cm³ of acid acetic. Reflux the reaction mixture for one hour and thirty minutes. On returning to a temperature close to 25° C., add water and ice. There is formation of a precipitate in the form of gum. Take up the latter in two times 20 cm³ of ethyl acetate. Combine the organic phases, wash with water, dry over magnesium sulphate, filter and concentrate to dryness at reduced pressure. Take up the residue in 5 cm³ of ethyl acetate. The precipitate obtained is filtered and dried at reduced pressure. 82 mg of 4-chloro-1H-pyrrolo[2,3-b]pyridine-3-carbaldehyde is obtained. The filtrate is concentrated to dryness at reduced pressure and after flash chromatography on a silica column [eluent: dichloromethane/methanol (gradient from 99/1 to 90/10 by volume)], 160 mg of 4-chloro-1H-pyrrolo[2,3-b]pyridine-3-carbaldehyde is obtained with the following characteristics:
LC/MS (1): Retention time: 2.69 min
Mass spectrum (1): (ES+): m/z=181 [MH+]
c) 4-chloro-1H-pyrrolo[2,3-b]pyridine can be prepared as described in C. Thibault et al.: Org. Lett. 2003, 5(26); 5023.

EXAMPLE 3

(5Z)-5-[(5-chloro-1H-pyrrolo[2,3-b]pyridin-3-yl)methylene]-2-thioxoimidazolidin-4-one a) (5Z)-5-[(5-chloro-1H-pyrrolo[2,3-b]pyridin-3-yl)methylene]-2-thioxoimidazolidin-4-one can be prepared as in Example 1 but from 400 mg of 5-chloro-1H-pyrrolo[2,3-b]pyridine-3-carbaldehyde in 15 cm³ of ethanol, 257 mg of 2-thioxoimidazolidin-4-one and 0.22 cm³ of piperidine. After refluxing for two hours, 320 mg of (5Z)-5-[(5-chloro-1H-pyrrolo[2,3-b]pyridin-3-yl)methylene]-2-thioxoimidazolidin-4-one is obtained in the form of orange powder with the following characteristics:
¹H-NMR spectrum at 400 MHz: 6.79 (s: 1H); 8.29 (d, J=3 Hz: 1H); 8.54 (d, J=3 Hz: 1H); 8.57 (s: 1H); from 7.00 to 8.30 (m very broad: 2H); from 11.4 to 12.5 (m spread out: 1H)
Mass spectrum: LC-MS-DAD-ELSD: 279(+)=(M+H)(+) (1 chlorine atom Cl present)
b) 5-chloro-1H-pyrrolo[2,3-b]pyridine-3-carbaldehyde can be prepared as described in WO05/95400.

EXAMPLE 4

(5Z)-5-[(6-chloro-1H-pyrrolo[2,3-b]pyridin-3-yl)methylene]-2-thioxoimidazolidin-4-one a) (5Z)-5-[(6-chloro-1H-pyrrolo[2,3-b]pyridin-3-yl)methylene]-2-thioxoimidazolidin-4-one can be prepared as in Example 1 but from 140 mg of 6-chloro-1H-pyrrolo[2,3-b]pyridine-3-carbaldehyde in 5 cm³ of ethanol, 90 mg of 2-thioxoimidazolidin-4-one and 0.08 cm³ of piperidine. After refluxing for two hours, 180 mg of (5Z)-5-[(6-chloro-1H-pyrrolo[2,3-b]pyridin-3-yl)methylene]-2-thioxoimidazolidin-4-one is obtained in the form of a powder with the following characteristics:
¹H-NMR spectrum at 400 MHz: 6.57 (s: 1H); 7.20 (d, J=8 Hz: 1H); 8.40 (s: 1H); 8.49 (d, J=8 Hz: 1H); from 9.40 to 10.5 (m spread out: 3H)
Mass spectrum: LC-MS-DAD-ELSD: 279(+)=(M+H)(+) (1 chlorine atom Cl present)
b) 6-chloro-1H-pyrrolo[2,3-b]pyridine-3-carbaldehyde can be prepared as described in WO01/98299.

EXAMPLE 5

(5Z)-5-[(2-methyl-1H-pyrrolo[2,3-b]pyridin-3-yl)methylene]-2-thioxoimidazolidin-4-one a) (5Z)-5-[(2-methyl-1H-pyrrolo[2,3-b]pyridin-3-yl)methylene]-2-thioxoimidazolidin-4-one can be prepared as in Example 1 but from 400 mg of 2-methyl-1H-pyrrolo[2,3-b]pyridine-3-carbaldehyde in 15 cm³ of ethanol, 290 mg of 2-thioxoimidazolidin-4-one and 0.25 cm³ of piperidine. After four hours of reflux, 463 mg of a mixture containing 65% of (5Z)-5-[(2-methyl-1H-pyrrolo[2,3-b]pyridin-3-yl)methylene]-2-thioxoimidazolidin-4-one is obtained in the form of orange powder which will be used as such for the next stage, and has the following characteristics:

$^1$H-NMR spectrum at 400 MHz: 2.45 (s: 3H); 6.70 (s broad: 1H); 7.12 (dd, J=5 and 8 Hz: 1H); 7.88 (m: 1H); 8.20 (dd, J=1.5 and 5 Hz: 1H); 11.55 (s broad: 1H); from 12.0 to 12.2 (m spread out: 2H)

Mass spectrum: LC-MS-DAD-ELSD: mixture containing the expected structure 259(+)=(M+H) (+)

b) 2-methyl-1H-pyrrolo[2,3-b]pyridine-3-carbaldehyde 2-methyl-1H-pyrrolo[2,3-b]pyridine-3-carbaldehyde can be prepared as in Example 2 but from 835 mg of 2-methyl-1H-pyrrolo[2,3-b]pyridine in a mixture of 5.3 cm³ of water and 1.6 cm³ of acid acetic and 1.32 g of 1,3,5,7-tetraazatricyclo[3.3.1.1~3,7~]decane. 580 mg of a mixture containing 60% of 2-methyl-1H-pyrrolo[2,3-b]pyridine-3-carbaldehyde is obtained in the form of a beige solid. The characteristics for 2-methyl-1H-pyrrolo[2,3-b]pyridine-3-carbaldehyde are as follows:

LC/MS (1): Retention time: 1.7 min
Mass spectrum (1): (ES+): m/z=161 [MH+]

c) 2-methyl-1H-pyrrolo[2,3-b]pyridine 2-methyl-1H-pyrrolo[2,3-b]pyridine can be prepared as follows: Add 8.2 g of potassium hydroxide to a solution of 2.2 g of 2-methyl-1-[(4-methylphenyl)sulphonyl]-1H-pyrrolo[2,3-b]pyridine in 70 cm³ of methanol. Stir the reaction mixture at a temperature close to 20° C. for five hours then reflux for five hours. Then concentrate the medium (or mixture) to half at reduced pressure: a precipitate forms. The solid is filtered and the filtrate is concentrated to dryness at reduced pressure, taken up in 100 cm³ of water, then once 100 cm³ and twice 50 cm³ of ethyl acetate. The combined organic phases are dried over magnesium sulphate, filtered and concentrated to dryness at reduced pressure. After flash chromatography on a silica column [eluent: heptane/ethyl acetate (gradient from 80/20 to 40/60 by volume)], 835 mg of 2-methyl-1H-pyrrolo[2,3-b]pyridine is obtained in the form of a beige solid with the following characteristics:

Rf TLC silica=0.49 [eluent: heptane/ethyl acetate (60/40 by volume)]
Mass spectrum: LC-MS-DAD-ELSD: 133(+)=(M+H)(+)
SM-EI: 132(+)=M(+)

d) 2-methyl-1-[(4-methylphenyl)sulphonyl]-1H-pyrrolo[2,3-b]pyridine.

2-methyl-1-[(4-methylphenyl)sulphonyl]-1H-pyrrolo[2,3-b]pyridine can be prepared as follows:

Cool a solution of 2 g of 1-[(4-methylphenyl)sulphonyl]-1H-pyrrolo[2,3-b]pyridine in 20 cm³ of tetrahydrofuran to a temperature close to −70° C. using a dry ice/acetone bath. At this temperature and under argon, add dropwise 9.2 cm³ of a 1.6M solution of n-butyllithium in hexane. Stir the reaction medium (or mixture) at this temperature for thirty minutes then add 1.37 cm³ of methyl iodide. Stir the mixture under argon at a temperature close to −70° C. for three hours. After heating the mixture to a temperature close to 0° C., add 20 cm³ of water, then allow the temperature to approach 20° C. and extract with three times 50 cm³ of ethyl acetate. Wash the combined organic phases with a saturated aqueous solution of sodium chloride, dry over magnesium sulphate, filter and concentrate to dryness at reduced pressure. 2.2 g of 2-methyl-1-[(4-methylphenyl)sulphonyl]-1H-pyrrolo[2,3-b]pyridine is obtained in the form of a beige powder with the following characteristics:

$^1$H-NMR spectrum at 400 MHz: 2.30 (s: 3H); 2.32 (s: 3H); 2.69 (s broad: 3H); 6.59 (s broad: 1H); 7.15 (s broad: 1H); 7.17 (dd, J=5 and 8 Hz: 1H); 7.26 (d broad, J=8 Hz: 1H); 7.90 (dd, J=2 and 8 Hz: 1H); 7.97 (d, J=8 Hz: 1H); 8.08 (dd, J=2 and 5 Hz: 1H)

Mass spectrum: LC-MS-DAD-ELSD: 301(+)=(M+H) (+); 299(−)=(M−H) (−)

e) 1-[(4-methylphenyl)sulphonyl]-1H-pyrrolo[2,3-b]pyridine 1-[(4-methylphenyl)sulphonyl]-1H-pyrrolo[2,3-b]pyridine can be prepared as follows:

Introduce, i.e. add, 100 mg of N,N,N-tributylbutane-1-ammonium hydrogen sulphate and 8.75 g of 4-methylbenzenesulphonyl chloride to a solution of 4.72 g of 1H-pyrrolo[2,3-b]pyridine in 110 cm³ of toluene. To the mixture cooled to 0° C., add a solution of 20.8 g of sodium hydroxide in 110 cm³ of water. Stir the reaction mixture under argon at a temperature close to 20° C. for four hours then add 100 cm³ of water. Extract the resultant mixture with 200 cm³ then 100 cm³ of ethyl acetate. Wash the combined organic phases with a saturated aqueous solution of sodium chloride, dry over magnesium sulphate, filter and concentrate to dryness at reduced pressure. 10.9 g of 1-[(4-methylphenyl)sulphonyl]-1H-pyrrolo[2,3-b]pyridine is obtained in the form of a white powder with the following characteristics:

Rf TLC silica=0.34 [eluent: heptane/ethyl acetate (70/30 by volume)]
Mass spectrum: LC-MS-DAD-ELSD: 273(+)=(M+H)(+) 295(+)=(M+Na)(+)

EXAMPLE 6

(5Z)-3-methyl-5-(1H-pyrrolo[2,3-b]pyridin-3-ylmethylene)-2-thioxoimidazolidin-4-one (5Z)-3-methyl-5-(1H-pyrrolo[2,3-b]pyridin-3-ylmethylene)-2-thioxoimidazolidin-4-one can be prepared as in Example 1 but from 225 mg of 1H-pyrrolo[2,3-b]pyridine-3-carbaldehyde in 10 cm³ of ethanol, 200 mg of 3-methyl-2-thioxoimidazolidin-4-one and 0.061 cm³ of piperidine. After refluxing for five hours, 271 mg of a mixture containing 85% of the isomer (5Z)-3-methyl-5-(1H-pyrrolo[2,3-b]pyridin-3-ylmethylene)-2-thioxoimidazolidin-4-one and 15% of the isomer (5E) is obtained in the form of an orange-yellow powder. The characteristics of the isomer 5Z are as follows:

$^1$H-NMR spectrum at 400 MHz: 3.21 (s: 3H); 6.96 (s: 1H); 7.20 (dd, J=5 and 8 Hz: 1H); from 8.27 to 8.37 (m: 2H); 8.59 (d, J=3 Hz: 1H); 12.05 (s broad: 1H); 12.5 (s broad: 1H)

Mass spectrum: LC-MS-DAD-ELSD: 257(−)=(M−H)(−); 259(+)=(M+H)(+)

EXAMPLE 7

(5Z)-2-[(cyclopropylmethyl)amino]-5-(1H-pyrrolo[2,3-b]pyridin-3-ylmethylene)-3,5-dihydro-4H-imidazol-4-one (5Z)-2-[(cyclopropylmethyl)amino]-5-(1H-pyrrolo[2,3-b]pyridin-3-ylmethylene)-3,5-dihydro-4H-imidazol-4-one can be prepared as follows:

Put 100 mg of (5Z)-5-(1H-pyrrolo[2,3-b]pyridin-3-ylmethylene)-2-thioxoimidazolidin-4-one, 1 cm³ of ethanol and 290 mg of 1-cyclopropylmethanamine in a microwave oven reactor. Close the reactor hermetically and irradiate the mixture with microwave radiation for twenty minutes at a temperature of 140° C., then thirty minutes at a temperature of 150° C. On returning to a temperature close to 20° C., the precipitate that has formed is filtered, washed with ethanol and dried at reduced pressure. 40 mg of (5Z)-2-[(cyclopropylmethyl)amino]-5-(1H-pyrrolo[2,3-b]pyridin-3-ylmethylene)-3,5-dihydro-4H-imidazol-4-one is obtained in the form of a yellow powder with the following characteristics:

$^1$H-NMR spectrum at 400 MHz: 0.30 (m: 2H); 0.48 (m: 2H); 1.13 (m: 1H); 3.23 (t broad, J=6.5 Hz: 2H); 6.61 (s broad: 1H); 7.11 (d, J=5 Hz: 1H); 7.24 (m: 1H); from 8.15 to 8.30 (m: 2H); 8.55 (d broad, J=7 Hz: 1H); from 9.70 to 10.7 (m spread out: 1H); 11.6 (m spread out: 1H)

Mass spectrum: SM-EI: 281(+)=M(+)

EXAMPLE 8

(5Z)-5-[(4-chloro-1H-pyrrolo[2,3-b]pyridin-3-yl) methylene]-2-[(cyclopropylmethyl)amino]-3,5-dihydro-4H-imidazol-4-one (5Z)-5-[(4-chloro-1H-pyrrolo[2,3-b]pyridin-3-yl)methylene]-2-[(cyclopropylmethyl)amino]-3,5-dihydro-4H-imidazol-4-one can be prepared as in Example 7 but from 190 mg of (5Z)-5-[(4-chloro-1H-pyrrolo[2,3-b]pyridin-3-yl) methylene]-2-thioxoimidazolidin-4-one, 4 cm$^3$ of ethanol and 485 mg of 1-cyclopropylmethanamine. After one hour at a temperature of 145° C. under microwave irradiation and thirty minutes at a temperature of 150° C., 100 mg of (5Z)-5-[(4-chloro-1H-pyrrolo[2,3-b]pyridin-3-yl)methylene]-2-[(cyclopropylmethyl)amino]-3,5-dihydro-4H-imidazol-4-one is obtained in the form of orange powder with the following characteristics:

$^1$H-NMR spectrum at 400 MHz: 0.28 (m: 2H); 0.48 (m: 2H); 1.12 (m: 1H); 3.22 (m partially masked: 2H); 7.10 (s broad: 1H); 7.22 (d, J=5 Hz: 1H); 7.37 (m: 1H); 8.18 (d, J=5 Hz: 1H); 8.58 (s broad: 1H); from 10.25 to 10.8 (m spread out: 1H); from 12.0 to 12.6 (m spread out: 1H)

Mass spectrum: LC-MS-DAD-ELSD: 314(−)=(M−H)(−); 316(+)=(M+H)(+) (1 chlorine atom Cl present)

EXAMPLE 9

(5Z)-5-[(5-chloro-1H-pyrrolo[2,3-b]pyridin-3-yl) methylene]-2-[(cyclopropylmethyl)amino]-3,5-dihydro-4H-imidazol-4-one (5Z)-5-[(5-chloro-1H-pyrrolo[2,3-b]pyridin-3-yl)methylene]-2-[(cyclopropylmethyl)amino]-3,5-dihydro-4H-imidazol-4-one can be prepared as in Example 7 but from 200 mg of (5Z)-5-[(5-chloro-1H-pyrrolo[2,3-b]pyridin-3-yl)methylene]-2-thioxoimidazolidin-4-one, 4 cm$^3$ of ethanol and 511 mg of 1-cyclopropylmethanamine, after thirty minutes at a temperature of 145° C. under microwave irradiation. The medium (or mixture) is then concentrated, and purified by flash chromatography on a silica column [eluent: dichloromethane/methanol (gradient from 95/5 to 70/30 by volume)]. 20 mg of (5Z)-5-[(5-chloro-1H-pyrrolo[2,3-b]pyridin-3-yl)methylene]-2-[(cyclopropylmethyl)amino]-3,5-dihydro-4H-imidazol-4-one is obtained in the form of a pale yellow powder with the following characteristics:

$^1$H-NMR spectrum at 400 MHz: 0.30 (m: 2H); 0.48 (m: 2H); 1.16 (m: 1H); 3.24 (m partially masked: 2H); 6.58 (s: 1H); 7.25 (m: 1H); 8.16 (s broad: 1H); 8.22 (s broad: 1H); 9.15 (s broad: 1H); from 10.25 to 10.7 (m spread out: 1H); from 11.9 to 12.4 (m spread out: 1H)

Mass spectrum: LC-MS-DAD-ELSD: 314(−)=(M−H)(−); 316(+)=(M+H)(+) (1 chlorine atom Cl present)

EXAMPLE 10

(5Z)-5-[(6-chloro-1H-pyrrolo[2,3-b]pyridin-3-yl) methylene]-2-[(cyclopropylmethyl)amino]-3,5-dihydro-4H-imidazol-4-one (5Z)-5-[(6-chloro-1H-pyrrolo[2,3-b]pyridin-3-yl)methylene]-2-[(cyclopropylmethyl)amino]-3,5-dihydro-4H-imidazol-4-one can be prepared as in Example 7, but from 150 mg of (5Z)-5-[(6-chloro-1H-pyrrolo[2,3-b]pyridin-3-yl) methylene]-2-thioxoimidazolidin-4-one, 3.75 cm$^3$ of ethanol and 383 mg of 1-cyclopropylmethanamine. After fifteen minutes at a temperature of 140° C., then thirty minutes at a temperature of 150° C. under microwave irradiation, 55 mg of (5Z)-5-[(6-chloro-1H-pyrrolo[2,3-b] pyridin-3-yl)methylene]-2-[(cyclopropylmethyl)amino]-3,5-dihydro-4H-imidazol-4-one is obtained in the form of a pale yellow powder with the following characteristics:

$^1$H-NMR spectrum at 400 MHz: 0.30 (m: 2H); 0.48 (m: 2H); 1.12 (m: 1H); 3.24 (t, J=6.5 Hz: 2H); 6.57 (s: 1H); 7.16 (d, J=8 Hz: 1H); from 7.20 to 7.35 (m spread out: 1H); 8.18 (m: 1H); 8.73 (m: 1H); from 9.80 to 10.70 (m very broad: 1H); from 11.5 to 12.3 (m very broad: 1H)

Mass spectrum: LC-MS-DAD-ELSD: 316(+)=(M+H)(+) (1 chlorine atom Cl present)

EXAMPLE 11

(5Z)-2-[(cyclopropylmethyl)amino]-5-[(2-methyl-1H-pyrrolo[2,3-b]pyridin-3-yl)methylene]-3,5-dihydro-4H-imidazol-4-one (5Z)-2-[(cyclopropylmethyl)amino]-5-[(2-methyl-1H-pyrrolo[2,3-b]pyridin-3-yl)methylene]-3,5-dihydro-4H-imidazol-4-one can be prepared as in Example 7, but from 200 mg of a mixture containing 65% of (5Z)-5-[(2-methyl-1H-pyrrolo[2,3-b]pyridin-3-yl)methylene]-2-thioxoimidazolidin-4-one, 2 cm$^3$ of ethanol and 551 mg of 1-cyclopropylmethanamine, after fifteen minutes at a temperature of 140° C. and fifteen minutes at 145° C. under microwave irradiation. The mixture obtained is then purified by flash chromatography on a silica column [eluent: dichloromethane/methanol (gradient from 98/2 to 90/10 by volume)]. 35 mg of (5Z)-2-[(cyclopropylmethyl)amino]-5-[(2-methyl-1H-pyrrolo[2,3-b]pyridin-3-yl)methylene]-3, 5-dihydro-4H-imidazol-4-one is obtained in the form of a pale yellow powder with the following characteristics:

$^1$H-NMR spectrum at 400 MHz: 0.29 (m: 2H); 0.47 (m: 2H); 1.13 (m: 1H); 2.50 (s partially masked: 3H); 3.23 (t, J=6.5 Hz: 2H); 6.48 (s: 1H); 7.00 (m: 1H); 7.08 (m: 1H); 8.10 (d broad, J=4 Hz: 1H); 9.42 (d, J=8 Hz: 1H); from 10.3 to 10.6 (m spread out: 1H); 11.8 (s broad: 1H)

Mass spectrum: LC-MS-DAD-ELSD: 294(−)=(M−H)(−); 296(+)=(M+H)(+)

EXAMPLE 12

(5Z)-2-[(cyclopropylmethyl)amino]-3-methyl-5-(1H-pyrrolo[2,3-b]pyridin-3-ylmethylene)-3,5-dihydro-4H-imidazol-4-one (5Z)-2-[(cyclopropylmethyl)amino]-3-methyl-5-(1H-pyrrolo[2,3-b]pyridin-3-ylmethylene)-3,5-dihydro-4H-imidazol-4-one can be prepared as in Example 7, but from 100 mg of (5Z)-3-methyl-5-(1H-pyrrolo[2,3-b]pyridin-3-ylmethylene)-2-thioxoimidazolidin-4-one, 4 cm$^3$ of ethanol and 275 mg of 1-cyclopropylmethanamine. After fifteen minutes at a temperature of 140° C., forty minutes at 150° C. and forty-five minutes at 160° C. under microwave irradiation, 39 mg of (5Z)-2-[(cyclopropylmethyl)amino]-3-methyl-5-(1H-pyrrolo[2,3-b]pyridin-3-ylmethylene)-3,5-dihydro-4H-imidazol-4-one is obtained in the form of a yellow powder with the following characteristics:

$^1$H-NMR spectrum at 400 MHz: 0.35 (m: 2H); 0.51 (m: 2H); 1.22 (m: 1H); 3.07 (s: 3H); 3.33 (t, J=6.5 Hz: 2H); 6.74 (s: 1H); 7.11 (dd, J=5 and 8 Hz: 1H); 7.55 (t, J=6.5 Hz: 1H); from 8.20 to 8.27 (m: 2H); 8.61 (d, J=8 Hz: 1H); 11.9 (s broad: 1H)

Mass spectrum: LC-MS-DAD-ELSD: 294(−)=(M−H)(−); 296(+)=(M+H)(+)

EXAMPLE 13

(5Z)-2-butyl-5-[(1H-pyrrolo[2,3-b]pyridin-3-yl)methylidene]-3,5-dihydro-4H-imidazol-4-one Preparation A of Example 13

(5Z)-2-butyl-5-(1H-pyrrolo[2,3-b]pyridin-3-ylmethylene)-3,5-dihydro-4H-imidazol-4-one (5Z)-2-butyl-5-(1H-pyrrolo[2,3-b]pyridin-3-ylmethylene)-3,5-dihydro-4H-imidazol-4-one can be prepared as in Example 1, but adding 0.15 cm$^3$ of piperidine and 324 mg of 2-butyl-3,5-dihydro-4H-imidazol-4-one (prepared for example according to J. Org. Chem. 1999, 64, 8084-8089) to 198 mg of 1H-pyrrolo[2,3-b]pyridine-3-carbaldehyde in 15 cm$^3$ of ethanol. Reflux the reaction mixture for three hours and concentrate the mixture under vacuum. On adding a little ethanol, a yellow solid forms, which is filtered, washed with 3 cm$^3$ of dichloromethane, and dried under vacuum to obtain 65 mg. This solid is combined with the 66 mg of solid obtained in an identical reaction on 245 mg of 1H-pyrrolo[2,3-b]pyridine-3-carbaldehyde. The solids are taken up in 20 cm$^3$ of water and extracted with two times 30 cm$^3$ of ethyl acetate. The organic phases are dried over magnesium sulphate, filtered and concentrated at reduced pressure, obtaining 88 mg of (5Z)-2-butyl-5-(1H-pyrrolo[2,3-b]pyridin-3-ylmethylene)-3,5-dihydro-4H-imidazol-4-one in the form of a yellow powder with the following characteristics:

$^1$H-NMR spectrum at 400 MHz: 0.95 (t, J=7.5 Hz, 3H); 1.40 (m, 2H); 1.71 (m, 2H); 2.54 (t, J=7.5 Hz, 2H); 7.16 (s, 1H); 7.18 (dd, J=5.0 and 8.0 Hz, 1H); 8.28 (dd, J=1.5 and 5.0 Hz, 1H); 8.34 (s, 1H); 8.92 (d broad, J=8.0 Hz, 1H); 11.1 (m spread out, 1H); 12.4 (m spread out, 1H)

Preparation B of Example 13

(5Z)-2-butyl-5-[(1H-pyrrolo[2,3-b]pyridin-3-yl)methylidene]-3,5-dihydro-4H-imidazol-4-one a) (5Z)-2-butyl-5-[(1H-pyrrolo[2,3-b]pyridin-3-yl)methylidene]-3,5-dihydro-4H-imidazol-4-one can be prepared as follows:

A mixture of 0.32 g of raw 2-butyl-3,5-dihydro-4H-imidazol-4-one, 0.2 g of 1H-pyrrolo[2,3-b]pyridine-3-carbaldehyde, 0.14 cm$^3$ of piperidine and 15 cm$^3$ of ethanol is refluxed for four hours. The yellow solid is filtered, washed with a little methylene chloride then dried under vacuum to obtain 65 mg of (5Z)-2-butyl-5-[(1H-pyrrolo[2,3-b]pyridin-3-yl)methylidene]-3,5-dihydro-4H-imidazol-4-one in the form of a yellow powder with the following characteristics:

$^1$H-NMR spectrum at 400 MHz: 0.95 (t, J=7.5 Hz, 3H); 1.40 (m, 2H); 1.71 (m, 2H); 2.54 (t, J=7.5 Hz, 2H); 7.17 (s, 1H); 7.20 (dd, J=5.0 and 8.0 Hz, 1H); 8.29 (dd, J=1.5 and 5.0 Hz, 1H); 8.34 (s, 1H); 8.92 (d broad, J=8.0 Hz, 1H); 11.1 (m spread out, 1H); 12.4 (m spread out, 1H).

HPLC-MS-DAD-ELSD: 269(+)=(M+H)(+); 267(−)=(M−H)(−).

b) 2-butyl-3,5-dihydro-4H-imidazol-4-one can be prepared as follows:

A solution of 63 mg of sodium hydroxide in 2 cm$^3$ of ethanol is added slowly to 0.2 g of methyl glycinate hydrochloride at −10° C. After 5 min, a solution of 0.18 g of methyl pentanimidoate in 5 cm$^3$ of toluene is added and the mixture is stirred at room temperature for 20 min. The pH is then adjusted to pH 7 with a solution of 1M HCl. The mixture obtained is concentrated under vacuum at room temperature. The residue is taken up in dichloromethane and the insoluble solid is filtered. Evaporation of the filtrate gives 0.32 g of 2-butyl-3,5-dihydro-4H-imidazol-4-one.

c) Methyl pentanimidoate can be prepared as follows:

Slowly add a 6M solution of potassium hydroxide (10.6 cm$^3$) to a solution of 0.3 g of methyl pentanimidoate hydrochloride in 5 cm$^3$ of ether at −10° C. Stir the mixture for 10 min then extract with ether (2×20 cm$^3$). Wash the organic phases with water (20 cm$^3$), dry over magnesium sulphate and concentrate under vacuum to obtain 179 mg of methyl pentanimidoate.

d) Methyl pentanimidoate hydrochloride can be prepared as follows:

Gaseous hydrogen chloride is bubbled for 30 min in a solution of 5 cm$^3$ of butane carbonitrile in a mixture of methanol (2.1 cm$^3$) and ether (5 cm$^3$), cooled to −10° C. Allow the temperature to rise to 0° C. and put the reaction mixture in a refrigerator overnight. On concentrating the solution, 6.9 g of methyl pentanimidoate hydrochloride is obtained in the form of a white solid.

UPLC-MS-DAD-ELSD analysis (MS=Quattro Premier XE Waters; electrospray +/−; mass-to-charge ratio m/z=100-1100; UPLC Waters; Acquity UPLC BeH C18 1.7 μm column.

3 mm, 50 mm; furnace UPLC=70° C., flow=0.7 ml/minute.

Eluents: A=water+0.1% formic acid, B=acetonitrile+0.1% formic acid with the gradient:

| Time | A % | B % |
| --- | --- | --- |
| 0 | 95 | 5 |
| 5 | 0 | 100 |
| 5.5 | 95 | 5 |
| 6.0 | 95 | 5 |

DAD wavelength considered λ = 210-400 nm
ELSD: Sedere SEDEX 85; spraying temperature = 35° C.; spraying pressure = 3.7 bar

EXAMPLE 14

(5Z)-5-[(5-bromo-1H-pyrrolo[2,3-b]pyridin-3-yl)methylene]-2-thioxoimidazolidin-4-one a) (5Z)-5-[(5-bromo-1H-pyrrolo[2,3-b]pyridin-3-yl)methylene]-2-thioxoimidazolidin-4-one can be prepared as in Example 1 but from 655 mg of 5-bromo-1H-pyrrolo[2,3-b]pyridine-3-carbaldehyde in 6 cm$^3$ of ethanol, 340 mg of 2-thioxoimidazolidin-4-one and 0.28 cm$^3$ of piperidine. After refluxing for two hours, 700 mg of (5Z)-5-[(5-bromo-1H-pyrrolo[2,3-b]pyridin-3-yl)methylene]-2- thioxoimidazolidin-4-one is obtained in the form of orange powder with the following characteristics:

¹H-NMR spectrum at 400 MHz: 6.82 (s, 1H); 8.37 (d, J=2.0 Hz, 1H); 8.57 (s, 1H); 8.64 (d, J=2.0 Hz, 1H); from 11.6 to 12.3 (m very broad, 2H); 12.6 (m spread out, 1H).

Mass spectrum: HPLC-MS-DAD-ELSD: 323(+)=(M+H)(+); 321(−) (M−H)(−) (1 bromine atom Br present).

b) 5-bromo-1H-pyrrolo[2,3-b]pyridine-3-carbaldehyde can be prepared as follows:

Add, at 0° C., 0.93 g of 5-bromo-1H-pyrrolo[2,3-b]pyridine to a suspension of 3.35 g of aluminium chloride in 50 cm³ of dichloromethane. Stir the reaction mixture for 15 minutes, then add dropwise 1.4 cm³ of dichloro(methoxy)methane. Stir the reaction mixture for three hours at 0° C., then dilute at 0° C. by adding 5 cm³ of methanol. Pour the mixture obtained into a mixture of 100 cm³ of ice water, then adjust to basic pH by adding 5M sodium hydroxide. Separate the phases, and wash the dichloromethane phase with water, then dry over sodium sulphate. Extract the aqueous phase again with two times 100 cm³ of ethyl acetate. Combine the two extracts, wash with water, dry over sodium sulphate and combine with the dichloromethane organic phase above. After concentration under vacuum, 0.61 g of 5-bromo-1H-pyrrolo[2,3-b]pyridine-3-carbaldehyde is obtained in the form of ochre powder with the following characteristics:

¹H-NMR spectrum at 400 MHz: 8.44 (d, J=2 Hz, 1H); 8.51 (m, 2H); 9.92 (s, 1H).

LC-MS (1): retention time: 3.08 min, LC-MS-DAD-ELSD: 223(−)=(M−H)(−); 225(+)=(M+H)(+) (1 Br present).

c) 5-bromo-1H-pyrrolo[2,3-b]pyridine can be prepared as described in D. Mazéas et al.: Heterocycles. 1999, 50(2); 1065-1080.

EXAMPLE 15

(5Z)-5-[(5-methoxy-1H-pyrrolo[2,3-b]pyridin-3-yl)methylene]-2-thioxoimidazolidin-4-one a) (5Z)-5-[(5-methoxy-1H-pyrrolo[2,3-b]pyridin-3-yl)methylene]-2-thioxoimidazolidin-4-one can be prepared as in Example 1 but from 160 mg of 5-methoxy-1H-pyrrolo[2,3-b]pyridine-3-carbaldehyde in 4 cm³ of ethanol, 110 mg of 2-thioxoimidazolidin-4-one and 0.09 cm³ of piperidine. After refluxing for 2.5 hours, 220 mg of (5Z)-5-[(5-methoxy-1H-pyrrolo[2,3-b]pyridin-3-yl)methylene]-2-thioxoimidazolidin-4-one is obtained in the form of orange powder with the following characteristics:

¹H-NMR spectrum at 400 MHz: 3.87 (s, 3H); 6.86 (s, 1H); 7.95 (d, J=2.5 Hz, 1H); 8.03 (d, J=2.5 Hz, 1H); 8.50 (s, 1H); 11.84 (s broad, 1H); 12.30 (s broad, 1H).

LC-MS (1): retention time 2.60 min, LC-MS-DAD-ELSD: 273(−)=(M−H)(−); 275 (+)=(M+H)(+).

b) 5-methoxy-1H-pyrrolo[2,3-b]pyridine-3-carbaldehyde can be prepared as described in D. Mazéas et al.: Heterocycles. 1999, 50(2); 1065-1080.

EXAMPLE 16

(5Z)-5-[(5-phenyl-1H-pyrrolo[2,3-b]pyridin-3-yl)methylene]-2-thioxoimidazolidin-4-one a) (5Z)-5-[(5-phenyl-1H-pyrrolo[2,3-b]pyridin-3-yl)methylene]-2-thioxoimidazolidin-4-one can be prepared as in Example 1 but from 135 mg of 5-phenyl-1H-pyrrolo[2,3-b]pyridine-3-carbaldehyde in 3 cm³ of ethanol, 70 mg of 2-thioxoimidazolidin-4-one and 0.06 cm³ of piperidine. After refluxing for 2.5 hours, 180 mg of (5Z)-5-[(5-phenyl-1H-pyrrolo[2,3-b]pyridin-3-yl)methylene]-2-thioxoimidazolidin-4-one is obtained in the form of orange powder with the following physical characteristics:

Melting point: 265-270° C.

¹H-NMR spectrum at 400 MHz: 6.84 (s, 1H); 7.38 (t, J=7.5 Hz, 1H); 7.49 (t, J=7.5 Hz, 2H); 7.82 (d, J=7.5 Hz, 2H); 8.52 (s, 1H); 8.61 (d, J=2.0 Hz, 1H); 8.68 (d, J=2.0 Hz, 1H) from 10.0 to 11.5 (m very broad, 3H).

LC-MS (1): retention time 3.49 min; LC-MS-DAD-ELSD: 319(−)=(M−H)(−); 321(+)=(M+H)(+).

b) 5-phenyl-1H-pyrrolo[2,3-b]pyridine-3-carbaldehyde can be prepared as follows:

Put 500 mg of 5-bromo-1H-pyrrolo[2,3-b]pyridine-3-carbaldehyde, 13 cm³ of dioxan, 3.7 cm³ of water, 2.9 g of caesium carbonate, 340 mg of phenylboronic acid, and 160 mg of 1,1'-bis(diphenylphosphino)ferrocene-dichloropalladium(II) in a microwave tube. Irradiate the reaction mixture with microwaves for thirty minutes at 140° C. After cooling, pour the reaction mixture into 50 cm³ of water. Extract the mixture obtained with two times 50 cm³ of ethyl acetate. Dry the combined organic phases over sodium sulphate, then reduce to dryness under vacuum. The residue obtained is purified by flash chromatography on a silica column with a dichloromethane/ethyl acetate eluent (dichloromethane/ethyl acetate gradient of 90/10 to 50/50 by volume) to give 377 mg of 5-phenyl-1H-pyrrolo[2,3-b]pyridine-3-carbaldehyde with the following physical characteristics:

¹H-NMR spectrum at 400 MHz: 7.41 (tt, J=1 and 7.4 Hz, 1H); 7.52 (t, J=7.4 Hz, 2H); 7.73 (d, J=7.4 Hz, 2H); 8.51 (s, 1H); 8.59 (d, J=2.3 Hz, 1H); 8.66 (d, J=2.3 Hz); 9.97 (s, 1H); 12.77 (sb, 1H).

LC-MS (1): retention time 3.38 min; LC-MS-DAD-ELSD: 221 (−)=(M−H)(−); 225(+)=(M+H)(+).

EXAMPLE 17

(5Z)-5-[(5-methyl-1H-pyrrolo[2,3-b]pyridin-3-yl)methylidene]-2-thioxoimidazolidin-4-one a) (5Z)-5-[(5-methyl-1H-pyrrolo[2,3-b]pyridin-3-yl)methylidene]-2-thioxoimidazolidin-4-one can be prepared as in Example 1 but from 500 mg of raw 5-methyl-1H-pyrrolo[2,3-b]pyridine-3-carbaldehyde titrated at 65%, 362 mg of 2-thioxoimidazolidin-4-one and 106 mg of piperidine in 15 cm³ of ethanol. Heat the mixture under ethanol reflux for four hours under argon, then cool to 0° C. on an ice bath for ten minutes. Filter the suspension and concentrate the filtrate at reduced pressure to obtain 685 mg of (5Z)-5-[(5-methyl-1H-pyrrolo[2,3-b]pyridin-3-yl)methylidene]-2-thioxoimidazolidin-4-one in the form of a yellow powder with the following characteristics:

LC-MS: retention time: 2.83 min, 259(+)=(M+H)(+).

¹H-NMR spectrum at 400 Hz.: 2.42 (s: 3H); 6.73 (sb: 1H); 8.10 (d, J=2 Hz: 1H); 8.15 (d, J=2 Hz: 1H); 8.49 (s: 1H); 11.5-12.1 (massive: 2H); 12.26 (se, 1H).

b) 5-methyl-1H-pyrrolo[2,3-b]pyridine-3-carbaldehyde can be prepared as follows:

Add 1.6 g of 1,3,5,7-tetraazatricyclo[3.3.1.1~3,7~]decane to a suspension of 1 g of 5-methyl-1H-pyrrolo[2,3-b]pyridine in a mixture of 10 cm³ of water and 5 cm³ of acid acetic. Reflux the mixture under argon for four hours and thirty minutes, then add 30 cm³ of water to the hot mixture and leave to return to room temperature while stirring overnight. Then extract the mixture with three times 50 cm³ of ethyl acetate. Then combine the organic phases and wash with 3 times 50 cm³ of water, dry over magnesium sulphate and concentrate to dryness at reduced pressure to obtain 610 mg of a mixture containing 65% (by NMR) of 5-methyl-1H-pyrrolo[2,3-b]pyridine-3-carbaldehyde in the form of a yellow powder, for which the characteristics of the main product are as follows:

LC-MS: retention time 3.79 min, 161(+)=(M+H)(+).

¹H-NMR spectrum at 400 Hz: 2.41 (s: 3H); 8.21 (d, J=2 Hz: 1H); 8.22 (d, J=2 Hz: 1H); 8.40 (s: 1H); 9.90 (s: 1H); 12.5-12.7 (se: 1H).

c) 5-methyl-1H-pyrrolo[2,3-b]pyridine can be prepared as follows:

Add 7 g of potassium tert-butanolate to a suspension of 7.5 g of 5-methyl-3-[(trimethylsilyl)ethynyl]pyridin-2-amine in 170 cm³ of NMP. Reflux the reaction mixture for six hours thirty minutes under argon then allow to return to room temperature overnight. Then pour the reaction mixture slowly into 740 cm³ of a saturated aqueous solution of ammonium chloride and filter the insoluble matter on celite. Extract the filtrate with three times 500 cm³ of ethyl acetate then wash the combined organic phases with water, dry over magnesium sulphate and concentrate to dryness at reduced pressure. Then take up the residue in ethyl acetate. The solution obtained is washed with water, then dried over magnesium sulphate and concentrated to dryness at reduced pressure to obtain 2.6 g of 5-methyl-1H-pyrrolo[2,3-b]pyridine in the form of a brown solid with the following characteristics:

LC-MS: retention time 0.85 min, 133(+)=(M+H)(+).

¹H-NMR spectrum at 400 Hz: 2.38 (s: 3H); 6.35 (dd, J=1.5, 3 Hz: 1H); 7.38 (dd, J=2.5, 3 Hz: 1H), 7.73 (db, J=1 Hz: 1H); 8.2 (d, J=2 Hz: 1H); 11.42 (se, 1H).

d) 5-methyl-3-[(trimethylsilyl)ethynyl]pyridin-2-amine can be prepared as follows:

A suspension of 1 g of 2-amino-3-bromo-5-methylpyridine with 204 mg of CuI and 250 mg of lithium chloride in 30 cm³ of dimethylformamide is placed under argon and stirred. 3.7 cm³ of triethylamine, 195 mg of [1,1'-bis(diphenylphosphino)ferrocene]dichloropalladium(II) and 800 mg of trimethylsilylacetylene are then added successively. The mixture is heated at 48° C. for twenty-two hours. The reaction mixture is then concentrated to dryness at reduced pressure, and the residue is taken up in a mixture of 30 cm³ of ethyl acetate and 30 cm³ of water. Brown insoluble matter is filtered on celite. The phases are separated and the organic phase is washed with two times 30 cm³ of water. The aqueous phase is extracted with 30 cm³ of ethyl acetate, then all the organic phases are combined, dried over magnesium sulphate and concentrated to dryness at reduced pressure. The residue is purified by flash chromatography on a silica column [eluent: n-hexane/ethyl acetate (gradient from 5/95 to 40/60 by volume)], to give 353 mg of 5-methyl-3-[(trimethylsilyl)ethynyl]pyridin-2-amine in the form of a beige solid with the following characteristics:

LC-MS: retention time 3.28 min, 205(+)=(M+H)(+).

¹H-NMR spectrum at 400 Hz: 0.20 (m: 9H); 2.10 (s: 3H); 5.90 (se: 2H); 7.40 (s: 1H); 7.85 (se: 1H).

EXAMPLE 18

(5Z)-2-thioxo-5-{[5-(trifluoromethyl)-1H-pyrrolo[2,3-b]pyridin-3-yl]methylidene}imidazolidin-4-one a) (5Z)-2-thioxo-5-{[5-(trifluoromethyl)-1H-pyrrolo[2,3-b]pyridin-3-yl]methylidene}imidazolidin-4-one can be prepared as in Example 1, but from 174 mg of 5-trifluoromethyl-1H-pyrrolo[2,3-b]pyridine-3-carbaldehyde in 6 cm³ of ethanol, 94 mg of 2-thioxoimidazolidin-4-one and 0.03 cm³ of piperidine. After refluxing for two hours and thirty minutes, 148 mg of a mixture containing 80% of (5Z)-2-thioxo-5-{[5-(trifluoromethyl)-1H-pyrrolo[2,3-b]pyridin-3-yl]methylidene}imidazolidin-4-one is obtained in the form of orange powder, for which the characteristics of the main compound are as follows:

LC-MS: retention time 3.28 min; 313(+)=(M+H)(+).

¹H-NMR spectrum at 400 MHz: 6.98 (s, 1H); 8.52 (d, J=2 Hz, 1H); 8.66 (d, J=2 Hz, 1H); 9.07 (s, 1H); 12.00 (s broad, 1H).

b) 5-trifluoromethyl-1H-pyrrolo[2,3-b]pyridine-3-carbaldehyde can be prepared as follows:

Add 926 mg of 1,3,5,7-tetraazatricyclo[3.3.1.1~3,7~]decane to a mixture of 820 mg of 5-trifluoromethyl-1H-pyrrolo[2,3-b]pyridine in 6 cm³ of water and 3 cm³ of acid acetic. Reflux the reaction mixture for two hours and thirty minutes. Then add 6 cm³ of water to the hot mixture. On returning to a temperature close to 25° C., the mixture is extracted with ethyl acetate (40 cm³). The organic phase is washed with a saturated solution of sodium chloride, dried over magnesium sulphate and concentrated under vacuum. The residue is purified by chromatography on silica (elution with a 20-100% gradient of ethyl acetate in heptane) to obtain 123 mg of 5-trifluoromethyl-1H-pyrrolo[2,3-b]pyridine-3-carbaldehyde in the form of a beige powder with the following characteristics:

LC-MS: retention time 3.14 min; 215(+)=(M+H)(+).

¹H-NMR spectrum at 400 MHz: 8.67 (d, J=2.4 Hz, 1H); 8.75 (d, J=2.4 Hz, 1H); 8.69 (s, 1H); 10.00 (s, 1H); 13.17 (s broad, 1H).

c) 5-trifluoromethyl-1H-pyrrolo[2,3-b]pyridine can be prepared as follows:

A solution of 3.4 g of 5-trifluoromethyl-3-[(trimethylsilyl)ethynyl]pyridin-2-amine and 2.96 g of potassium tert-butylate in 55 cm³ of N-methylpyrrolidinone is heated at 90° C. for three hours. The mixture is cooled to room temperature then poured slowly into 250 cm³ of water saturated with ammonium chloride. The mixture is diluted with ethyl acetate, filtered and the phases are separated into their isomers and the aqueous phase is extracted with ethyl acetate (2×100 cm³). The organic phases are combined, dried over magnesium sulphate and concentrated under vacuum. The residue is taken up slowly in water and the resultant suspension is filtered. The solid is dried under vacuum to obtain 1.58 g of 5-trifluoromethyl-1H-pyrrolo[2,3-b]pyridine in the form of a brown powder with the following characteristics:

LC-MS: retention time 3.55 min; 187(+)=(M+H)(+).

¹H-NMR spectrum at 400 MHz: 6.63 (dd, J=1.7 and 3.5 Hz, 1H); 7.69 (dd, J=2.2 and 3.5 Hz, 1H); 8.38 (d, J=1.7 Hz, 1H); 8.55 (d, J=2.2 Hz, 1H); 12.16 (s broad, 1H).

d) 5-trifluoromethyl-3-[(trimethylsilyl)ethynyl]pyridin-2-amine can be prepared as follows:

A mixture of 6.68 g of 2-amino-3-iodo-5-trifluoromethylpyridine, 11.7 g of lithium chloride, 0.88 g of copper iodide, 11.7 g of triethylamine, 0.85 g of [1,1'-bis(diphenylphosphino)ferrocene]-dichloropalladium(II) and 3.4 g of trimethylsilylacetylene in 160 cm³ of dimethylformamide is heated at 48° C. for twenty-three hours. The mixture is cooled to room temperature then concentrated under vacuum. The residue is taken up in 200 cm³ of water and 200 cm³ of ethyl acetate. The insoluble matter is filtered and the organic phase is washed with water, dried over magnesium sulphate and concentrated under vacuum. The residue is purified by chromatography on a silica column [eluent: ethyl acetate/heptane (gradient from 0/100 to 30/70 by volume)], to obtain 3.42 g of 5-trifluoromethyl-3-[(trimethylsilyl)ethynyl]pyridin-2-amine in the form of beige powder with the following characteristics:

LC-MS: retention time: 4.94 min; LC-MS-DAD-ELSD: 259(+)=(M+H)(+).

e) 2-amino-3-iodo-5-trifluoromethyl-pyridine can be prepared as follows:

A mixture of 4.0 g of 2-amino-5-trifluoromethyl-pyridine and 6.2 g of N-iodo succinimide in 110 cm³ of acid acetic is heated at 70° C. for three hours, then cooled to room temperature and concentrated under vacuum. The residue is taken up slowly in 60 cm³ of water saturated with sodium bicarbonate, then 60 cm³ of water. The solid which precipitates is filtered and then dried under vacuum to obtain 6.68 g of 2-amino-3-iodo-5-trifluoromethyl-pyridine in the form of a beige solid with the following characteristics:

LC-MS: retention time: 3.72 min; LC-MS-DAD-ELSD: 289(+)=(M+H)(+).

EXAMPLE 19

(5Z)-5-[(5-fluoro-1H-pyrrolo[2,3-b]pyridin-3-yl) methylidene]-2-thioxoimidazolidin-4-one a) (5Z)-5-[(5-fluoro-1H-pyrrolo[2,3-b]pyridin-3-yl)methylidene]-2-thioxoimidazolidin-4-one can be prepared as in Example 1, but from 265 mg of 5-fluoro-1H-pyrrolo[2,3-b]pyridine-3-carbaldehyde, 13 cm³ of ethanol, 190 mg of 2-thioxoimidazolidin-4-one and 0.16 cm³ of piperidine. After refluxing for 2.5 hours, 327 mg of (5Z)-5-[(5-fluoro-1H-pyrrolo[2,3-b]pyridin-3-yl)methylene]-2-thioxoimidazolidin-4-one is obtained in the form of orange powder with the following physical characteristics:

¹H-NMR spectrum at 400 MHz: 6.81 (s, 1H); 8.30 (m, 2H); 8.60 (s, 1H); 11.93 (s broad, 1H); 12.57 (s broad, 1H).

LC-MS (1): retention time 2.91 min; LC-MS-DAD-ELSD: 261 (−)=(M−H)(−); 263(+)=(M+H)(+).

b) 5-fluoro-1H-pyrrolo[2,3-b]pyridine-3-carbaldehyde can be prepared as in Example 2 but from 545 mg of 5-fluoro-1H-pyrrolo[2,3-b]pyridine, in a mixture of 3.4 cm³ of water and 1.6 cm³ of acid acetic, and 545 mg of 1,3,5,7-tetraazatricyclo[3.3.1.1~3,7~]-decane. 265 mg of 5-fluoro-1H-pyrrolo[2,3-b]pyridine-3-carbaldehyde is obtained in the form of a beige solid with the following physical characteristics:

¹H-NMR spectrum at 400 MHz: 8.15 (dd, J=3 and 9 Hz, 1H); 8.36 (dd, 1.8 and 3 Hz, 1H); 8.53 (s, 1H); 9.90 (s, 1H); 12.79 (s broad, 1H).

LC-MS (1): retention time: 2.59 min; LC-MS-DAD-ELSD 163 (−)=(M−H)(−); 165(+)=(M+H)(+).

c) 5-fluoro-1H-pyrrolo[2,3-b]pyridine can be prepared as described in WO2005/103050.

EXAMPLE 20

3-[(Z)-(5-oxo-2-thioxoimidazolidin-4-ylidene)methyl]-1H-pyrrolo[2,3-b]pyridine-5-carbonitrile a) 3-[(Z)-(5-oxo-2-thioxoimidazolidin-4-ylidene)methyl]-1H-pyrrolo[2,3-b]pyridine-5-carbonitrile can be prepared as in Example 1, but from 173 mg of 3-formyl-1H-pyrrolo[2.3]pyridine-5-carbonitrile, in 7.4 cm³ of ethanol, 122 mg of 2-thioxoimidazolidin-4-one, and 0.05 cm³ of piperidine. After refluxing for three hours, 200 mg of 3-[5-oxo-2-thioxoimidazolidin-(4Z)-ylidenemethyl]-1H-pyrrolo{[2,3-b]pyridine-5-carbonitrile is obtained in the form of orange powder, with the following physical characteristics:

LC-MS (1): retention time 2.86; LC-MS-DAD-ELSD: 270 (+)=(M+H)(+).

¹H-NMR spectrum at 400 MHz: 6.84 (s, 1H); 8.66 (s, 1H); 8.69 (s, 1H); 8.99 (s, 1H); 12.17 (s broad, 1H).

b) 3-formyl-1H-pyrrolo[2,3]pyridine-5-carbonitrile can be prepared as in Example 2, but from 860 mg of 1H-pyrrolo[2.3]pyridine-5-carbonitrile in a mixture of 15 cm³ of water and 4.8 cm³ of acid acetic, and 1.26 g of tetraazatricyclo[3.3.1.1~3,7~]decane. 275 mg of 3-formyl-1H-pyrrolo[2,3]pyridine-5-carbonitrile is obtained in the form of beige powder with the following physical characteristics:

¹H-NMR spectrum at 400 MHz: 8.66 (s, 1H); 8.77 (m, 2H); 9.98 (s, 1H).

LC-MS (1): retention time 2.39 min; LC-MS-DAD-ELSD: 170(−)=(M−H)(−); 172(+)=(M+H)(+).

c) 1H-pyrrolo[2,3-b]pyridine-5-carbonitrile can be prepared as described in WO2004/078756.

EXAMPLE 21

(5Z)-5-[(5-phenylamino-1H-pyrrolo[2,3-b]pyridin-3-yl)methylene]-2-thioxoimidazolidin-4-one a) (5Z)-5-[(5-phenylamino-1H-pyrrolo[2,3-b]pyridin-3-yl)methylene]-2-thioxoimidazolidin-4-one can be prepared as in Example 1, but from 63 mg of 5-phenylamino-1H-pyrrolo[2,3-b]pyridine-3-carbaldehyde in 2 cm³ of ethanol, 32 mg of 2-thioxoimidazolidin-4-one and 0.03 cm³ of piperidine. After refluxing for 2.5 hours, 70 mg of (5Z)-5-[(5-phenylamino-1H-pyrrolo[2,3-b]pyridin-3-yl)methylene]-2-thioxoimidazolidin-4-one is obtained in the form of orange powder with the following physical characteristics:

¹H-NMR spectrum at 400 MHz: 6.71 (s, 1H); 6.76 (t, J=7.6 Hz, 1H); 7.01 (d, J=7.6 Hz, 2H); 7.21 (t, J=7.6 Hz, 2H); 7.98 (d, J=2.4 Hz, 1H); 8.06 (s, 1H); 8.12 (d, J=2.4 Hz, 1H); 8.47 (s, 1H); 11.70 (s broad, 3H); 12.29 (s broad, 1H).

LC-MS (1): retention time 3.55 min; LC-MS-DAD-ELSD 334 (−)=(M−H)(−); 336(+)=(M+H)(+).

b) 5-phenylamino-1H-pyrrolo[2,3-b]pyridine-3-carbaldehyde can be prepared as in Example 14 but from 1.6 g of aluminium chloride in suspension in 25 cm³ of dichloromethane, 0.5 g of N-phenyl-1H-pyrrolo[2,3-b]pyridin-5-amine, and 1.1 cm³ of dichloro(methoxy)methane. After one hour thirty minutes of reaction and hydrolysis of the reaction mixture, 180 mg of a raw product is obtained, which is then purified by flash chromatography on a silica column with dichloromethane/ethyl acetate eluent (gradient from 80/20 to 50/50 by volume). 70 mg of 5-phenyl-1H-pyrrolo[2,3-b]pyridine-3-carbaldehyde is obtained in the form of ochre powder with the following physical characteristics:

¹H-NMR spectrum at 400 MHz: 6.80 (t, J=7.4 Hz, 1H); 7.02 (d, J=7.4 Hz, 2H); 7.24 (t, J=7.4 Hz, 2H); 8.17 (m, 3H); 8.36 (s, 1H); 9.86 (s, 1H), 12.56 (s broad, 1H).

LC-MS-DAD-ELSD: 236(−)=(M−H)(−); 237(+)=(M+H)(+).

c) 5-phenylamino-1H-pyrrolo[2,3-b]pyridine can be prepared as in Example 5, but by reacting 1.34 g of 1-[(4-methylphenyl)sulphonyl]-N-phenyl-1H-pyrrolo[2,3-b]pyridin-5-amine in 30 cm³ of methanol, and 4.15 g of potassium hydroxide for three hours at room temperature. After treatment of the reaction mixture, 0.63 g of 5-phenylamino-1H-pyrrolo[2,3-b]pyridine is obtained in the form of beige powder with the following physical characteristics:

¹H-NMR spectrum at 400 MHz: 6.35 (d, J=3.5 Hz, 1H); 6.69 (t, J=7.5 Hz, 1H); 6.89 (d, J=7.5 Hz, 2H); 7.15 (t, J=7.5

Hz, 2H); 7.40 (s broad, 1H); 7.70 (d, J=2.6 Hz, 1H) 7.83 (s, 1H); 8.04 (d, J=2.6 Hz, 1H), 11.45 (s broad, 1H).

LC/MS retention time 3.22 min; LC-MS-DAD-ELSD208 (−)=(M−H)(−); 210(+)=(M+H)(+).

d) 1-[(4-methylphenyl)sulphonyl]-N-phenyl-1H-pyrrolo[2,3-b]pyridin-5-amine can be prepared as follows:

Put 750 mg of 5-bromo-1-[(4-methylphenyl)sulphonyl]-1H-pyrrolo[2,3-b]pyridine in 19 cm³ of toluene, 54 mg of 9,9-dimethyl-4,5-bis(diphenylphosphino)xanthene, 970 mg of caesium carbonate, 280 mg of aniline and 40 mg of tri(dibenzylideneacetone)dipalladium(0) in a microwave oven reactor. Irradiate the reactor in a microwave oven for forty-five minutes at 150° C. After cooling, filter the reaction mixture, then reduce to dryness under vacuum in a rotary evaporator. Combine the brown residue with another two residues obtained similarly, then purify by flash chromatography on a silica column with dichloromethane eluent to give 1.34 g of 1-[(4-methylphenyl)sulphonyl]-N-phenyl-1H-pyrrolo[2,3-b]pyridin-5-amine in the form of a beige powder with the following physical characteristics:

LC/MS retention time 4.58 min; LC-MS-DAD-ELSD; 364 (+)=(M+H)(+).

e) 5-bromo-1-[(4-methylphenyl)sulphonyl]-1H-pyrrolo[2,3-b]pyridine can be prepared as follows:

Add 1.63 g of 5-bromo-1H-pyrrolo[2,3-b]pyridine, 30 mg of tetrabutyl ammonium hydrogen sulphate, 1.81 g of tosyl chloride and 4.3 g of sodium hydroxide pellets in solution in 40 cm³ of water to 41 cm³ of toluene. After stirring for four hours at room temperature, pour the reaction mixture into 50 cm³ of water. Extract the mixture obtained with 50 cm³ of ethyl acetate. The organic phase is decanted, dried over magnesium sulphate, filtered and then evaporated to dryness under vacuum in a rotary evaporator. 2.4 g of 5-bromo-1-[(4-methylphenyl)sulphonyl]-1H-pyrrolo[2,3-b]pyridine is obtained in the form of white powder with the following physical characteristics:

LC/MS retention time 4.70 min; LC-MS-DAD-ELSD 353 (+)=(M+H)(+) (1 bromine atom Br present).

EXAMPLE 22

(5Z)-5-[(5-morpholin-4-yl-1H-pyrrolo[2,3-b]pyridin-3-yl)methylidene]-2-thioxoimidazolidin-4-one a) (5Z)-5-[(5-morpholin-4-yl-1H-pyrrolo[2,3-b]pyridin-3-yl)methylidene]-2-thioxoimidazolidin-4-one can be prepared as in Example 1, but from 140 mg of 5-morpholin-4-yl-1H-pyrrolo[2,3-b]pyridine-3-carbaldehyde in 4.5 cm³ of ethanol, 75 mg of 2-thioxoimidazolidin-4-one and 0.03 cm³ of piperidine. After refluxing for 2.5 hours, 160 mg of (5Z)-5-[(5-morpholin-4-yl-1H-pyrrolo[2,3-b]pyridin-3-yl)methylene]-2-thioxoimidazolidin-4-one is obtained in the form of orange powder with the following physical characteristics: LC-MS (1): retention time 2.68 min; LC-MS-DAD-ELSD 328(−)=(M−H)(−); 230(+)=(M+H)(+).

¹H-NMR spectrum at 400 MHz: 3.16 (m, 4H); 3.78 (m, 4H); 6.88 (s, 1H); 7.86 (d, J=2.3 Hz, 1H); 8.15 (d, J=2.3 Hz, 1H); 8.48 (s, 1H); 11.78 (s broad, 1H); 12.09 (s broad, 1H); 12.23 (s broad, 1H).

b) 5-morpholin-4-yl-1H-pyrrolo[2,3-b]pyridine-3-carbaldehyde can be prepared as in Example 14 but from 2 g of aluminium chloride in suspension in 50 cm³ of dichloromethane, 0.59 g of 5-morpholin-4-yl-1H-pyrrolo[2,3-b]pyridine and 0.8 cm³ of dichloro(methoxy)methane. After one hour thirty minutes of reaction and hydrolysis of the reaction mixture, 140 mg of 5-morpholin-4-yl-1H-pyrrolo[2,3-b]pyridine-3-carbaldehyde is obtained in the form of a beige powder with the following physical characteristics:

LC/MS retention time 2.35 min; LC-MS-DAD-ELSD 230 (−)=(M−H)(−); 232 (+)=(M+H)(+).

¹H-NMR spectrum at 400 MHz: 3.12 (m, 4H); 3.78 (m, 4H); 7.88 (d, J=2.8 Hz, 1H); 8.22 (d, J=2.8 Hz, 1H); 8.34 (s, 1H); 9.87 (s, 1H); 12.48 (s broad, 1H).

c) 5-morpholin-4-yl-1H-pyrrolo[2,3-b]pyridine can be prepared as in Example 5, but from 1.18 g of 1-[(4-methylphenyl)sulphonyl]-5-morpholin-4-yl-1H-pyrrolo[2,3-b]pyridine in 33 cm³ of methanol and 3.7 g of potassium hydroxide pellets. After treatment of the reaction mixture, 0.59 g of 5-morpholin-4-yl-1H-pyrrolo[2,3-b]pyridine is obtained in the form of beige powder with the following physical characteristics:

¹H-NMR spectrum at 400 MHz: 3.05 (m, 4H); 3.77 (m, 4H); 6.32 (dd, J=2 and 3.2 Hz, 1H); 7.36 (dd, J=2 and 3.2 Hz, 1H); 7.48 (d, J=2.7 Hz, 1H); 8.06 (d, J=2.7 Hz, 1H); 11.35 (s broad, 1H).

LC/MS retention time 1.27 min; LC-MS-DAD-ELSD:204 (+)=(M+H)(+).

d) 1-[(4-methylphenyl)sulphonyl]-5-morpholin-4-yl-1H-pyrrolo[2,3-b]pyridine can be prepared as in Example 21 but from 62 cm³ of toluene, 2.6 g of 5-bromo-1-[(4-methylphenyl)sulphonyl]-1H-pyrrolo[2,3-b]pyridine, 3.35 g of caesium carbonate, 170 mg of 9,9-dimethyl-4,5-bis(diphenylphosphino)xanthene, 0.9 g of morpholine and 130 mg of tri(dibenzylideneacetone)dipalladium(0). The reactor is irradiated in a microwave oven, for one hour at 150° C. After cooling, the reaction mixture is filtered, and evaporated to dryness under vacuum in a rotary evaporator. The brown residue obtained is purified by flash chromatography on a silica column with dichloromethane/ethyl acetate eluent (gradient from 100 to 90/10 by volume) to give 1.18 g of 1-[(4-methylphenyl)sulphonyl]-5-morpholin-4-yl-1H-pyrrolo[2,3-b]pyridine in the form of beige powder with the following physical characteristics:

LC/MS retention time 3.96 min; LC-MS-DAD-ELSD: 358 (+)=(M+H)(+).

EXAMPLE 23

(5Z)-5-[(5-benzyl-1H-pyrrolo[2,3-b]pyridin-3-yl)methylidene]-2-thioxoimidazolidin-4-one a) (5Z)-5-[(5-benzyl-1H-pyrrolo[2,3-b]pyridin-3-yl)methylidene]-2-thioxoimidazolidin-4-one can be prepared as in Example 1, but from 55 mg of 5-benzyl-4-yl-1H-pyrrolo[2,3-b]pyridine-3-carbaldehyde in 1.8 cm³ of ethanol, 27 mg of 2-thioxoimidazolidin-4-one and 0.023 cm³ of piperidine. After refluxing for 2.5 hours, 60 mg of (5Z)-5-[(5-morpholin-4-yl-1H-pyrrolo[2,3-b]pyridin-3-yl)methylene]-2-thioxoimidazolidin-4-one is obtained in the form of orange powder with the following physical characteristics:

¹H-NMR spectrum at 400 MHz: 4.06 (s, 2H); 6.69 (s, 1H); 7.17 (t, J=6.9 Hz, 1H); 7.29 (m, 4H); 8.17 (d, J=1.8 Hz, 1H); 8.23 (d, J=1.8 Hz, 1H); 8.49 (s, 1H); 11.35 (s broad, 1H); 12.26 (s broad, 1H).

LC-MS (1): retention time 3.66 min; LC-MS-DAD-ELSD: 333(−)=(M−H)(−); 335(+)=(M+H)(+).

b) 5-benzyl-1H-pyrrolo[2,3-b]pyridine-3-carbaldehyde can be prepared as in Example 16, but from 260 mg of 5-bromo-1-[(4-methylphenyl)sulphonyl]-1H-pyrrolo[2,3-b]pyridine 3-carbaldehyde, in 4.7 cm³ of tetrahydrofuran and 2.5 cm³ of water, 680 mg of caesium carbonate and 55 mg of 1,1'-bis(diphenylphosphino)ferrocenedichloropalladium(II). After forty-five minutes of irradiation at 150°

C., pour the reaction mixture into a water/ethyl acetate mixture. Dry the organic phase over sodium sulphate and extract the aqueous phase again with 2 times 50 cm³ of a dichloromethane/methanol 90/10 mixture by volume. Dry the dichloromethane phase over sodium sulphate then combine with the preceding organic phases before concentrating under vacuum in a rotary evaporator. The brown residue is purified by flash chromatography on a silica column with a dichloromethane/ethyl acetate eluent (gradient dichloromethane/ethyl acetate from 90/10 to 50/50 by volume) to give 55 mg of 5-benzyl-1H-pyrrolo[2,3-b]pyridine-3-carbaldehyde in the form of beige powder with the following physical characteristics:

¹H-NMR spectrum at 400 MHz: 4.09 (s, 2H); 7.19 (m, 1H); 7.28 (m, 4H); 8.22 (d, J=2.1 Hz, 1H); 8.31 (d, J=2.1 Hz, 1H); 8.42 (s, 1H); 9.87 (s, 1H); 12.61 (s broad, 1H). LC-MS (1): retention time 3.61 min; LC-MS-DAD-ELSD: 235 (−)=(M−H)(−); 237 (+)=(M+H) (+).

c) 5-bromo-1-[(4-methylphenyl)sulphonyl]-1H-pyrrolo[2,3-b]pyridine-3-carbaldehyde can be prepared as follows:

Add, at 0° C., 1 g of 5-bromo-1H-pyrrolo[2,3-b]pyridine-3-carbaldehyde, then 0.27 g of sodium hydride to 10 cm³ of anhydrous tetrahydrofuran. Stir the reaction mixture for fifteen minutes at 0° C. before adding 1.87 g of tosyl chloride in solution in 1.7 cm³ of tetrahydrofuran. Continue stirring the reaction mixture for two hours, allowing it to return to room temperature. Pour the reaction mixture into 100 cm³ of iced water. Extract the mixture obtained with two times 100 cm³ of ethyl acetate. Dry the organic phases over magnesium sulphate and then evaporate to dryness under vacuum in a rotary evaporator. 1.32 g of 5-bromo-1-[(4-methylphenyl)sulphonyl]-1H-pyrrolo[2,3-b]pyridine-3-carbaldehyde is obtained in the form of a beige powder with the following physical characteristics:

LC-MS-DAD-ELSD: 381(+)=(M+H)(+) (1 bromine atom Br present).

EXAMPLE 24

(5E/Z)-3-phenyl-5-(1H-pyrrolo[2,3-b]pyridin-3-ylmethylidene)-2-thioxoimidazolidin-4-one (5E/Z)-3-phenyl-5-(1H-pyrrolo[2,3-b]pyridin-3-ylmethylidene)-2-thioxoimidazolidin-4-one can be prepared as in Example 1, but from 75 mg of 1H-pyrrolo[2,3-b]pyridine-3-carbaldehyde in 3.5 cm³ of ethanol, 98 mg of 2-thioxoimidazolidin-3-phenyl-4-one (SIGMA) and 0.02 cm³ of piperidine. After refluxing for five hours, 151 mg of a 50/50 mixture of (5Z/E)-3-phenyl-5-(1H-pyrrolo[2,3-b]pyridin-3-ylmethylidene)-2-thioxoimidazolidin-4-one is obtained in the form of a yellow powder with the following characteristics:

¹H-NMR spectrum at 400 MHz: 7.01 (s, 0.5H); 7.11 (s, 0.5H); 7.21 (dd, J=5.0 and 8.0 Hz, 0.5H); 7.28 (dd, J=5.0 and 8.0 Hz, 0.5H); 7.39 (m, 2H); from 7.42 to 7.58 (m, 3H); 8.13 (dd, J=1.5 and 8.0 Hz, 0.5H); 8.33 (m, 1.5H); 8.67 (d, J=2.0 Hz, 0.5H); 8.99 (d, J=2.0 Hz, 0.5H); from 12.2 to 12.6 (m, 2H).

HPLC-MS-DAD-ELSD: 321(+)=(M+H) (+); 319(−)=(M−H) (−) (50/50 mixture of isomers).

EXAMPLE 25

(5Z)-2-azepan-1-yl-5-[(5-chloro-1H-pyrrolo[2,3-b]pyridin-3-yl)methylidene]-3,5-dihydro-4H-imidazol-4-one (5Z)-2-azepan-1-yl-5-[(5-chloro-1H-pyrrolo[2,3-b]pyridin-3-yl)methylidene]-3,5-dihydro-4H-imidazol-4-one can be prepared as in Example 7, but from 278 mg of (5Z)-5-[(5-chloro-1H-pyrrolo[2,3-b]pyridin-3-yl)methylene]-2-thioxoimidazolidin-4-one (Example 3), 2.5 cm³ of ethanol and 992 mg of azepane. After one hour at a temperature of 160° C. under microwave irradiation and filtration of the solid, 92 mg of (5Z)-2-azepan-1-yl-5-[(5-chloro-1H-pyrrolo[2,3-b]pyridin-3-yl)methylidene]-3,5-dihydro-4H-imidazol-4-one is obtained in the form of a yellow powder with the following characteristics:

Melting point: 310-320° C.

¹H-NMR spectrum at 400 MHz: 1.53 (m, 4H); 1.78 (m broad, 4H); 3.63 (m spread out, 4H); 6.58 (s, 1H); 8.13 (s, 1H); 8.21 (d, J=3.0 Hz, 1H); 9.21 (s broad, 1H); 11.0 (m spread out, 1H); 12.15 (m spread out, 1H).

HPLC-MS-DAD-ELSD: 344(+)=(M+H)(+); 342(−)=(M−H)(−).

EXAMPLE 26

(5Z)-5-[(5-chloro-1H-pyrrolo[2,3-b]pyridin-3-yl)methylidene]-2-(4-phenylpiperazin-1-yl)-3,5-dihydro-4H-imidazol-4-one (5Z)-5-[(5-chloro-1H-pyrrolo[2,3-b]pyridin-3-yl)methylidene]-2-(4-phenylpiperazin-1-yl)-3,5-dihydro-4H-imidazol-4-one can be prepared as in Example 7, but from 167 mg of (5Z)-5-[(5-chloro-1H-pyrrolo[2,3-b]pyridin-3-yl)methylene]-2-thioxoimidazolidin-4-one (Example 3), 2 cm³ of ethanol and 973 mg of 4-phenylpiperazine. After one hour at a temperature of 160° C. under microwave irradiation, then filtration of the solid, 182 mg of (5Z)-5-[(5-chloro-1H-pyrrolo[2,3-b]pyridin-3-yl)methylidene]-2-(4-phenylpiperazin-1-yl)-3,5-dihydro-4H-imidazol-4-one is obtained in the form of orange powder with the following characteristics:

Melting point: 340-350° C.

¹H-NMR spectrum at 400 MHz: 3.29 (m partially masked, 4H); 3.75 (m, 4H); 6.70 (s, 1H); 6.82 (J=7.5 Hz, 1H); 7.02 (d, J=7.5 Hz, 2H); 7.24 (t, J=7.5 Hz, 2H); 8.24 (d, J=3.0 Hz, 1H); 8.28 (s, 1H); 8.98 (d, J=3.0 Hz, 1H); 11.2 (s broad, 1H); 12.2 (s broad, 1H).

UPLC-MS-DAD-ELSD: 407(+)/ . . . =(M+H)(+)/ . . . (1 chlorine atom Cl present).

EXAMPLE 27

(5Z)-5-[(5-chloro-1H-pyrrolo[2,3-b]pyridin-3-yl)methylidene]-2-pyrrolidin-1-yl-3,5-dihydro-4H-imidazol-4-one (5Z)-5-[(5-chloro-1H-pyrrolo[2,3-b]pyridin-3-yl)methylidene]-2-pyrrolidin-1-yl-3,5-dihydro-4H-imidazol-4-one can be prepared as in Example 7, but from 223 mg of (5Z)-5-[(5-chloro-1H-pyrrolo[2,3-b]pyridin-3-yl)methylene]-2-thioxoimidazolidin-4-one (Example 3), 2.5 cm³ of ethanol and 569 mg of pyrrolidine. After thirty minutes at a temperature of 160° C. under microwave irradiation, then filtration of the solid, 186 mg of (5Z)-5-[(5-chloro-1H-pyrrolo[2,3-b]pyridin-3-yl)methylidene]-2-pyrrolidin-1-yl-3,5-dihydro-4H-imidazol-4-one is obtained in the form of a yellow powder with the following characteristics:

Melting point: 350-360° C.

¹H-NMR spectrum at 400 MHz: 1.94 (m, 4H); 3.52 (m broad, 4H); 6.59 (s, 1H); 8.19 (s, 1H); 8.21 (d, J=3.0 Hz, 1H); 9.15 (m spread out, 1H); 11.1 (m spread out, 1H); 12.15 (m spread out, 1H).

HPLC-MS-DAD-ELSD: 316(+)/ . . . =(M+H)(+)/ . . . ; 314(−)/ . . . =(M−H)(−)/ . . . .

EXAMPLE 28

(5Z)-5-[(5-chloro-1H-pyrrolo[2,3-b]pyridin-3-yl) methylidene]-2-morpholin-4-yl-3,5-dihydro-4H-imidazol-4-one (5Z)-5-[(5-chloro-1H-pyrrolo[2,3-b]pyridin-3-yl)methylidene]-2-morpholin-4-yl-3,5-dihydro-4H-imidazol-4-one can be prepared as in Example 7, but from 139 mg of (5Z)-5-[(5-chloro-1H-pyrrolo[2,3-b]pyridin-3-yl)methylene]-2-thioxoimidazolidin-4-one (Example 3), 2.5 cm$^3$ of ethanol and 436 mg of morpholine. After two hours at a temperature of 160° C. under microwave irradiation, then filtration of the solid, 92 mg of (5Z)-5-[(5-chloro-1H-pyrrolo[2,3-b]pyridin-3-yl)methylidene]-2-morpholin-4-yl-3,5-dihydro-4H-imidazol-4-one is obtained in the form of a yellow powder with the following characteristics:
$^1$H-NMR spectrum at 400 MHz: 3.59 (m, 4H); 3.70 (m, 4H); 6.70 (s, 1H); 8.22 (m, 2H); 8.94 (m spread out, 1H); 11.15 (m spread out, 1H); 12.2 (m spread out, 1H).

EXAMPLE 29

(5Z)-5-[(5-chloro-1H-pyrrolo[2,3-b]pyridin-3-yl) methylidene]-2-[(2-methylpropyl)amino]-3,5-dihydro-4H-imidazol-4-one (5Z)-5-[(5-chloro-1H-pyrrolo[2,3-b]pyridin-3-yl)methylidene]-2-[(2-methylpropyl)amino]-3,5-dihydro-4H-imidazol-4-one can be prepared as in Example 7 but from 200 mg of (5Z)-5-[(5-chloro-1H-pyrrolo[2,3-b]pyridin-3-yl)methylene]-2-thioxoimidazolidin-4-one (Example 3), 4 cm$^3$ of ethanol and 525 mg of 2-methylpropylamine. After forty-five minutes at a temperature of 160° C. under microwave irradiation, then filtration of the solid, 89 mg of (5Z)-5-[(5-chloro-1H-pyrrolo[2,3-b]pyridin-3-yl)methylidene]-2-[(2-methylpropyl)amino]-3,5-dihydro-4H-imidazol-4-one is obtained in the form of a yellow powder with the following characteristics:
Melting point: 325-330° C.
$^1$H-NMR spectrum at 400 MHz: 0.95 (d, J=6.5 Hz, 6H); 1.93 (m, 1H); 3.19 (t, J=6 Hz, 2H); 6.57 (s, 1H); 7.21 (s broad 1H); 8.11 (s, 1H); 8.21 (s broad, 1H); 9.25 (m spread out, 1H); 10.4 (m spread out, 1H); 12.15 (m spread out, 1H).
HPLC-MS-DAD-ELSD: 318(+)/ . . . =(M+H)(+)/ . . . ; 316(−)/ . . . =(M−H)(−)/ . . . (1 Cl present).

EXAMPLE 30

(5Z)-5-[(5-chloro-1H-pyrrolo[2,3-b]pyridin-3-yl) methylidene]-2-piperidin-1-yl-3,5-dihydro-4H-imidazol-4-one (5Z)-5-[(5-chloro-1H-pyrrolo[2,3-b]pyridin-3-yl)methylidene]-2-piperidin-1-yl-3,5-dihydro-4H-imidazol-4-one can be prepared as in Example 7, but from 195 mg of (5Z)-5-[(5-chloro-1H-pyrrolo[2,3-b]pyridin-3-yl)methylene]-2-thioxoimidazolidin-4-one (Example 3), 2.5 cm$^3$ of ethanol and 596 mg of piperidine. After thirty minutes at a temperature of 160° C. under microwave irradiation, then filtration of the solid, 152 mg of (5Z)-5-[(5-chloro-1H-pyrrolo[2,3-b]pyridin-3-yl)methylidene]-2-piperidin-1-yl-3,5-dihydro-4H-imidazol-4-one is obtained in the form of orange powder with the following characteristics:
Melting point: 315-320° C.
$^1$H-NMR spectrum at 400 MHz: Of 1.51 to 1.70 (m, 6H); 3.59 (m, 4H); 6.61 (s, 1H); 8.19 (s, 1H); 8.22 (d, J=3.0 Hz, 1H); 9.01 (m spread out, 1H); 11.0 (m spread out, 1H); 12.1 (m spread out, 1H).
HPLC-MS-DAD-ELSD: 330(+)/ . . . =(M+H)(+)/ . . . ; 328(−)/ . . . =(M−H)(−)/ . . . (1 Cl present).

EXAMPLE 31

(5Z)-5-[(5-chloro-1H-pyrrolo[2,3-b]pyridin-3-yl) methylidene]-2-[methyl(2-methylpropyl)amino]-3,5-dihydro-4H-imidazol-4-one (5Z)-5-[(5-chloro-1H-pyrrolo[2,3-b]pyridin-3-yl)methylidene]-2-[methyl(2-methylpropyl)amino]-3,5-dihydro-4H-imidazol-4-one can be prepared as in Example 7, but from 63 mg of (5Z)-5-[(5-chloro-1H-pyrrolo[2,3-b]pyridin-3-yl)methylene]-2-thioxoimidazolidin-4-one (Example 3), 1 cm$^3$ of ethanol and 187 mg of N-methyl-(2-methyl)propylamine. After fifteen minutes at a temperature of 160° C., thirty minutes at 170° C., and one hour thirty minutes at 180° C. under microwave irradiation, the mixture is concentrated under vacuum. The residue is taken up in methylene chloride and the solid is filtered to obtain 30 mg of (5Z)-5-[(5-chloro-1H-pyrrolo[2,3-b]pyridin-3-yl)methylidene]-2-[methyl(2-methylpropyl) amino]-3,5-dihydro-4H-imidazol-4-one in the form of a yellow powder with the following characteristics:
$^1$H-NMR spectrum at 400 MHz: 0.91 (d, J=6.5 Hz, 6H); 2.04 (m, 1H); 3.09 (s, 3H); 3.30 (m masked, 2H); 6.59 (s, 1H); 8.13 (s broad, 1H); 8.21 (d, J=2.0 Hz, 1H); 9.20 (m spread out, 1H); 11.1 (m spread out, 1H); 12.15 (m spread out, 1H).
HPLC-MS-DAD-ELSD: 332(+)/ . . . =(M+H)(+)/ . . . ; 330(−)/ . . . =(M−H)(−)/ . . . (1 chlorine atom Cl present).

EXAMPLE 32

(5Z)-5-[(5-chloro-1H-pyrrolo[2,3-b]pyridin-3-yl) methylidene]-2-(dimethylamino)-3,5-dihydro-4H-imidazol-4-one (5Z)-5-[(5-chloro-1H-pyrrolo[2,3-b]pyridin-3-yl)methylidene]-2-(dimethylamino)-3,5-dihydro-4H-imidazol-4-one can be prepared as in Example 7, but from 279 mg of (5Z)-5-[(5-chloro-1H-pyrrolo[2,3-b]pyridin-3-yl)methylene]-2-thioxoimidazolidin-4-one (Example 3), 1.5 cm$^3$ of ethanol and 2 cm$^3$ of solution of dimethylamine at 33% in ethanol. After thirty minutes at a temperature of 160° C. under microwave irradiation, then filtration of the solid, 220 mg of (5Z)-5-[(5-chloro-1H-pyrrolo[2,3-b]pyridin-3-yl)methylidene]-2-(dimethylamino)-3,5-dihydro-4H-imidazol-4-one is obtained in the form of a yellow powder with the following characteristics:
Melting point: 350° C.
$^1$H-NMR spectrum at 400 MHz: 3.10 (s, 6H); 6.60 (s, 1H); 8.19 (s, 1H); 8.22 (d, J=2.0 Hz, 1H); 9.09 (m spread out, 1H); 11.1 (m spread out, 1H); 12.15 (m spread out, 1H).
HPLC-MS-DAD-ELSD: 290(+)/ . . . =(M+H)(+)/ . . . (1 chlorine atom Cl present).

EXAMPLE 33

(5Z)-5-[(5-bromo-1H-pyrrolo[2,3-b]pyridin-3-yl) methylidene]-2-[(cyclopropylmethyl)amino]-3,5-dihydro-4H-imidazol-4-one (5Z)-5-[(5-bromo-1H-pyrrolo[2,3-b]pyridin-3-yl)methylidene]-2-[(cyclopropylmethyl)amino]-3,5-dihydro-4H- imidazol-4-one can be prepared as in Example 7, but from 860 mg of (5Z)-5-[(5-bromo-1H-pyrrolo[2,3-b]pyridin-3-yl)methylene]-2-thioxoimidazolidin-4-one (Example 14), 8 cm³ of ethanol and 1.89 g of 1-cyclopropylmethanamine. After thirty minutes at a temperature of 160° C. under microwave irradiation, then filtration of the solid, 500 mg of (5Z)-5-[(5-bromo-1H-pyrrolo[2,3-b]pyridin-3-yl)methylidene]-2-[(cyclopropylmethyl)amino-3,5-dihydro-4H-imidazol-4-one is obtained in the form of a pale yellow powder with the following characteristics:

¹H-NMR spectrum at 400 MHz: 0.30 (m, 2H); 0.49 (m, 2H); 1.17 (m, 1H); 3.38 (m partially masked, 2H); 6.59 (s, 1H); 7.23 (m broad, 1H); 8.11 (s, 1H); 8.28 (d, J=2.0 Hz, 1H); 9.32 (m broad, 1H); 10.4 (m spread out, 1H); 12.15 (m spread out, 1H).

HPLC-MS-DAD-ELSD: 360(+)=(M+H)(+); 358(−)=(M−H)(−) (1 bromine atom Br present).

EXAMPLE 34

(5Z)-2-[(cyclopropylmethyl)amino]-5-[(5-methoxy-1H-pyrrolo[2,3-b]pyridin-3-yl)methylidene]-3,5-dihydro-4H-imidazol-4-one (5Z)-2-[(cyclopropylmethyl)amino]-5-[(5-methoxy-1H-pyrrolo[2,3-b]pyridin-3-yl)methylidene]-3,5-dihydro-4H-imidazol-4-one can be prepared as in Example 7, but from 200 mg of (5Z)-5-[(5-methoxy-1H-pyrrolo[2,3-b]pyridin-3-yl)methylidene]-2-thioxoimidazolidin-4-one (Example 15), 3 cm³ of ethanol and 519 mg of 1-cyclopropylmethanamine. After forty minutes at a temperature of 130° C. and ten minutes at 140° C. under microwave irradiation, the mixture is concentrated under vacuum. The residue is purified by preparative LC-MS [Column Xterra RP18 30×100; 5p; with water buffered with 10 mM of ammonium hydrogen carbonate adjusted to pH 9 with ammonia/acetonitrile with gradient from 70/30 to 0/100 in 8 min], to obtain 58 mg of (5Z)-2-[(cyclopropylmethyl)amino]-5-[(5-methoxy-1H-pyrrolo[2,3-b]pyridin-3-yl)methylidene]-3,5-dihydro-4H-imidazol-4-one in the form of a yellow lyophilizate with the following characteristics:

Melting point: 280-286° C.

¹H-NMR spectrum at 400 MHz: 0.28 (m, 2H); 0.48 (m, 2H); 1.13 (m, 1H); from 3.15 to 3.40 (m partially masked, 2H); 3.88 (s, 3H); 6.62 (s, 1H); 7.14 (m, 1H); 7.98 (m, 1H); 8.11 (m, 1H); 8.40 (m, 1H); 10.35 (m spread out, 1H); 11.8 (m spread out, 1H).

HPLC-MS-DAD-ELSD: 312(+)=(M+H)(+); 310(−)=(M−H)(−).

EXAMPLE 35

(5Z)-2-[(cyclopropylmethyl)amino]-5-[(5-fluoro-1H-pyrrolo[2,3-b]pyridin-3-yl)methylidene]-3,5-dihydro-4H-imidazol-4-one (5Z)-2-[(cyclopropylmethyl)amino]-5-[(5-fluoro-1H-pyrrolo[2,3-b]pyridin-3-yl)methylidene]-3,5-dihydro-4H-imidazol-4-one can be prepared as in Example 7, but from 250 mg of (5Z)-5-[(5-fluoro-1H-pyrrolo[2,3-b]pyridin-3-yl)methylidene]-2-thioxoimidazolidin-4-one (Example 19), 4 cm³ of ethanol and 678 mg of 1-cyclopropylmethanamine. After thirty minutes at a temperature of 160° C. under microwave irradiation, then filtration of the solid, 73 mg of (5Z)-2-[(cyclopropylmethyl)amino]-5-[(5-fluoro-1H-pyrrolo[2,3-b]pyridin-3-yl)methylidene]-3,5-dihydro-4H-imidazol-4-one is obtained in the form of a yellow powder with the following characteristics:

Melting point: 312° C.

¹H-NMR spectrum at 400 MHz: 0.29 (m, 2H); 0.48 (m, 2H); 1.13 (m, 1H); 3.22 (t, J=6.0 Hz, 1H); 6.59 (s, 1H); 7.27 (m spread out, 1H); 8.22 (m, 2H); 8.76 (d broad, J=9.0 Hz, 1H); 10.45 (m spread out, 1H); 12.05 (m spread out, 1H).

UPLC-MS-DAD-ELSD: 300(+)=(M+H)(+).

EXAMPLE 36

(5Z)-2-azepan-1-yl-5-[(5-fluoro-1H-pyrrolo[2,3-b]pyridin-3-yl)methylidene]-3,5-dihydro-4H-imidazol-4-one (5Z)-2-azepan-1-yl-5-[(5-fluoro-1H-pyrrolo[2,3-b]pyridin-3-yl)methylidene]-3,5-dihydro-4H-imidazol-4-one can be prepared as in Example 7, but from 60 mg of (5Z)-5-[(5-fluoro-1H-pyrrolo[2,3-b]pyridin-3-yl)methylidene]-2-thioxoimidazolidin-4-one (Example 19), 0.6 cm³ of ethanol and 227 mg of azepane. After thirty minutes at a temperature of 160° C. under microwave irradiation, then filtration of the solid, 22 mg of (5Z)-2-azepan-1-yl-5-[(5-fluoro-1H-pyrrolo[2,3-b]pyridin-3-yl)methylidene]-3,5-dihydro-4H-imidazol-4-one is obtained in the form of a yellow powder with the following characteristics:

Melting point: 299° C.

¹H-NMR spectrum at 400 MHz: from 1.44 to 1.87 (m, 8H); 3.62 (m spread out, 4H); 6.59 (s, 1H); 8.21 (s broad, 2H); 8.77 (m spread out, 1H); 11.0 (m very broad, 1H); 12.05 (m spread out, 1H).

HPLC-MS-DAD-ELSD: 328(+)=(M+H)(+).

EXAMPLE 37

3-[(Z)-{2-[(cyclopropylmethyl)amino]-5-oxo-1,5-dihydro-4H-imidazol-4-ylidene}methyl]-1H-pyrrolo[2,3-b]pyridine-5-carbonitrile 3-[(Z)-{2-[(cyclopropylmethyl)amino]-5-oxo-1,5-dihydro-4H-imidazol-4-ylidene}methyl]-1H-pyrrolo[2,3-b]pyridine-5-carbonitrile can be prepared as in Example 7, but from 200 mg of 3-[(Z)-(5-oxo-2-thioxoimidazolidin-4-ylidene)methyl]-1H-pyrrolo[2,3-b]pyridine-5-carbonitrile (Example 20), 2 cm³ of ethanol and 528 mg of 1-cyclopropylmethanamine. After thirty minutes at a temperature of 140° C. under microwave irradiation, then filtration of the solid, 58 mg of 3-[(Z)-{2-[(cyclopropylmethyl)amino]-5-oxo-1,5-dihydro-4H-imidazol-4-ylidene}methyl]-1H-pyrrolo[2,3-b]pyridine-5-carbonitrile is obtained in the form of a yellow powder with the following characteristics:

Melting point: 335° C.

¹H-NMR spectrum at 400 MHz: 0.30 (m, 2H); 0.49 (m, 2H); 1.13 (m, 1H); from 3.15 to 3.40 (m masked, 2H); 6.60 (s, 1H); 7.40 (s broad, 1H); 8.25 (s broad, 1H); 8.60 (s, 1H); 9.53 (s broad, 1H); 10.7 (m spread out, 1H); 12.2 (m spread out, 1H).

HPLC-MS-DAD-ELSD: 307(+)=(M+H)(+); 305(−)=(M−H)(−).

EXAMPLE 38

(5Z)-2-[(cyclopropylmethyl)amino]-5-[(5-phenyl-1H-pyrrolo[2,3-b]pyridin-3-yl)methylidene]-3,5-dihydro-4H-imidazol-4-one (5Z)-2-[(cyclopropylmethyl)amino]-5-[(5-phenyl-1H-pyrrolo[2,3-b]pyridin-3-yl)methylidene]-3,5-dihydro-4H- imidazol-4-one can be prepared as in Example 7, but from 140 mg of (5Z)-5-[(5-phenyl-1H-pyrrolo[2,3-b]pyridin-3-yl)methylidene]-2-thioxoimidazolidin-4-one (Example 16), 3 cm³ of ethanol and 311 mg of 1-cyclopropylmethanamine. After forty-five minutes at a temperature of 140° C. and thirty minutes at 150° C. under microwave irradiation, the solid is filtered, and then purified by preparative LC-MS [Column Xterra RP18 30×100; 5µ; with water buffered with 10 mM of ammonium hydrogen carbonate adjusted to pH 9 with ammonia/acetonitrile with gradient from 70/30 to 0/100 in 8 min], to obtain 11 mg of (5Z)-2-[(cyclopropylmethyl)amino]-5-[(5-phenyl-1H-pyrrolo[2,3-b]pyridin-3-yl)methylidene]-3,5-dihydro-4H-imidazol-4-one in the form of a yellow powder with the following characteristics:

¹H-NMR spectrum at 400 MHz: 0.22 (m, 2H); 0.43 (m, 2H); 1.11 (m, 1H); 3.26 (m partially masked, 2H); 6.70 (s, 1H); 7.15 (m broad, 1H); 7.38 (t, J=7.5 Hz, 1H); 7.49 (t, J=7.5 Hz, 2H); 7.77 (d broad, J=7.5 Hz, 2H); 8.17 (s broad, 1H); 8.53 (s broad, 1H); 9.17 (m spread out, 1H); 10.4 (m spread out, 1H); 12.0 (m spread out, 1H).

HPLC-MS-DAD-ELSD: 358(+)=(M+H)(+); 356(−)=(M−H)(−).

EXAMPLE 39

(5Z)-2-morpholin-4-yl-5-[(5-phenyl-1H-pyrrolo[2,3-b]pyridin-3-yl)methylidene]-3,5-dihydro-4H-imidazol-4-one (5Z)-2-morpholin-4-yl-5-[(5-phenyl-1H-pyrrolo[2,3-b]pyridin-3-yl)methylidene]-3,5-dihydro-4H-imidazol-4-one can be prepared as in Example 7, but from 200 mg of (5Z)-5-[(5-phenyl-1H-pyrrolo[2,3-b]pyridin-3-yl)methylene]-2-thioxoimidazolidin-4-one (Example 16), 2 cm³ of ethanol and 544 mg of morpholine. After thirty minutes at a temperature of 160° C. under microwave irradiation, then filtration of the solid, 160 mg of (5Z)-2-morpholin-4-yl-5-[(5-phenyl-1H-pyrrolo[2,3-b]pyridin-3-yl)methylidene]-3,5-dihydro-4H-imidazol-4-one is obtained in the form of a yellow powder with the following characteristics:
Melting point: 361° C.

¹H-NMR spectrum at 400 MHz: from 3.50 to 3.75 (m, 8H); 6.80 (s, 1H); 7.38 (t, J=7.5 Hz, 1H); 7.49 (t, J=7.5 Hz, 2H); 7.76 (d, J=7.5 Hz, 2H); 8.21 (s, 1H); 8.57 (d, J=2.0 Hz, 1H); 9.12 (s broad, 1H); 11.15 (m spread out, 1H); 12.1 (s broad, 1H).

HPLC-MS-DAD-ELSD: 374(+)=(M+H)(+); 372(−)=(M−H)(−).

EXAMPLE 40

(5Z)-5-[(5-phenyl-1H-pyrrolo[2,3-b]pyridin-3-yl)methylidene]-2-piperidin-1-yl-3,5-dihydro-4H-imidazol-4-one (5Z)-5-[(5-phenyl-1H-pyrrolo[2,3-b]pyridin-3-yl)methylidene]-2-piperidin-1-yl-3,5-dihydro-4H-imidazol-4-one can be prepared as in Example 7, but from 200 mg of (5Z)-5-[(5-phenyl-1H-pyrrolo[2,3-b]pyridin-3-yl)methylene]-2-thioxoimidazolidin-4-one (Example 16), 2 cm³ of ethanol and 531 mg of piperidine. After thirty minutes at a temperature of 160° C. under microwave irradiation, then filtration of the solid, 137 mg of (5Z)-5-[(5-phenyl-1H-pyrrolo[2,3-b]pyridin-3-yl)methylidene]-2-piperidin-1-yl-3,5-dihydro-4H-imidazol-4-one is obtained in the form of a yellow powder with the following characteristics:
Melting point: 307° C.

¹H-NMR spectrum at 400 MHz: from 1.50 to 1.69 (m, 6H); 3.59 (m, 4H); 6.71 (s, 1H); 7.38 (t, J=7.5 Hz, 1H); 7.49 (t, J=7.5 Hz, 2H); 7.75 (d, J=7.5 Hz, 2H); 8.15 (s, 1H); 8.55 (d, J=2.0 Hz, 1H); 9.20 (s broad, 1H); 11.0 (m spread out, 1H); 12.05 (s broad, 1H).

HPLC-MS-DAD-ELSD: 372(+)=(M+H)(+); 370(−)=(M−H)(−).

EXAMPLE 41

(5Z)-2-(4-methylpiperazin-1-yl)-5-[(5-phenyl-1H-pyrrolo[2,3-b]pyridin-3-yl)methylidene]-3,5-dihydro-4H-imidazol-4-one (5Z)-2-(4-methylpiperazin-1-yl)-5-[(5-phenyl-1H-pyrrolo[2,3-b]pyridin-3-yl)methylidene]-3,5-dihydro-4H-imidazol-4-one can be prepared as in Example 7, but from 200 mg of (5Z)-5-[(5-phenyl-1H-pyrrolo[2,3-b]pyridin-3-yl)methylene]-2-thioxoimidazolidin-4-one (Example 16), 2 cm³ of ethanol and 625 mg of 4-methylpiperazine. After forty minutes at a temperature of 160° C. under microwave irradiation, then filtration of the solid, 140 mg of (5Z)-2-(4-methylpiperazin-1-yl)-5-[(5-phenyl-1H-pyrrolo[2,3-b]pyridin-3-yl)methylidene]-3,5-dihydro-4H-imidazol-4-one is obtained in the form of a yellow powder with the following characteristics:
Melting point: 304° C.

¹H-NMR spectrum at 400 MHz: 2.23 (s, 3H); 2.40 (m, 4H); 3.59 (m, 4H); 6.78 (s, 1H); 7.38 (t, J=7.5 Hz, 1H); 7.49 (t, J=7.5 Hz, 2H); 7.76 (d, J=7.5 Hz, 2H); 8.19 (s, 1H); 8.55 (d, J=2.0 Hz, 1H); 9.15 (s broad, 1H); 11.1 (m spread out, 1H); 12.1 (s broad, 1H).

HPLC-MS-DAD-ELSD: 387(+)=(M+H)(+); 385(−)=(M−H)(−).

EXAMPLE 42

(5Z)-2-azepan-1-yl-5-[(5-phenyl-1H-pyrrolo[2,3-b]pyridin-3-yl)methylidene]-3,5-dihydro-4H-imidazol-4-one (5Z)-2-azepan-1-yl-5-[(5-phenyl-1H-pyrrolo[2,3-b]pyridin-3-yl)methylidene]-3,5-dihydro-4H-imidazol-4-one can be prepared as in Example 7, but from 200 mg of (5Z)-5-[(5-phenyl-1H-pyrrolo[2,3-b]pyridin-3-yl)methylene]-2-thioxoimidazolidin-4-one (Example 16), 2 cm³ of ethanol and 619 mg of azepane. After forty minutes at a temperature of 160° C. under microwave irradiation, then filtration of the solid, 90 mg of (5Z)-2-azepan-1-yl-5-[(5-phenyl-1H-pyrrolo[2,3-b]pyridin-3-yl)methylidene]-3,5-dihydro-4H-imidazol-4-one is obtained in the form of a yellow powder with the following characteristics:
Melting point: 302° C.

¹H-NMR spectrum at 400 MHz: from 1.47 to 1.78 (m, 8H); from 3.53 to 3.78 (m spread out, 4H); 6.69 (s, 1H); 7.38 (t, J=7.5 Hz, 1H); 7.49 (t, J=7.5 Hz, 2H); 7.73 (d, J=7.5 Hz, 2H); 8.14 (s, 1H); 8.53 (s broad, 1H); 9.18 (s broad, 1H); 11.0 (m spread out, 1H); 12.0 (s broad, 1H).

HPLC-MS-DAD-ELSD: 386(+)=(M+H)(+); 384(−)=(M−H)(−).

EXAMPLE 43

(5Z)-2-[(cyclopropylmethyl)amino]-5-[(5-methyl-1H-pyrrolo[2,3-b]pyridin-3-yl)methylidene]-3,5-dihydro-4H-imidazol-4-one (5Z)-2-[(cyclopropylmethyl)amino]-5-[(5-methyl-1H-pyrrolo[2,3-b]pyridin-3-yl)methylidene]-3,5-dihydro-4H- imidazol-4-one can be prepared as in Example 7, but from 240 mg of (5Z)-5-[(5-methyl-1H-pyrrolo[2,3-b]pyridin-3-yl)methylidene]-2-thioxoimidazolidin-4-one (Example 17), 4 cm³ of ethanol and 661 mg of 1-cyclopropylmethanamine. After thirty-five minutes at a temperature of 160° C. under microwave irradiation, then filtration of the solid, 61 mg of (5Z)-2-[(cyclopropylmethyl)amino]-5-[(5-methyl-1H-pyrrolo[2,3-b]pyridin-3-yl)methylidene]-3,5-dihydro-4H-imidazol-4-one is obtained in the form of a yellow powder with the following characteristics:
Melting point: 319-320° C.
¹H-NMR spectrum at 400 MHz: 0.29 (m, 2H); 0.48 (m, 2H); 1.16 (m, 1H); 2.40 (s, 3H); 3.23 (t, J=6.0 Hz, 2H); 6.59 (s, 1H); 7.19 (m spread out, 1H); 8.09 (s, 1H); 8.12 (s, 1H); 8.49 (s, 1H); 10.25 (m spread out, 1H); 11.8 (m spread out, 1H).
HPLC-MS-DAD-ELSD: 296(+)=(M+H)(+); 294(−)=(M−H)(−).

EXAMPLE 44

(5Z)-2-[(2-methylpropyl)amino]-5-[(5-methyl-1H-pyrrolo[2,3-b]pyridin-3-yl)methylidene]-3,5-dihydro-4H-imidazol-4-one (5Z)-2-[(2-methylpropyl)amino]-5-[(5-methyl-1H-pyrrolo[2,3-b]pyridin-3-yl)methylidene]-3,5-dihydro-4H-imidazol-4-one can be prepared as in Example 7, but from 240 mg of (5Z)-5-[(5-methyl-1H-pyrrolo[2,3-b]pyridin-3-yl)methylidene]-2-thioxoimidazolidin-4-one (Example 17), 4 cm³ of ethanol and 680 mg of 2-methylpropylamine. After thirty-five minutes at a temperature of 160° C. under microwave irradiation, then filtration of the solid, 95 mg of (5Z)-2-[(2-methylpropyl)amino]-5-[(5-methyl-1H-pyrrolo[2,3-b]pyridin-3-yl)methylidene]-3,5-dihydro-4H-imidazol-4-one is obtained in the form of a yellow powder with the following characteristics:
Melting point: 338-339° C.
¹H-NMR spectrum at 400 MHz: 0.93 (d, J=7.0 Hz, 6H); 1.94 (m, 1H); 2.40 (s, 3H); 3.19 (t broad, J=6.0 Hz, 2H); 6.58 (s, 1H); 7.15 (m spread out, 1H); 8.09 (s, 1H); 8.11 (s, 1H); 8.51 (s broad, 1H); 11.1 (m spread out, 1H); 11.75 (s broad, 1H).
HPLC-MS-DAD-ELSD: 298(+)=(M+H)(+); 296(−)=(M−H)(−).

EXAMPLE 45

(5Z)-5-[(5-methyl-1H-pyrrolo[2,3-b]pyridin-3-yl)methylidene]-2-piperidin-1-yl-3,5-dihydro-4H-imidazol-4-one (5Z)-5-[(5-methyl-1H-pyrrolo[2,3-b]pyridin-3-yl)methylidene]-2-piperidin-1-yl-3,5-dihydro-4H-imidazol-4-one can be prepared as in Example 7, but from 240 mg of (5Z)-5-[(5-methyl-1H-pyrrolo[2,3-b]pyridin-3-yl)methylidene]-2-thioxoimidazolidin-4-one (Example 17), 4 cm³ of ethanol and 791 mg of piperidine. After forty minutes at a temperature of 160° C. under microwave irradiation, then filtration of the solid, 138 mg of (5Z)-5-[(5-methyl-1H-pyrrolo[2,3-b]pyridin-3-yl)methylidene]-2-piperidin-1-yl-3,5-dihydro-4H-imidazol-4-one is obtained in the form of a yellow powder with the following characteristics:
Melting point: 320-321° C.
¹H-NMR spectrum at 400 MHz: from 1.53 to 1.69 (m, 6H); 2.39 (s, 3H); 3.58 (m, 4H); 6.61 (s, 1H); 8.09 (s, 1H); 8.14 (s broad, 1H); 8.39 (m spread out, 1H); 11.0 (m very broad, 1H); 11.8 (m spread out, 1H).
HPLC-MS-DAD-ELSD: 310(+)=(M+H)(+); 308(−)=(M−H)(−).

EXAMPLE 46

(5Z)-5-[(5-methyl-1H-pyrrolo[2,3-b]pyridin-3-yl)methylidene]-2-(4-phenylpiperazin-1-yl)-3,5-dihydro-4H-imidazol-4-one (5Z)-5-[(5-methyl-1H-pyrrolo[2,3-b]pyridin-3-yl)methylidene]-2-(4-phenylpiperazin-1-yl)-3,5-dihydro-4H-imidazol-4-one can be prepared as in Example 7, but from 240 mg of (5Z)-5-[(5-methyl-1H-pyrrolo[2,3-b]pyridin-3-yl)methylidene]-2-thioxoimidazolidin-4-one (Example 17), 4 cm³ of ethanol and 1.51 g of 4-phenylpiperazine. After thirty minutes at a temperature of 160° C. under microwave irradiation, the solid is filtered then taken up in 50 cm³ of ethanol, filtered and dried under vacuum to obtain 166 mg of (5Z)-5-[(5-methyl-1H-pyrrolo[2,3-b]pyridin-3-yl)methylidene]-2-(4-phenylpiperazin-1-yl)-3,5-dihydro-4H-imidazol-4-one in the form of a yellow powder with the following characteristics:
Melting point: 331-332° C.
¹H-NMR spectrum at 400 MHz: 2.41 (s, 3H); 3.27 (m, 4H); 3.73 (m, 4H); 6.69 (s, 1H); 6.82 (t, J=7.5 Hz, 1H); 7.01 (d, J=7.5 Hz, 2H); 7.25 (t, J=7.5 Hz, 2H); 8.10 (s, 1H); 8.21 (s, 1H); 8.39 (s, 1H); 11.15 (m very broad, 1H); 11.9 (s, 1H).
HPLC-MS-DAD-ELSD: 387(+)=(M+H)(+); 385(−)=(M−H)(−).

EXAMPLE 47

(5Z)-2-azepan-1-yl-5-[(5-methyl-1H-pyrrolo[2,3-b]pyridin-3-yl)methylidene]-3,5-dihydro-4H-imidazol-4-one (5Z)-2-azepan-1-yl-5-[(5-methyl-1H-pyrrolo[2,3-b]pyridin-3-yl)methylidene]-3,5-dihydro-4H-imidazol-4-one can be prepared as in Example 7 but from 240 mg of (5Z)-5-[(5-methyl-1H-pyrrolo[2,3-b]pyridin-3-yl)methylidene]-2-thioxoimidazolidin-4-one (Example 17), 4 cm³ of ethanol and 922 mg of azepane. After thirty minutes at a temperature of 160° C. under microwave irradiation, then filtration of the solid, 34 mg of (5Z)-2-azepan-1-yl-5-[(5-methyl-1H-pyrrolo[2,3-b]pyridin-3-yl)methylidene]-3,5-dihydro-4H-imidazol-4-one is obtained in the form of a brown powder with the following characteristics:
Melting point: 324-326° C.
¹H-NMR spectrum at 400 MHz: 1.54 (m, 4H); 1.76 (s broad, 4H); 2.39 (s, 3H); 3.62 (s broad, 4H); 6.57 (s, 1H); 8.10 (m, 2H); 8.51 (s broad, 1H); 10.72 (s broad, 1H); 11.77 (s broad, 1H).

EXAMPLE 48

(5Z)-2-[(cyclopropylmethyl)amino]-5-{[5-(trifluoromethyl)-1H-pyrrolo[2,3-b]pyridin-3-yl]methylidene}-3,5-dihydro-4H-imidazol-4-one (5Z)-2-[(cyclopropylmethyl)amino]-5-{[5-(trifluoromethyl)-1H-pyrrolo[2,3-b]pyridin-3-yl]methylidene}-3,5-dihydro-4H-imidazol-4-one can be prepared as in Example 7, but from 70 mg of (5Z)-2-thioxo-5-{[5-(trifluoromethyl)-1H-pyrrolo[2,3-b]pyridin-3-yl]methylidene}imidazolidin-4-one (Example 18), 3 cm³ of ethanol and 159 mg of 1-cyclopropylmethanamine. After thirty minutes at a temperature of 160° C. under microwave irradiation, then filtration of the solid, 32 mg of (5Z)-2-[(cyclopropylmethyl)amino]-5-{[5-(trifluoromethyl)-1H-pyrrolo[2,3-b]pyridin-3-yl]methylidene}-3,5-dihydro-4H-imidazol-4-one is obtained in the form of a yellow powder with the following characteristics:
Melting point: 350° C.
$^1$H-NMR spectrum at 400 MHz: 0.27 (m, 2H); 0.48 (m, 2H); 1.13 (m, 1H); 3.25 (t, J=6.0 Hz, 2H); 6.62 (s, 1H); 7.33 (m spread out, 1H); 8.19 (s, 1H); 8.57 (s broad, 1H); 9.71 (m spread out, 1H); 10.6 (m spread out, 1H); 12.4 (m spread out, 1H).
HPLC-MS-DAD-ELSD: 350(+)=(M+H)(+).

EXAMPLE 49

(5Z)-2-azepan-1-yl-5-{[5-(trifluoromethyl)-1H-pyrrolo[2,3-b]pyridin-3-yl]methylidene}-3,5-dihydro-4H-imidazol-4-one (5Z)-2-azepan-1-yl-5-{[5-(trifluoromethyl)-1H-pyrrolo[2,3-b]pyridin-3-yl]methylidene}-3,5-dihydro-4H-imidazol-4-one can be prepared as in Example 7, but from 70 mg of (5Z)-2-thioxo-5-{[5-(trifluoromethyl)-1H-pyrrolo[2,3-b]pyridin-3-yl]methylidene}imidazolidin-4-one (Example 18), 3 cm$^3$ of ethanol and 222 mg of azepane. After fifty minutes at a temperature of 160° C. under microwave irradiation, then filtration of the solid, 22 mg of (5Z)-2-azepan-1-yl-5-{[5-(trifluoromethyl)-1H-pyrrolo[2,3-b]pyridin-3-yl]methylidene}-3,5-dihydro-4H-imidazol-4-one is obtained in the form of a yellow powder with the following characteristics:
Melting point: 340° C.
$^1$H-NMR spectrum at 400 MHz: 1.53 (m, 4H); 1.74 (m broad, 4H); from 3.40 to 3.90 (m spread out, 4H); 6.61 (s, 1H); 8.18 (s, 1H); 8.56 (s broad, 1H); 9.77 (m spread out, 1H); 11.1 (m spread out, 1H); 12.4 (m spread out, 1H).
HPLC-MS-DAD-ELSD: 378(+)=(M+H)(+); 376(−)=(M−H)(−).

EXAMPLE 50

(5Z)-2-[(cyclopropylmethyl)amino]-5-{[5-(phenylamino)-1H-pyrrolo[2,3-b]pyridin-3-yl]methylidene}-3,5-dihydro-4H-imidazol-4-one (5Z)-2-[(cyclopropylmethyl)amino]-5-{[5-(phenylamino)-1H-pyrrolo[2,3-b]pyridin-3-yl]methylidene}-3,5-dihydro-4H-imidazol-4-one can be prepared as in Example 7, but from 70 mg of (5Z)-5-[(5-phenylamino-1H-pyrrolo[2,3-b]pyridin-3-yl)methylene]-2-thioxoimidazolidin-4-one (Example 21), 1 cm$^3$ of ethanol and 148 mg of 1-cyclopropylmethanamine. After thirty minutes at a temperature of 160° C. under microwave irradiation, the yellow solid precipitated in the reaction mixture is filtered to obtain 18 mg of (5Z)-5-[(5-phenylamino-1H-pyrrolo[2,3-b]pyridin-3-yl)methylene]-2-thioxoimidazolidin-4-one in the form of orange powder with the following physical characteristics:
$^1$H-NMR spectrum at 400 MHz: 0.16 (m, 2H); 0.39 (m, 2H); 1.01 (m, 1H); 3.08 (t, J=6.0 Hz, 2H); 6.54 (s, 1H); 6.71 (t, J=7.5 Hz, 1H); 6.93 (d, J=7.5 Hz, 2H); 7.03 (m spread out, 1H); 7.18 (t, J=7.5 Hz, 2H); 7.91 (s, 1H); 8.05 (s, 1H); 8.11 (s, 1H); 8.50 (s, 1H); 10.3 (m spread out, 1H); 11.8 (m spread out, 1H).
LC-MS (1): retention time 3.55 min; HPLC-MS-DAD-ELSD: 371(+)=(M+H)(+); 373(−)=(M−H)(−).

EXAMPLE 51

(5Z)-2-[(cyclopropylmethyl)amino]-5-[(5-morpholin-4-yl-1H-pyrrolo[2,3-b]pyridin-3-yl)methylidene]-3,5-dihydro-4H-imidazol-4-one (5Z)-2-[(cyclopropylmethyl)amino]-5-[(5-morpholin-4-yl-1H-pyrrolo[2,3-b]pyridin-3-yl)methylidene]-3,5-dihydro-4H-imidazol-4-one can be prepared as in Example 7, but from 160 mg of (5Z)-5-[(5-morpholin-4-yl-1H-pyrrolo[2,3-b]pyridin-3-yl)methylidene]-2-thioxoimidazolidin-4-one (Example 22), 2 cm$^3$ of ethanol and 345 mg of 1-cyclopropylmethanamine. After one hour at a temperature of 160° C. under microwave irradiation, the yellow solid precipitated in the reaction mixture is filtered to obtain 100 mg of (5Z)-2-[(cyclopropylmethyl)amino]-5-[(5-morpholin-4-yl-1H-pyrrolo[2,3-b]pyridin-3-yl)methylidene]-3,5-dihydro-4H-imidazol-4-one in the form of a yellow powder with the following physical characteristics:
Melting point: 331° C.
$^1$H-NMR spectrum at 400 MHz: 0.29 (m, 2H); 0.48 (m, 2H); 1.12 (m, 1H); 3.13 (m, 4H); 3.22 (t, J=6.0 Hz, 2H); 3.79 (m, 4H); 6.61 (s 1H); 7.11 (m broad, 1H); 8.08 (m, 2H); 8.38 (s broad, 1H); 10.3 (m spread out, 1H); 11.7 (s broad, 1H).
HPLC-MS-DAD-ELSD: 367=(M+H)(+); 365(−)=(M−H)(−).

EXAMPLE 52

(5Z)-2-[(cyclopropylmethyl)amino]-5-[(5-thiophen-3-yl-1H-pyrrolo[2,3-b]pyridin-3-yl)methylidene]-3,5-dihydro-4H-imidazol-4-one (5Z)-2-[(cyclopropylmethyl)amino]-5-[(5-thiophen-3-yl-1H-pyrrolo[2,3-b]pyridin-3-yl)methylidene]-3,5-dihydro-4H-imidazol-4-one can be prepared as follows:
A microwave oven reactor is charged with 150 mg of (5Z)-5-[(5-bromo-1H-pyrrolo[2,3-b]pyridin-3-yl)methylene]-2-[(cyclopropylmethyl)amino]-3,5-dihydro-4H-imidazol-4-one (Example 33), 4.8 cm$^3$ of dioxan, 1.2 cm$^3$ of water, 80 mg of thiophene-3-boronic acid, 540 mg of caesium carbonate and 15 mg of 1,1'-bis(diphenylphosphino)-ferrocenedichloropalladium(II). The reactor is sealed and irradiated for 2×thirty minutes at 145° C. After adding 80 mg of thiophene-3-boronic acid and 14 mg of catalyst, the reaction mixture is irradiated again for 30 minutes at 150° C. The reaction mixture is concentrated under vacuum, taken up in 20 cm$^3$ of water and 20 cm$^3$ of ethyl acetate. 85 mg of insoluble matter is filtered. The filtrate is decanted and re-extracted with ethyl acetate. The organic phases are dried over magnesium sulphate, then concentrated under vacuum to give 92 mg of a brown solid. The two solid residues isolated, containing the expected product, are combined and then purified by preparative LC-MS [Column Xterra RP18 30×100; 5μ; with water buffered with 10 mM of ammonium hydrogen carbonate adjusted to pH 9 with ammonia/acetonitrile with gradient from 70/30 to 0/100 in 8 min] to obtain 25 mg of (5Z)-(5Z)-2-[(cyclopropylmethyl)amino]-5-[(5-thiophen-3-yl-1H-pyrrolo[2,3-b]pyridin-3-yl)methylidene]-3,5-dihydro-4H-imidazol-4-one in the form of brown powder with the following physical characteristics:
$^1$H-NMR spectrum at 400 MHz: 0.29 (m, 2H); 0.49 (m, 2H); 1.16 (m, 1H); 3.27 (m partially masked, 2H); 6.71 (s, 1H); 7.19 (m broad, 1H); 7.69 (m, 2H); 7.91 (s broad, 1H); 8.19 (s broad, 1H); 8.64 (d, J=2.0 Hz, 1H); 9.07 (s broad, 1H); 10.4 (m spread out, 1H); 11.95 (m spread out, 1H).
HPLC-MS-DAD-ELSD: 358(+)=(M+H)(+); 356(−)=(M−H)(−).

EXAMPLE 53

(5Z)-2-[(cyclopropylmethyl)amino]-5-{[5-(4-piperazin-1-ylphenyl)-1H-pyrrolo[2,3-b]pyridin-3-yl]methylidene}-3,5-dihydro-4H-imidazol-4-one a) (5Z)-2-[(cyclopropylmethyl)amino]-5-{[5-(4-piperazin-1-ylphenyl)-1H-pyrrolo[2,3-b]pyridin-3-yl]methylidene}-3,5-dihydro-4H-imidazol-4-one can be prepared as follows:

Stir 140 mg of 1,1-dimethylethyl 4-(4-{3-[(Z)-{2-[(cyclopropylmethyl)amino]-5-oxo-1,5-dihydro-4H-imidazol-4-ylidene}methyl]-1H-pyrrolo[2,3-b]pyridin-5-yl}phenyl)piperazine-1-carboxylate in 3 cm³ of a 4M solution of hydrochloric acid in dioxan for two hours at room temperature. The resultant precipitate is filtered, then purified on 5 g of column SCX with elution with methanol then with a 2M solution of ammonia in methanol, to obtain 22 mg of (5Z)-2-[(cyclopropylmethyl)amino]-5-{[5-(4-piperazin-1-ylphenyl)-1H-pyrrolo[2,3-b]pyridin-3-yl]methylidene}-3,5-dihydro-4H-imidazol-4-one in the form of a yellow powder with the following physical characteristics:

¹H-NMR spectrum at 400 MHz: 0.25 (m, 2H); 0.45 (m, 2H); 1.12 (m, 1H); 2.91 (m, 4H); 3.13 (m, 4H); from 3.20 to 3.40 (m partially masked, 2H); 6.69 (s, 1H); 7.01 (d, J=8.5 Hz, 2H); 7.15 (m spread out, 1H); 7.61 (d, J=8.5 Hz, 2H); 8.13 (s, 1H); 8.48 (d, J=1.5 Hz, 1H); 9.05 (s broad, 1H); 10.35 (m spread out, 1H); 11.95 (s broad, 1H).

HPLC-MS-DAD-ELSD: 442(+)=(M+H)(+).

b) 1,1-dimethylethyl 4-(4-{3-[(Z)-{2-[(cyclopropylmethyl)amino]-5-oxo-1,5-dihydro-4H-imidazol-4-ylidene}methyl]-1H-pyrrolo[2,3-b]pyridin-5-yl}phenyl)piperazine-1-carboxylate can be prepared as in Example 52, but from 80 mg of (5Z)-5-[(5-bromo-1H-pyrrolo[2,3-b]pyridin-3-yl)methylene]-2-[(cyclopropylmethyl)amino]-3,5-dihydro-4H-imidazol-4-one (Example 33) in 2.4 cm³ of dioxan and 0.8 cm³ of water, 100 mg of (4-{4-[(1,1-dimethylethoxy)carbonyl]piperazin-1-yl}phenyl) boronic acid, 280 mg of caesium carbonate and 15 mg of 1,1'-bis(diphenylphosphino)ferrocenedichloropalladium (II). 110 mg of 1,1-dimethylethyl 4-(4-{3-[(Z)-{2-[(cyclopropylmethyl)amino]-5-oxo-1,5-dihydro-4H-imidazol-4-ylidene}methyl]-1H-pyrrolo[2,3-b]pyridin-5-yl}phenyl)piperazine-1-carboxylate is obtained in the form of powder with the following physical characteristics:

¹H-NMR spectrum at 400 MHz: 0.25 (s broad, 2H); 0.44 (s broad, 2H); 1.12 (s broad, 1H); 1.45 (s, 9H); 3.17 (m, 4H); 3.27 (partially masked, 2H); 3.49 (m, 4H); 6.68 (s, 1H); 7.06 (d broad, J=7.8 Hz, 2H); 7.17 (s broad, 1H); 7.64 (d broad, J=7.8 Hz, 2H); 8.14 (s, 1H); 8.49 (s, 1H); 9.05 (s broad, 1H); 10.40 (s broad, 1H); 11.94 (s broad, 1H).

Rf: 0.24 (dichloromethane/ethyl acetate eluent 90/10).

LC-MS-DAD-ELSD: 540 (−)=(M−H)(−); 542(+)=(M+H)(+).

EXAMPLE 54

(5Z)-5-[(5-benzyl-1H-pyrrolo[2,3-b]pyridin-3-yl)methylidene]-2-[(cyclopropylmethyl)amino]-3,5-dihydro-4H-imidazol-4-one 5Z)-5-[(5-benzyl-1H-pyrrolo[2,3-b]pyridin-3-yl)methylidene]-2-[(cyclopropylmethyl)amino]-3,5-dihydro-4H-imidazol-4-one can be prepared as in Example 7, but from 60 mg of (5Z)-5-[(5-benzyl-1H-pyrrolo[2,3-b]pyridin-3-yl)methylidene]-2-thioxoimidazolidin-4-one (Example 23), 1 cm³ of ethanol and 13 mg of 1-cyclopropylmethanamine. After thirty minutes at a temperature of 160° C. under microwave irradiation, then filtration of the solid, 31 mg of (5Z)-5-[(5-benzyl-1H-pyrrolo[2,3-b]pyridin-3-yl)methylidene]-2-[(cyclopropylmethyl)amino]-3,5-dihydro-4H-imidazol-4-one is obtained in the form of a yellow powder with the following characteristics:

Melting point: 315-318° C.

¹H-NMR spectrum at 400 MHz: 0.28 (m, 2H); 0.47 (m, 2H); 1.14 (m, 1H); 3.21 (m, 2H); 4.03 (s, 2H); 6.56 (s, 1H); from 7.11 to 7.33 (m, 5H); 8.11 (s, 1H); 8.18 (s, 1H); 8.58 (s, 1H); 10.1 (m spread out, 1H); 11.85 (m spread out, 1H).

UPLC-MS-DAD-ELSD: 372(+)=(M+H)(+); 370(−)=(M−H)(−).

EXAMPLE 55

(5Z)-2-amino-3-[3-(dimethylamino)propyl]-5-(1H-pyrrolo[2,3-b]pyridin-3-ylmethylidene)-3,5-dihydro-4H-imidazol-4-one (5Z)-2-amino-3-[3-(dimethylamino)propyl]-5-(1H-pyrrolo[2,3-b]pyridin-3-ylmethylidene)-3,5-dihydro-4H-imidazol-4-one can be prepared as in Example 7, but from 351 mg of (5Z)-5-[(1H-pyrrolo[2,3-b]pyridin-3-yl)methylene]-2-thioxoimidazolidin-4-one (Example 1), 2.5 cm³ of ethanol and 1.47 g of 3-dimethylamino-propylamine. After thirty minutes at a temperature of 150° C. under microwave irradiation, then concentrating under vacuum and taking up the residue in methylene chloride, filtration of the solid gives 8 mg of (5Z)-2-amino-3-[3-(dimethylamino)propyl]-5-(1H-pyrrolo[2,3-b]pyridin-3-ylmethylidene)-3,5-dihydro-4H-imidazol-4-one in the form of a yellow powder with the following characteristics:

¹H-NMR spectrum at 400 MHz: 1.67 (m, 2H); 2.12 (s, 6H); 2.20 (t, J=7.0 Hz, 2H); 3.56 (t, J=7.0 Hz, 2H); 6.71 (s, 1H); 7.11 (dd, J=5.0 and 8.0 Hz, 1H); 7.33 (s broad, 2H); 8.24 (m, 2H); 8.59 (dd, J=1.5 and 8.0 Hz, 1H); 12.0 (s broad, 1H).

UPLC-MS-DAD-ELSD: 313(+)=(M+H)(+); 311(−)=(M−H)(−).

EXAMPLE 56

(5Z)-2-amino-3-(3-morpholin-4-ylpropyl)-5-(1H-pyrrolo[2,3-b]pyridin-3-ylmethylidene)-3,5-dihydro-4H-imidazol-4-one (5Z)-2-amino-3-(3-morpholin-4-ylpropyl)-5-(1H-pyrrolo[2,3-b]pyridin-3-ylmethylidene)-3,5-dihydro-4H-imidazol-4-one can be prepared as in Example 7, but from 310 mg of (5Z)-5-[(1H-pyrrolo[2,3-b]pyridin-3-yl)methylene]-2-thioxoimidazolidin-4-one (Example 1), 2.5 cm³ of ethanol and 310 mg of 3-morpholinopropylamine. After fifty minutes at a temperature of 160° C. under microwave irradiation, then filtration of the solid, 86 mg of (5Z)-2-amino-3-(3-morpholin-4-ylpropyl)-5-(1H-pyrrolo[2,3-b]pyridin-3-ylmethylidene)-3,5-dihydro-4H-imidazol-4-one is obtained in the form of a yellow powder with the following characteristics:

¹H-NMR spectrum at 400 MHz: 1.67 (m, 2H); 2.2-2.4 (m, 6H); 3.6 (m, 6H); 6.7 (s, 1H); 7.15 (dd, J=5.0 and 8.0 Hz, 1H); 7.35 (s broad, 2H); 8.25 (m, 2H); 8.6 (dd, J=1.5 and 8.0 Hz, 1H); 12.0 (s broad, 1H).

HPLC-MS-DAD-ELSD: 355(+)=(M+H)(+).

EXAMPLE 57

(5Z)-2-amino-3-(3-ethoxypropyl)-5-(1H-pyrrolo[2,3-b]pyridin-3-ylmethylidene)-3,5-dihydro-4H-imidazol-4-one (5Z)-2-amino-3-(3-ethoxypropyl)-5-(1H-pyrrolo[2,3-b]pyridin-3-ylmethylidene)-3,5-dihydro-4H-imidazol-4-one can be prepared as in Example 7, but from 350 mg of (5Z)-5-[(1H-pyrrolo[2,3-b]pyridin-3-yl)methylene]-2-thioxoimidazolidin-4-one (Example 1), 2.5 cm³ of ethanol and 350 mg of 3-ethoxypropylamine. After fifty minutes at a temperature of 160° C. under microwave irradiation, then filtration of the solid, 28 mg of (5Z)-2-amino-3-(3-ethoxypropyl)-5-(1H-pyrrolo[2,3-b]pyridin-3-ylmethylidene)-3,5-dihydro-4H-imidazol-4-one is obtained in the form of a yellow powder with the following characteristics:

$^1$H-NMR spectrum at 400 MHz: 1.12 (t, J=7 Hz, 3H); 1.67 (m, 2H); 3.3-3.5 (m, 4H); 3.65 (t, J=7 Hz, 2H); 6.72 (s, 1H); 7.15 (dd, J=5.0 and 8.0 Hz, 1H); 7.25 (s broad, 2H); 8.25 (s broad, 2H); 8.6 (dd, J=1.5 and 8.0 Hz, 1H); 12.0 (s broad, 1H).

HPLC-MS-DAD-ELSD: 314(+)=(M+H)(+); 312(−)=(M−H)(−).

EXAMPLE 58

(5Z)-2-amino-3-(3-pyrrolidin-1-ylpropyl)-5-(1H-pyrrolo[2,3-b]pyridin-3-ylmethylidene)-3,5-dihydro-4H-imidazol-4-one (5Z)-2-amino-3-(3-pyrrolidin-1-ylpropyl)-5-(1H-pyrrolo[2,3-b]pyridin-3-ylmethylidene)-3,5-dihydro-4H-imidazol-4-one can be prepared as in Example 7, but from 366 mg of (5Z)-5-[(1H-pyrrolo[2,3-b]pyridin-3-yl)methylene]-2-thioxoimidazolidin-4-one (Example 1), 2.5 cm³ of ethanol and 1.92 g of 3-(1-pyrrolidyl)propylamine. After fifty minutes at a temperature of 160° C. under microwave irradiation, then filtration of the solid, 58 mg of (5Z)-2-amino-3-(3-pyrrolidin-1-ylpropyl)-5-(1H-pyrrolo[2,3-b]pyridin-3-ylmethylidene)-3,5-dihydro-4H-imidazol-4-one is obtained in the form of a yellow powder with the following characteristics:

$^1$H-NMR spectrum at 400 MHz: 1.69 (m, 6H); 2.39 (t, J=6.5 Hz, 2H); 2.42 (m, 4H); 3.59 (t, J=6.5 Hz, 2H); 6.71 (s, 1H); 7.11 (dd, J=5.0 and 8.0 Hz, 1H); 7.40 (s broad, 2H); 8.23 (m, 2H); 8.59 (d broad, J=8.0 Hz, 1H); 12.0 (m spread out, 1H).

HPLC-MS-DAD-ELSD: 339(+)=(M+H)(+); 337(−)=(M−H)(−).

EXAMPLE 59

(5Z)-2-[(cyclopropylmethyl)amino]-3-phenyl-5-(1H-pyrrolo[2,3-b]pyridin-3-ylmethylidene)-3,5-dihydro-4H-imidazol-4-one (5Z)-2-[(cyclopropylmethyl)amino]-3-phenyl-5-(1H-pyrrolo[2,3-b]pyridin-3-ylmethylidene)-3,5-dihydro-4H-imidazol-4-one can be prepared as in Example 7, but from 128 mg of (5Z/E)-3-phenyl-5-(1H-pyrrolo[2,3-b]pyridin-3-ylmethylidene)-2-thioxoimidazolidin-4-one (Example 24), 3.5 cm³ of ethanol and 284 mg of 1-cyclopropylmethanamine. After thirty minutes at a temperature of 160° C. under microwave irradiation and purification by preparative LC-MS [Column Xterra RP18 30×100; 5μ; with water buffered with 10 mM of ammonium hydrogen carbonate adjusted to pH 9 with ammonia/acetonitrile with gradient from 70/30 to 0/100 in 8 min], 34 mg of (5Z)-2-[(cyclopropylmethyl)amino]-3-phenyl-5-(1H-pyrrolo[2,3-b]pyridin-3-ylmethylidene)-3,5-dihydro-4H-imidazol-4-one is obtained in the form of yellow lyophilizate with the following characteristics:

$^1$H-NMR spectrum at 400 MHz: 0.31 (m, 2H); 0.47 (m, 2H); 1.23 (m, 1H); 3.30 (m partially masked, 2H); 6.84 (s, 1H); 7.00 (t, J=6.0 Hz, 1H); 7.13 (dd, J=5.0 and 8.0 Hz, 1H); 7.35 (d, J=7.5 Hz, 2H); 7.50 (t, J=7.5 Hz, 1H); 7.58 (t, J=7.5 Hz, 2H); 8.27 (dd, J=1.5 and 5.0 Hz, 1H); 8.31 (d, J=2.0 Hz, 1H); 8.67 (d broad, J=8.0 Hz, 1H); 12.0 (s broad, 1H).

HPLC-MS-DAD-ELSD: 358(+)=(M+H)(+); 356(−)=(M−H)(−).

EXAMPLE 60

(5Z)-5-[(5-chloro-1H-pyrrolo[2,3-b]pyridin-3-yl)methylidene]-2-(methylsulphanyl)-3,5-dihydro-4H-imidazol-4-one (5Z)-5-[(5-chloro-1H-pyrrolo[2,3-b]pyridin-3-yl)methylidene]-2-(methylsulphanyl)-3,5-dihydro-4H-imidazol-4-one can be prepared as follows:
Slowly add 0.86 cm³ of a molar solution of sodium hydroxide to a mixture of 200 mg of (5Z)-5-[(5-chloro-1H-pyrrolo[2,3-b]pyridin-3-yl)methylene]-2-thioxoimidazolidin-4-one (Example 3) and 122 mg of methyl iodide in 7 cm³ of methanol at 0° C. Then stir the mixture at room temperature for two hours. The solid that forms is filtered, then dried under vacuum to obtain 175 mg of (5Z)-5-[(5-chloro-1H-pyrrolo[2,3-b]pyridin-3-yl)methylidene]-2-(methylsulphanyl)-3,5-dihydro-4H-imidazol-4-one in the form of yellow powder with the following characteristics:
Melting point: >410° C.

$^1$H-NMR spectrum at 400 MHz: 2.71 (s, 3H); 7.03 (s, 1H); 8.29 (d, J=2.0 Hz, 1H); 8.37 (s, 1H); 9.31 (s broad, 1H); from 11.4 to 12.7 (m very broad, 2H).

HPLC-MS-DAD-ELSD: 293(+)/ . . . =(M+H)(+)/ . . . 291 (−)/ . . . =(M−H)(−)/ . . . (1 chlorine atom Cl present).

EXAMPLE 61

(5Z)-2-(benzylsulphanyl)-5-[(5-chloro-1H-pyrrolo[2,3-b]pyridin-3-yl)methylidene]-3,5-dihydro-4H-imidazol-4-one (5Z)-2-(benzylsulphanyl)-5-[(5-chloro-1H-pyrrolo[2,3-b]pyridin-3-yl)methylidene]-3,5-dihydro-4H-imidazol-4-one can be prepared as in Example 60, but from 400 mg of (5Z)-5-[(5-chloro-1H-pyrrolo[2,3-b]pyridin-3-yl)methylene]-2-thioxoimidazolidin-4-one (Example 3), 270 mg of benzyl bromide, 14 cm³ of methanol at 0° C. and of 1.8 cm³ of a molar solution of sodium hydroxide. After two hours at room temperature, the solid formed is filtered to obtain 452 mg of (5Z)-2-(benzylsulphanyl)-5-[(5-chloro-1H-pyrrolo[2,3-b]pyridin-3-yl)methylidene]-3,5-dihydro-4H-imidazol-4-one in the form of yellow powder with the following characteristics:
Melting point: 313-315° C.

$^1$H-NMR spectrum at 400 MHz: 4.63 (s, 2H); 7.10 (s, 1H); from 7.23 to 7.40 (m, 3H); 7.51 (d broad, J=7.5 Hz, 2H); 8.29 (d, J=2.5 Hz, 1H); 8.43 (s, 1H); 9.20 (d, J=2.5 Hz, 1H); from 11.6 to 12.7 (m very broad, 2H).

HPLC-MS-DAD-ELSD: 369(+)/ . . . =(M+H)(+)/ . . . (1 chlorine atom Cl present).

EXAMPLE 62

(5Z)-5-[(5-chloro-1H-pyrrolo[2,3-b]pyridin-3-yl) methylidene]-2-(propylsulphanyl)-3,5-dihydro-4H-imidazol-4-one (5Z)-5-[(5-chloro-1H-pyrrolo[2,3-b]pyridin-3-yl)methylidene]-2-(propylsulphanyl)-3,5-dihydro-4H-imidazol-4-one can be prepared as in Example 60, but from 200 mg of (5Z)-5-[(5-chloro-1H-pyrrolo[2,3-b]pyridin-3-yl)methylene]-2-thioxoimidazolidin-4-one (Example 3), 146 mg of iodo-1-propane, 7 cm$^3$ of methanol at 0° C. and 0.86 cm$^3$ of a molar solution of sodium hydroxide. After stirring at room temperature overnight, the solid formed is filtered to obtain 172 mg of (5Z)-5-[(5-chloro-1H-pyrrolo[2,3-b]pyridin-3-yl)methylidene]-2-(propylsulphanyl)-3,5-dihydro-4H-imidazol-4-one in the form of yellow powder with the following characteristics:
Melting point: 316-318° C.
$^1$H-NMR spectrum at 400 MHz: 1.05 (t, J=7.6 Hz, 3H); 1.83 (sext, J=7.6 Hz, 2H); 3.33 (masked, 2H); 7.03 (s, 1H); 8.29 (d, J=2.4 Hz, 1H); 8.33 (s, 1H); 9.28 (d, J=2.4 Hz, 1H) 12.10 (s broad, 1H).

EXAMPLE 63

(5Z)-5-[(5-chloro-1H-pyrrolo[2,3-b]pyridin-3-yl) methylidene]-2-((1-methyl)ethylsulphanyl)-3,5-dihydro-4H-imidazol-4-one (5Z)-5-[(5-chloro-1H-pyrrolo[2,3-b]pyridin-3-yl)methylidene]-2-((1-methyl)ethylsulphanyl)-3,5-dihydro-4H-imidazol-4-one can be prepared as in Example 60, but from 200 mg of (5Z)-5-[(5-chloro-1H-pyrrolo[2,3-b]pyridin-3-yl)methylene]-2-thioxoimidazolidin-4-one (Example 3), 146 mg of iodo-2-propane, 7 cm$^3$ of methanol at 0° C. and 0.86 cm$^3$ of a molar solution of sodium hydroxide. The mixture is stirred at 50° C. overnight then at 70° C. for an extra day. The solid formed is then filtered to obtain 90 mg of (5Z)-5-[(5-chloro-1H-pyrrolo[2,3-b]pyridin-3-yl)methylidene]-2-((1-methyl)ethylsulphanyl)-3,5-dihydro-4H-imidazol-4-one in the form of yellow powder with the following characteristics:
Melting point: 291-293° C.
$^1$H-NMR spectrum at 400 MHz: 1.52 (d, J=6.9 Hz, 6H); 4.13 (m, 1H); 7.03 (s, 1H); 8.29 (d, J=2.4 Hz, 1H); 8.32 (s, 1H); 9.33 (d, J=2.4 Hz, 1H); 12.05 (s broad, 1H).

EXAMPLE 64

(5Z)-2-butyl-5-[(5-chloro-1H-pyrrolo[2,3-b]pyridin-3-yl)methylidene]-3,5-dihydro-4H-imidazol-4-one (5Z)-2-butyl-5-[(5-chloro-1H-pyrrolo[2,3-b]pyridin-3-yl)methylidene]-3,5-dihydro-4H-imidazol-4-one can be prepared as in Example 13, but from 131 mg of raw 2-butyl-imidazolidin-4-one and 135 mg of 5-chloro-1H-pyrrolo[2,3-b]pyridine-3-carbaldehyde to give 164 mg of (5Z)-2-butyl-5-[(5-chloro-1H-pyrrolo[2,3-b]pyridin-3-yl)methylidene]-3,5-dihydro-4H-imidazol-4-one in the form of a yellow powder with the following characteristics:
Melting point: 288-290° C.
$^1$H-NMR spectrum at 400 MHz: 0.97 (t, J=7.5 Hz, 3H); 1.42 (m, 2H); 1.78 (m, 2H); 2.57 (t, J=7.5 Hz, 2H); 7.13 (s, 1H); 8.29 (d, J=2.5 Hz, 1H); 8.33 (s, 1H); 9.38 (d, J=2.5 Hz, 1H); 11.1 (s broad, 1H); 12.5 (m spread out, 1H).
HPLC-MS-DAD-ELSD: 303(+)=(M+H)(+).

EXAMPLE 65

(5Z)-2-butyl-5-[(6-chloro-1H-pyrrolo[2,3-b]pyridin-3-yl)methylidene]-3,5-dihydro-4H-imidazol-4-one (5Z)-2-butyl-5-[(6-chloro-1H-pyrrolo[2,3-b]pyridin-3-yl)methylidene]-3,5-dihydro-4H-imidazol-4-one can be prepared as in Example 13, but from 87 mg of raw 2-butyl-imidazolidin-4-one and 90 mg of 6-chloro-1H-pyrrolo[2,3-b]pyridine-3-carbaldehyde to give 85 mg of (5Z)-2-butyl-5-[(6-chloro-1H-pyrrolo[2,3-b]pyridin-3-yl)methylidene]-3,5-dihydro-4H-imidazol-4-one in the form of a yellow powder with the following characteristics:
Melting point: 318-321° C.
$^1$H-NMR spectrum at 400 MHz: 0.94 (t, J=7.5 Hz, 3H); 1.40 (m, 2H); 1.71 (m, 2H); 2.54 (t, J=7.5 Hz, 2H); 7.13 (s, 1H); 7.24 (d, J=8.0 Hz, 1H); 8.31 (s, 1H); 9.07 (d, J=8.0 Hz, 1H); 11.1 (s broad, 1H); 12.5 (m spread out, 1H).
SM-EI: 302(+.)=(M)(+.); 260(+)=(M-C3H6)(+).

EXAMPLE 66

(5Z)-2-butyl-3-methyl-5-(1H-pyrrolo[2,3-b]pyridin-3-ylmethylidene)-3,5-dihydro-4H-imidazol-4-one a) (5Z)-2-butyl-3-methyl-5-(1H-pyrrolo[2,3-b]pyridin-3-ylmethylidene)-3,5-dihydro-4H-imidazol-4-one can be prepared as in Example 13, but from 0.63 g of 2-butyl-3-methyl-3,5-dihydro-4H-imidazol-4-one, 200 mg of 1H-pyrrolo[2,3-b]pyridine-3-carbaldehyde and 0.14 cm$^3$ of piperidine in 10 cm$^3$ of ethanol. After one hour under reflux, the mixture is cooled to room temperature and the yellow solid is filtered, washed with a little ethanol then dried under vacuum to give 323 mg of (5Z)-2-butyl-3-methyl-5-(1H-pyrrolo[2,3-b]pyridin-3-ylmethylidene)-3,5-dihydro-4H-imidazol-4-one in the form of a yellow powder with the following characteristics:
Melting point: 220-222° C.
$^1$H-NMR spectrum at 400 MHz: 0.99 (t, J=7.0 Hz, 3H); 1.50 (m, 2H); 1.80 (m, 2H); 2.68 (t, J=7.0 Hz, 2H); 3.10 (s, 3H); 7.19 (dd, J=5.0 and 8.0 Hz, 1H); 7.29 (s, 1H); 8.29 (dd, J=1.5 and 5.0 Hz, 1H); 8.38 (s, 1H); 9.01 (d broad, J=8.0 Hz, 1H); 12.4 (m spread out, 1H).
HPLC-MS-DAD-ELSD: 283(+)=(M+H)(+); 281(−)=(M−H)(−).
b) 2-butyl-3-methyl-3,5-dihydro-4H-imidazol-4-one can be prepared as follows:
Slowly add a 2M solution of methylamine in THF (12 cm$^3$) to a solution of 1.99 g of N-(1-methoxypentylidene)methylglycinate in 20 cm$^3$ of methanol. Stir the mixture at room temperature for three hours, then concentrate under vacuum to obtain 1.63 g of raw 2-butyl-3-methyl-3,5-dihydro-4H-imidazol-4-one, which is used as such in the next stage.
c) N-(1-methoxypentylidene)methylglycinate can be prepared as follows:
Stir a suspension of 2 g of methyl pentanimidoate hydrochloride and 1.67 g of methyl glycinate hydrochloride in 20 cm$^3$ of methylene chloride at 0° C. for five hours, then add 1.8 cm$^3$ of triethylamine. Stir the resultant mixture at room temperature for one hour, dilute with 10 cm$^3$ of phosphate buffer pH 7, then extract with methylene chloride (3×20 cm$^3$). The combined organic phases are dried over magnesium sulphate and concentrated under vacuum to obtain 1.99 g of N-(1-methoxypentylidene)methylglycinate.

EXAMPLE 67

(5Z)-2-(2-Phenylethyl)-5-(1H-pyrrolo[2,3-b]pyridin-3-ylmethylidene)-3,5-dihydro-4H-imidazol-4-one a) (5Z)-2-(2-phenylethyl)-5-(1H-pyrrolo[2,3-b]pyridin-3-ylmethylidene)-3,5-dihydro-4H-imidazol-4-one can be prepared as in Example 13, but from 1 g of raw 2-(2-phenylethyl)-3,5-dihydro-4H-imidazol-4-one and 0.2 g of 1H-pyrrolo[2,3-b]pyridine-3-carbaldehyde to give 244 mg of (5Z)-2-(2-phenylethyl)-5-(1H-pyrrolo[2,3-b]pyridin-3-ylmethylidene)-3,5-dihydro-4H-imidazol-4-one in the form of a yellow powder with the following characteristics:
Melting point: 270-272° C.
$^1$H-NMR spectrum at 400 MHz: 2.88 (t, J=7.5 Hz, 2H); 3.09 (t, J=7.5 Hz, 2H); 7.18 (s, 1H); 7.20 (m, 2H); 7.31 (m, 4H); 8.29 (dd, J=1.5 and 5.0 Hz, 1H); 8.35 (s, 1H); 8.89 (d broad, J=8.0 Hz, 1H); 11.2 (m spread out, 1H); 12.4 (m very broad, 1H).
HPLC-MS-DAD-ELSD: 317(+)=(M+H)(+); 315(−)=(M−H)(−).

b) 2-(2-phenylethyl)-3,5-dihydro-4H-imidazol-4-one can be prepared as in Example 13, but from 2 g of methyl 3-phenylpropanimidoate hydrochloride to obtain 2.85 g of raw 2-(2-phenylethyl)-3,5-dihydro-4H-imidazol-4-one.

c) Methyl 3-phenylpropanimidoate hydrochloride can be prepared as in Example 13, but from 5 cm$^3$ of 2-phenylethyl carbonitrile, 1.7 cm$^3$ of methanol and 4 cm$^3$ of ether. 7.5 g of methyl 3-phenylpropanimidoate hydrochloride is obtained in the form of a white solid.

EXAMPLE 68

(5Z)-2-(3-methylbutyl)-5-(1H-pyrrolo[2,3-b]pyridin-3-ylmethylidene)-3,5-dihydro-4H-imidazol-4-one a) (5Z)-2-(3-methylbutyl)-5-(1H-pyrrolo[2,3-b]pyridin-3-ylmethylidene)-3,5-dihydro-4H-imidazol-4-one can be prepared as in Example 13, but from 105 mg of raw 2-(3-methylbutyl)-3,5-dihydro-4H-imidazol-4-one and 0.2 g of 1H-pyrrolo[2,3-b]pyridine-3-carbaldehyde to give 64 mg of (5Z)-2-(3-methylbutyl)-5-(1H-pyrrolo[2,3-b]pyridin-3-ylmethylidene)-3,5-dihydro-4H-imidazol-4-one in the form of a yellow powder with the following characteristics:
Melting point: 274° C.
$^1$H-NMR spectrum at 400 MHz: 0.93 (d, J=7.5 Hz, 6H); 1.63 (m, 3H); 2.54 (t, J=7.5 Hz, 2H); 7.15 (s, 1H); 7.19 (dd, J=5.0 and 8.0 Hz, 1H); 8.29 (dd, J=1.5 and 5.0 Hz, 1H); 8.33 (s, 1H); 8.91 (d broad, J=8.0 Hz, 1H); 11.05 (s broad, 1H); 12.3 (s broad, 1H).
HPLC-MS-DAD-ELSD: 283(+)=(M+H)(+); 281(−)=(M−H)(−).

b) 2-(3-Methylbutyl)-3,5-dihydro-4H-imidazol-4-one can be prepared as in Example 13, but from 3 g of methyl 4-methyl pentanimidoate hydrochloride to obtain 2.0 g of raw 2-(3-methylbutyl)-3,5-dihydro-4H-imidazol-4-one.

c) Methyl 4-methyl pentanimidoate hydrochloride can be prepared as in Example 13, but from 12.5 cm$^3$ of 3-methylbutyl carbonitrile, 4.6 cm$^3$ of methanol and 5 cm$^3$ of ether. 20.7 g of methyl 4-methyl pentanimidoate hydrochloride is obtained in the form of a white solid.

EXAMPLE 69

(5Z)-2-cyclohexyl-5-(1H-pyrrolo[2,3-b]pyridin-3-ylmethylidene)-3,5-dihydro-4H-imidazol-4-one a) (5Z)-2-cyclohexyl-5-(1H-pyrrolo[2,3-b]pyridin-3-ylmethylidene)-3,5-dihydro-4H-imidazol-4-one can be prepared as in Example 13, but from 296 mg of raw 2-cyclohexyl-3,5-dihydro-4H-imidazol-4-one and 0.13 g of 1H-pyrrolo[2,3-b]pyridine-3-carbaldehyde to give 135 mg of 5Z)-2-cyclohexyl-5-(1H-pyrrolo[2,3-b]pyridin-3-ylmethylidene)-3,5-dihydro-4H-imidazol-4-one in the form of a yellow powder with the following characteristics:
Melting point: 322° C.
$^1$H-NMR spectrum at 400 MHz: from 1.20 to 1.42 (m, 3H); 1.53 (m, 2H); 1.69 (m, 1H); 1.80 (m, 2H); 1.99 (m, 2H); 2.54 (m partially masked, 1H); 7.18 (s, 1H); 7.20 (dd, J=5.0 and 8.0 Hz, 1H); 8.29 (dd, J=1.5 and 5.0 Hz, 1H); 8.34 (s, 1H); 8.93 (d broad, J=8.0 Hz, 1H); 11.1 (m spread out, 1H); 12.3 (m spread out, 1H).
HPLC-MS-DAD-ELSD: 364(+)=(M+H)(+); 362(−)=(M−H)(−).

b) 2-Cyclohexyl-3,5-dihydro-4H-imidazol-4-one can be prepared as in Example 13, but from 704 mg of methyl cyclohexanecarboximidoate hydrochloride to obtain 1.2 g of raw 2-cyclohexyl-3,5-dihydro-4H-imidazol-4-one.

c) Methyl cyclohexanecarboximidoate hydrochloride is prepared according to Synlett 2001, 11, 1707-1710. Gaseous hydrogen chloride is bubbled for 120 min in a solution of 10 cm$^3$ of cyclohexane carbonitrile in 5.4 cm$^3$ of methanol and 30 cm$^3$ of heptane cooled to 0° C. The mixture is stirred for one hour at 0° C. then put in the freezer. After forty-eight hours, the white solid formed is filtered, washed with heptane, then dried under vacuum to obtain 12.0 g of methyl cyclohexanecarboximidoate hydrochloride in the form of a white solid.

EXAMPLE 70

(5Z)-2-cyclohexyl-3-methyl-5-(1H-pyrrolo[2,3-b]pyridin-3-ylmethylidene)-3,5-dihydro-4H-imidazol-4-one a) (5Z)-2-cyclohexyl-3-methyl-5-(1H-pyrrolo[2,3-b]pyridin-3-ylmethylidene)-3,5-dihydro-4H-imidazol-4-one can be prepared as in Example 13, but from 493 mg of raw 2-cyclohexyl-3-methyl-3,5-dihydro-4H-imidazol-4-one and 0.16 g of 1H-pyrrolo[2,3-b]pyridine-3-carbaldehyde to give 144 mg of (5Z)-2-cyclohexyl-3-methyl-5-(1H-pyrrolo[2,3-b]pyridin-3-ylmethylidene)-3,5-dihydro-4H-imidazol-4-one in the form of a yellow powder with the following characteristics:
Melting point: 261-262° C.
$^1$H-NMR spectrum at 400 MHz: from 1.22 to 1.49 (m, 3H); 1.58 (m, 2H); 1.72 (m, 1H); 1.83 (m, 2H); 1.99 (m, 2H); 2.71 (tt, J=3.5 and 11.0 Hz, 1H); 3.13 (s, 3H); 7.21 (dd, J=5.0 and 8.0 Hz, 1H); 7.30 (s, 1H); 8.30 (dd, J=1.5 and 5.0 Hz, 1H); 8.39 (s, 1H); 8.99 (d broad, J=8.0 Hz, 1H); 12.4 (m spread out, 1H).
UPLC-MS-DAD-ELSD: 309(+)=(M+H)(+).

b) 2-cyclohexyl-3-methyl-3,5-dihydro-4H-imidazol-4-one can be prepared as in Example 66, but from 1 g of N-[cyclohexyl(methoxy)methylidene]methylglycinate to obtain 1.07 g of 2-cyclohexyl-3-methyl-3,5-dihydro-4H-imidazol-4-one.

c) N-[cyclohexyl(methoxy)methylidene]methylglycinate can be prepared as in Example 66, but from 1 g of methyl cyclohexanecarboximidoate hydrochloride and 0.71 g of methyl glycinate hydrochloride to obtain 1.09 g of N-[cyclohexyl(methoxy)methylidene]methylglycinate.

EXAMPLE 71

(5Z)-5-(1H-pyrrolo[2,3-b]pyridin-3-ylmethylidene)-2-(tetrahydro-2H-pyran-4-yl)-3,5-dihydro-4H-imidazol-4-one a) (5Z)-5-(1H-pyrrolo[2,3-b]pyridin-3-ylmethylidene)-2-(tetrahydro-2H-pyran-4-yl)-3,5-dihydro-4H-imidazol-4-one can be prepared as in Example 13, but from 690 mg of raw 2-(tetrahydro-2H-pyran-4-yl)-3,5-dihydro-4H-imidazol-4-one and 0.2 g of 1H-pyrrolo[2,3-b]pyridine-3-carbaldehyde to give 283 mg of (5Z)-5-(1H-pyrrolo[2,3-b]pyridin-3-ylmethylidene)-2-(tetrahydro-2H-pyran-4-yl)-3,5-dihydro-4H-imidazol-4-one in the form of a yellow powder with the following characteristics:
Melting point: 317-319° C.
$^1$H-NMR spectrum at 400 MHz: 1.79 (m, 2H); 1.91 (m, 2H); 2.82 (tt, J=3.5 and 11.0 Hz, 1H); 3.45 (m, 2H); 3.94 (m, 2H); 7.20 (m, 2H); 8.29 (dd, J=1.5 and 5.0 Hz, 1H); 8.36 (s, 1H); 8.95 (d broad, J=8.0 Hz, 1H); 11.2 (s broad, 1H); 12.4 (s broad, 1H).
HPLC-MS-DAD-ELSD: 297(+)=(M+H)(+); 295(−)=(M−H)(−).

b) 2-(tetrahydro-2H-pyran-4-yl)-3,5-dihydro-4H-imidazol-4-one can be prepared as in Example 13, but from 2 g of methyl tetrahydro-2H-pyran-4-carboximidoate hydrochloride to obtain 3.2 g of raw 2-(tetrahydro-2H-pyran-4-yl)-3,5-dihydro-4H-imidazol-4-one.

c) Methyl tetrahydro-2H-pyran-4-carboximidoate can be prepared as in Example 13, but from 3 g of tetrahydropyran-4-carbonitrile, 1.2 cm$^3$ of methanol and 6 cm$^3$ of ether. 4.4 g of methyl tetrahydro-2H-pyran-4-carboximidoate hydrochloride is obtained in the form of a white solid.

d) Tetrahydropyran-4-carbonitrile can be prepared as follows:
Slowly add 10 cm$^3$ of thionyl chloride to 3 g of tetrahydropyran-4-carboxamide cooled on an ice bath. Heat the mixture at 80° C. for two hours, then concentrate under vacuum. Take up the residue in 20 cm$^3$ of water and adjust the pH of the solution to pH 7 with potassium hydroxide. Extract the aqueous phase with ethyl acetate (4×50 cm$^3$). The combined organic phases are washed with water (2×50 cm$^3$), dried over magnesium sulphate, and then concentrated under vacuum to obtain 2.47 g of tetrahydropyran-4-carbonitrile.

e) Tetrahydropyran-4-carboxamide is prepared according to J. Chem. Soc. 1930, 2525-2530.

EXAMPLE 72

(5Z)-5-[(1H-pyrrolo[2,3-b]pyridin-3-yl)methylidene]-3-methyl-2-(tetrahydro-2H-pyran-4-yl)-3,5-dihydro-4H-imidazol-4-one a) (5Z)-5-[(1H-pyrrolo[2,3-b]pyridin-3-yl)methylidene]-3-methyl-2-(tetrahydro-2H-pyran-4-yl)-3,5-dihydro-4H-imidazol-4-one can be prepared as in Example 13, but from 748 mg of raw 2-(tetrahydro-2H-pyran-4-yl)-3-methyl-imidazolidin-4-one and 0.2 g of 1H-pyrrolo[2,3-b]pyridine-3-carbaldehyde, to give 193 mg of (5Z)-5-[(1H-pyrrolo[2,3-b]pyridin-3-yl)methylidene]-3-methyl-2-(tetrahydro-2H-pyran-4-yl)-3,5-dihydro-4H-imidazol-4-one in the form of a yellow powder with the following characteristics:
Melting point: 283-285° C.
$^1$H-NMR spectrum at 400 MHz: from 1.53 to 1.93 (m, 4H); 3.03 (m, 1H); 3.16 (s, 3H); 3.51 (m, 2H); 3.99 (m, 2H); 7.21 (dd, J=5.0 and 8.0 Hz, 1H); 7.32 (s, 1H); 8.29 (dd, J=1.5 and 5.0 Hz, 1H); 8.39 (s, 1H); 9.01 (d broad, J=8.0 Hz, 1H); 12, 3 (m spread out, 1H).
HPLC-MS-DAD-ELSD: 311(+)=(M+H)(+); 309(−)=(M−H)(−).

b) 2-(tetrahydro-2H-pyran-4-yl)-3-methyl-imidazolidin-4-one can be prepared as in Example 66, but from 2.55 g of N-[methoxy(tetrahydro-2H-pyran-4-yl)methylidene]methylglycinate, to obtain 2.03 g of 2-(tetrahydro-2H-pyran-4-yl)-3-methyl-imidazolidin-4-one.

c) N-[methoxy(tetrahydro-2H-pyran-4-yl)methylidene]methylglycinate can be prepared as in Example 66, but from 2 g of methyl tetrahydro-2H-pyran-4-carboximidoate hydrochloride and 1.41 g of methyl glycinate hydrochloride, to obtain 2.55 g of N-[methoxy(tetrahydro-2H-pyran-4-yl)methylidene]methylglycinate.

EXAMPLE 73

(5Z)-5-[(5-chloro-1H-pyrrolo[2,3-b]pyridin-3-yl)methylidene]-3-methyl-2-(tetrahydro-2H-pyran-4-yl)-3,5-dihydro-4H-imidazol-4-one (5Z)-5-[(5-chloro-1H-pyrrolo[2,3-b]pyridin-3-yl)methylidene]-3-methyl-2-(tetrahydro-2H-pyran-4-yl)-3,5-dihydro-4H-imidazol-4-one can be prepared as in Example 13, but from 303 mg of raw 2-(tetrahydro-2H-pyran-4-yl)-3-methyl-imidazolidin-4-one (Example 72) and 0.1 g of 5-chloro-1H-pyrrolo[2,3-b]pyridine-3-carbaldehyde to give 130 mg of (5Z)-5-[(5-chloro-1H-pyrrolo[2,3-b]pyridin-3-yl)methylidene]-3-methyl-2-(tetrahydro-2H-pyran-4-yl)-3,5-dihydro-4H-imidazol-4-one in the form of a yellow powder with the following characteristics:
Melting point: 338° C.
$^1$H-NMR spectrum at 400 MHz: from 1.75 to 1.97 (m, 4H); 3.06 (m, 1H); 3.17 (s, 3H); 3.52 (m, 2H); 3.99 (m, 2H); 7.31 (s, 1H); 8.29 (d, J=2.0 Hz, 1H); 8.39 (s, 1H); 9.48 (s broad, 1H); 12.65 (m spread out, 1H).
HPLC-MS-DAD-ELSD: 345(+)/ . . . =(M+H)(+)/ . . . ; 343(−)/ . . . =(M−H)(−)/ . . . (1 chlorine atom Cl present).

EXAMPLE 74

(5Z)-2-(2-methylpropyl)-5-(1H-pyrrolo[2,3-b]pyridin-3-ylmethylidene)-3,5-dihydro-4H-imidazol-4-one a) (5Z)-2-(2-methylpropyl)-5-(1H-pyrrolo[2,3-b]pyridin-3-ylmethylidene)-3,5-dihydro-4H-imidazol-4-one can be prepared as in Example 13, but from 575 mg of raw 2-(2-methylpropyl)-3,5-dihydro-4H-imidazol-4-one and 0.2 g of 1H-pyrrolo[2,3-b]pyridine-3-carbaldehyde to give 99 mg of (5Z)-2-(2-methylpropyl)-5-(1H-pyrrolo[2,3-b]pyridin-3-ylmethylidene)-3,5-dihydro-4H-imidazol-4-one in the form of a yellow powder with the following characteristics:
Melting point: 292-293° C.
$^1$H-NMR spectrum at 400 MHz: 1.00 (d, J=7.0 Hz, 6H); 2.18 (m, 1H); 2.41 (d, J=7.0 Hz, 2H); 7.17 (s, 1H); 7.19 (dd, J=5.0 and 8.0 Hz, 1H); 8.29 (dd, J=1.5 and 5.0 Hz, 1H); 8.34 (s, 1H); 8.89 (d broad, J=8.0 Hz, 1H); 11.1 (s broad, 1H); 12.35 (m spread out, 1H).
HPLC-MS-DAD-ELSD: 269(+)=(M+H)(+); 267(−)=(M−H)(−).

b) 2-(2-methylpropyl)-3,5-dihydro-4H-imidazol-4-one can be prepared as in Example 13, but from 2 g of methyl 3-methylbutanimidoate hydrochloride to obtain 1.5 g of raw 2-(2-methylpropyl)-3,5-dihydro-4H-imidazol-4-one.

c) Methyl 3-methylbutanimidoate hydrochloride can be prepared as in Example 13, but from 3.1 cm$^3$ of 2-methylpropyl carbonitrile, 1.3 cm$^3$ of methanol and 4 cm$^3$ of ether. 4.0 g of methyl 3-methylbutanimidoate hydrochloride is obtained in the form of a white solid.

EXAMPLE 75

(5Z)-3-methyl-2-(2-methylpropyl)-5-(1H-pyrrolo[2,3-b]pyridin-3-ylmethylidene)-3,5-dihydro-4H-imidazol-4-one a) (5Z)-3-methyl-2-(2-methylpropyl)-5-(1H-pyrrolo[2,3-b]pyridin-3-ylmethylidene)-3,5-dihydro-4H-imidazol-4-one can be prepared as in Example 13, but from 466 mg of raw 3-methyl-2-(2-methylpropyl)-3,5-dihydro-4H-imidazol-4-one and 0.17 g of 1H-pyrrolo[2,3-b]pyridine-3-carbaldehyde, to give 82 mg of (5Z)-3-methyl-2-(2-methylpropyl)-5-(1H-pyrrolo[2,3-b]pyridin-3-ylmethylidene)-3,5-dihydro-4H-imidazol-4-one in the form of a yellow powder with the following characteristics:
Melting point: 201° C.
$^1$H-NMR spectrum at 400 MHz: 1.07 (d, J=7.5 Hz, 6H); 2.27 (m, 1H); 2.56 (d, J=7.5 Hz, 2H); 3.10 (s, 3H); 7.19 (dd, J=5.0 and 8.0 Hz, 1H); 7.29 (s, 1H); 8.29 (dd, J=1.5 and 5.0 Hz, 1H); 8.38 (s, 1H); 8.98 (d broad, J=8.0 Hz, 1H); 12.4 (m spread out, 1H).
UPLC-MS-DAD-ELSD: 283(+)=(M+H)(+); 281(−)=(M−H)(−).

b) 3-methyl-2-(2-methylpropyl)-3,5-dihydro-4H-imidazol-4-one can be prepared as in Example 66, but from 1.16 g of N-(1-methoxy-3-methylbutylidene)methylglycinate, to obtain 901 mg of 3-methyl-2-(2-methylpropyl)-3,5-dihydro-4H-imidazol-4-one.

c) N-(1-methoxy-3-methylbutylidene)methylglycinate can be prepared as in Example 66, but from 959 mg of methyl 3-methylbutanimidoate hydrochloride and 802 mg of methyl glycinate hydrochloride to obtain 1.18 g of N-(1-methoxy-3-methylbutylidene)methylglycinate.

EXAMPLE 76

(5Z)-5-[(5-chloro-1H-pyrrolo[2,3-b]pyridin-3-yl)methylidene]-3-methyl-2-(2-methylpropyl)-3,5-dihydro-4H-imidazol-4-one (5Z)-5-[(5-chloro-1H-pyrrolo[2,3-b]pyridin-3-yl)methylidene]-3-methyl-2-(2-methylpropyl)-3,5-dihydro-4H-imidazol-4-one can be prepared as in Example 13, but from 420 mg of raw 3-methyl-2-(2-methylpropyl)-3,5-dihydro-4H-imidazol-4-one (Example 75) and 0.2 g of 5-chloro-1H-pyrrolo[2,3-b]pyridine-3-carbaldehyde to give 220 mg of (5Z)-5-[(5-chloro-1H-pyrrolo[2,3-b]pyridin-3-yl)methylidene]-3-methyl-2-(2-methylpropyl)-3,5-dihydro-4H-imidazol-4-one in the form of a yellow powder with the following characteristics:
Melting point: 282° C.
$^1$H-NMR spectrum at 400 MHz: 1.11 (d, J=7.5 Hz, 6H); 2.33 (m, 1H); 2.59 (d, J=7.0 Hz, 2H); 3.10 (s, 3H); 7.29 (s, 1H); 8.30 (d, J=2.0 Hz, 1H); 8.38 (s, 1H); 9.46 (d broad, J=2.0 Hz, 1H); 12.6 (m spread out, 1H).
HPLC-MS-DAD-ELSD: 317(+)/ . . . =(M+H)(+)/ . . . ; 315(−)/ . . . =(M−H)(−)/ . . . (1 chlorine atom Cl present).

EXAMPLE 77

(5Z)-2-(cyclopropylmethyl)-5-(1H-pyrrolo[2,3-b]pyridin-3-ylmethylidene)-3,5-dihydro-4H-imidazol-4-one a) (5Z)-2-(cyclopropylmethyl)-5-(1H-pyrrolo[2,3-b]pyridin-3-ylmethylidene)-3,5-dihydro-4H-imidazol-4-one can be prepared as in Example 13, but from 354 mg of raw 2-(cyclopropylmethyl)-3,5-dihydro-4H-imidazol-4-one and 0.2 g of 1H-pyrrolo[2,3-b]pyridine-3-carbaldehyde to give 142 mg of (5Z)-2-(cyclopropylmethyl)-5-(1H-pyrrolo[2,3-b]pyridin-3-ylmethylidene)-3,5-dihydro-4H-imidazol-4-one in the form of a yellow powder with the following characteristics:
Melting point: 289° C.
$^1$H-NMR spectrum at 400 MHz: 0.29 (m, 2H); 0.55 (m, 2H); 1.14 (m, 1H); 2.45 (d, J=7.5 Hz, 2H); 7.19 (m, 2H); 8.29 (dd; J=1.5 and 5.5 Hz, 1H); 8.34 (s, 1H); 8.98 (dd, J=1.5 and 8.0 Hz, 1H); 11.1 (s broad, 1H); 12.35 (m spread out, 1H).
HPLC-MS-DAD-ELSD: 267(+)=(M+H)(+); 265(−)=(M−H)(−).

b) 2-(cyclopropylmethyl)-3,5-dihydro-4H-imidazol-4-one can be prepared as in Example 13, but from 2 g of methyl 2-cyclopropylethanimidoate hydrochloride to obtain 2.5 g of raw 2-(cyclopropylmethyl)-3,5-dihydro-4H-imidazol-4-one.

c) Methyl 2-cyclopropylethanimidoate hydrochloride can be prepared as in Example 13, but from 10 cm$^3$ of cyclopropylmethyl carbonitrile, 4.7 cm$^3$ of methanol and 10 cm$^3$ of ether. 18.2 g of methyl 2-cyclopropylethanimidoate hydrochloride is obtained in the form of a white solid.

EXAMPLE 78

(5Z)-2-(cyclopropylmethyl)-5-(5-chloro-1H-pyrrolo[2,3-b]pyridin-3-ylmethylidene)-3,5-dihydro-4H-imidazol-4-one (5Z)-2-(cyclopropylmethyl)-5-(5-chloro-1H-pyrrolo[2,3-b]pyridin-3-ylmethylidene)-3,5-dihydro-4H-imidazol-4-one can be prepared as in Example 13, but from 144 mg of raw 2-(cyclopropylmethyl)-3,5-dihydro-4H-imidazol-4-one (Example 77) and 0.1 g of 5-chloro-1H-pyrrolo[2,3-b]pyridine-3-carbaldehyde to give 47 mg of (5Z)-2-(cyclopropylmethyl)-5-(5-chloro-1H-pyrrolo[2,3-b]pyridin-3-ylmethylidene)-3,5-dihydro-4H-imidazol-4-one in the form of a yellow powder with the following characteristics:
Melting point: 295-296° C.
$^1$H-NMR spectrum at 400 MHz: 0.30 (m, 2H); 0.60 (m, 2H); 1.17 (m, 1H); 2.48 (m partially masked, 2H); 7.17 (s, 1H); 8.29 (d, J=2.0 Hz, 1H); 8.35 (s, 1H); 9.42 (s broad, 1H); 11.15 (s broad, 1H); 12.5 (m spread out, 1H).
HPLC-MS-DAD-ELSD: 301(+)/ . . . =(M+H)(+)/ . . . ; 299(−)/ . . . =(M−H)(−)/ . . . (1 chlorine atom Cl present).

EXAMPLE 79

(5Z)-2-(1-methylethyl)-5-(1H-pyrrolo[2,3-b]pyridin-3-ylmethylidene)-3,5-dihydro-4H-imidazol-4-one a) (5Z)-2-(1-methylethyl)-5-(1H-pyrrolo[2,3-b]pyridin-3-ylmethylidene)-3,5-dihydro-4H-imidazol-4-one can be prepared as in Example 13, but from 324 mg of raw 2-(1-methylethyl)-3,5-dihydro-4H-imidazol-4-one and 0.2 g of 1H-pyrrolo[2,3-b]pyridine-3-carbaldehyde, to give 140 mg of (5Z)-2-(1-methylethyl)-5-(1H-pyrrolo[2,3-b]pyridin-3-ylmethylidene)-3,5-dihydro-4H-imidazol-4-one in the form of a yellow powder with the following characteristics:
Melting point: 309-310° C.
$^1$H-NMR spectrum at 400 MHz: 1.29 (d, J=7.0 Hz, 6H); 2.81 (m, 1H); 7.18 (s, 1H); 7.20 (dd, J=5.0 and 8.0 Hz, 1H); 8.29 (dd, J=1.5 and 5.0 Hz, 1H); 8.34 (s, 1H); 8.98 (d broad, J=8.0 Hz, 1H); 11.15 (m spread out, 1H); 12.35 (m spread out, 1H).
HPLC-MS-DAD-ELSD: 255(+)=(M+H)(+); 253(−)=(M−H)(−).

b) 2-(1-methylethyl)-3,5-dihydro-4H-imidazol-4-one can be prepared as in Example 13, but from 2 g of methyl 2-methylpropanimidoate hydrochloride to obtain 1.5 g of raw 2-(1-methylethyl)-3,5-dihydro-4H-imidazol-4-one.

c) Methyl 2-methylpropanimidoate hydrochloride can be prepared as in Example 13, but from 10 cm$^3$ of isopropyl carbonitrile, 5 cm$^3$ of methanol and 10 cm$^3$ of ether. 17 g of methyl 2-methylpropanimidoate hydrochloride is obtained in the form of a white solid.

EXAMPLE 80

(5Z)-2-(1-methylethyl)-5-(5-chloro-1H-pyrrolo[2,3-b]pyridin-3-ylmethylidene)-3,5-dihydro-4H-imidazol-4-one (5Z)-2-(1-methylethyl)-5-(5-chloro-1H-pyrrolo[2,3-b]pyridin-3-ylmethylidene)-3,5-dihydro-4H-imidazol-4-one can be prepared as in Example 13, but from 131 mg of raw 2-(1-methylethyl)-3,5-dihydro-4H-imidazol-4-one (Example 79) and 0.1 g of 5-chloro-1H-pyrrolo[2,3-b]pyridine-3-carbaldehyde to give 116 mg of (5Z)-2-(1-methylethyl)-5-(5-chloro-1H-pyrrolo[2,3-b]pyridin-3-ylmethylidene)-3,5-dihydro-4H-imidazol-4-one in the form of a yellow powder with the following characteristics:
Melting point: 277-280° C.
$^1$H-NMR spectrum at 400 MHz: 1.30 (d, J=7.5 Hz, 6H); 2.81 (m, 1H); 7.15 (s, 1H); 8.29 (d, J=2.0 Hz, 1H); 8.32 (s, 1H); 9.47 (d broad, J=2.0 Hz, 1H); 11.15 (s broad, 1H); 12.55 (m spread out, 1H).
HPLC-MS-DAD-ELSD: 289(+)/ . . . =(M+H)(+)/ . . . ; 287(−)/ . . . =(M−H)(−)/ . . . (1 chlorine atom Cl present).

EXAMPLE 81

(5Z)-3-methyl-2-(1-methylethyl)-5-(1H-pyrrolo[2,3-b]pyridin-3-ylmethylidene)-3,5-dihydro-4H-imidazol-4-one a) (5Z)-3-methyl-2-(1-methylethyl)-5-(1H-pyrrolo[2,3-b]pyridin-3-ylmethylidene)-3,5-dihydro-4H-imidazol-4-one can be prepared as in Example 13, but from 437 mg of raw 3-methyl-2-(1-methylethyl)-3,5-dihydro-4H-imidazol-4-one and 0.19 g of 1H-pyrrolo[2,3-b]pyridine-3-carbaldehyde to give 163 mg of (5Z)-3-methyl-2-(1-methylethyl)-5-(1H-pyrrolo[2,3-b]pyridin-3-ylmethylidene)-3,5-dihydro-4H-imidazol-4-one in the form of a yellow powder with the following characteristics:
Melting point: 222-224° C.
$^1$H-NMR spectrum at 400 MHz: 1.31 (d, J=7.0 Hz, 6H); 3.02 (m, 1H); 3.15 (s, 3H); 7.20 (dd, J=5.0 and 8.0 Hz, 1H); 7.31 (s, 1H); 8.29 (dd, J=1.5 and 5.0 Hz, 1H); 8.39 (s, 1H); 9.05 (d broad, J=8.0 Hz, 1H); 12.4 (m spread out, 1H).
HPLC-MS-DAD-ELSD: 269(+)=(M+H)(+); 267(−)=(M−H)(−).

b) 3-methyl-2-(1-methylethyl)-3,5-dihydro-4H-imidazol-4-one can be prepared as in Example 66, but from 1 g of N-(1-methoxy-2-methylpropylidene)methylglycinate, to obtain 789 mg of 3-methyl-2-(1-methylethyl)-3,5-dihydro-4H-imidazol-4-one.

c) N-(1-methoxy-2-methylpropylidene)methylglycinate can be prepared as in Example 66, but from 870 mg of methyl 2-methylpropanimidoate hydrochloride and 802 mg of methyl glycinate hydrochloride to obtain 1 g of N-(1-methoxy-2-methylpropylidene)methylglycinate.

EXAMPLE 82

(5Z)-5-[(5-chloro-1H-pyrrolo[2,3-b]pyridin-3-yl)methylidene]-3-methyl-2-(1-methylethyl)-3,5-dihydro-4H-imidazol-4-one (5Z)-5-[(5-chloro-1H-pyrrolo[2,3-b]pyridin-3-yl)methylidene]-3-methyl-2-(1-methylethyl)-3,5-dihydro-4H-imidazol-4-one can be prepared as in Example 13, but from 350 mg of raw 3-methyl-2-(1-methylethyl)-3,5-dihydro-4H-imidazol-4-one (Example 81) and 0.2 g of 5-chloro-1H-pyrrolo[2,3-b]pyridine-3-carbaldehyde, to give 235 mg of (5Z)-5-[(5-chloro-1H-pyrrolo[2,3-b]pyridin-3-yl)methylidene]-3-methyl-2-(1-methylethyl)-3,5-dihydro-4H-imidazol-4-one in the form of a yellow powder with the following characteristics:
Melting point: 282° C.
$^1$H-NMR spectrum at 400 MHz: 1.32 (d, J=7.5 Hz, 6H); 3.04 (m, 1H); 3.15 (s, 3H); 7.29 (s, 1H); 8.30 (d, J=2.0 Hz, 1H); 8.37 (s, 1H); 9.55 (s broad, 1H); 12.6 (m spread out, 1H).
HPLC-MS-DAD-ELSD: 303(+)/ . . . =(M+H)(+)/ . . . ; 301(−)/ . . . =(M−H)(−)/ . . . (1 Cl present).

EXAMPLE 83

(5Z)-2,3-dimethyl-5-(1H-pyrrolo[2,3-b]pyridin-3-ylmethylidene)-3,5-dihydro-4H-imidazol-4-one a) (5Z)-2,3-dimethyl-5-(1H-pyrrolo[2,3-b]pyridin-3-ylmethylidene)-3,5-dihydro-4H-imidazol-4-one can be prepared as follows:
In a microwave oven reactor, mix together 0.8 cm$^3$ of an 8M solution of methylamine in ethanol and a suspension of 200 mg of (4Z)-4-[(1-acetyl-1H-pyrrolo[2,3-b]pyridin-3-yl)methylidene]-2-methyl-1,3-oxazol-5(4H)-one in 4 cm$^3$ of ethanol. Seal the reactor, then irradiate with microwave radiation for thirteen minutes at 170° C. After filtration of the solid matter, 127 mg of (5Z)-2,3-dimethyl-5-(1H-pyrrolo[2,3-b]pyridin-3-ylmethylidene)-3,5-dihydro-4H-imidazol-4-one is obtained in the form of orange powder with the following characteristics:
$^1$H-NMR spectrum at 400 MHz: 2.37 (s, 3H); 3.10 (s, 3H); 7.20 (dd, J=5.0 and 8.0 Hz, 1H); 7.29 (s, 1H); 8.29 (dd, J=1.5 and 5.0 Hz, 1H); 8.39 (s, 1H); 8.91 (d broad, J=8.0 Hz, 1H); 12.35 (m spread out, 1H).
HPLC-MS-DAD-ELSD: 241(+)=(M+H)(+); 239(−)=(M−H)(−).

b) (4Z)-4-[(1-acetyl-1H-pyrrolo[2,3-b]pyridin-3-yl)methylidene]-2-methyl-1,3-oxazol-5(4H)-one can be prepared as follows:
Put 1.92 g of N-acetylglycine and 1.23 g of sodium acetate in 25 cm$^3$ of acetic anhydride in a three-necked flask, under argon. Heat the reaction mixture to 80° C., stirring for one hour. Add 2 g of 1H-pyrrolo[2,3-b]pyridine-3-carbaldehyde and, after two hours at 140° C., cool the reaction mixture to 25° C., then filter. Rinse the solid with water and then with ethanol before evaporating to dryness at reduced pressure. 1.68 g of (4Z)-2-methyl-4-(1H-pyrrolo[2,3-b]pyridin-3-ylmethylidene)-1,3-oxazol-5(4H)-one is obtained in the form of a yellow powder with the following characteristics:

LC/MS (1): Retention time: 3.3 min; 270(+)=[MH$^+$].

EXAMPLE 84

(5Z)-2-methyl-5-(1H-pyrrolo[2,3-b]pyridin-3-ylmethylidene)-3,5-dihydro-4H-imidazol-4-one (5Z)-2-methyl-5-(1H-pyrrolo[2,3-b]pyridin-3-ylmethylidene)-3,5-dihydro-4H-imidazol-4-one can be prepared as in Example 83, but from 2.2 cm$^3$ of 40% ammonia in ethanol and 200 mg of (4Z)-4-[(1-acetyl-1H-pyrrolo[2,3-b]pyridin-3-yl)methylidene]-2-methyl-1,3-oxazol-5(4H)-one in 2 cm$^3$ of ethanol. After eighteen minutes at 170° C. under microwave irradiation and filtration of the solid, 108 mg of (5Z)-2-methyl-5-(1H-pyrrolo[2,3-b]pyridin-3-ylmethylidene)-3,5-dihydro-4H-imidazol-4-one is obtained in the form of orange powder with the following characteristics:

Melting point: 277-281° C.

$^1$H-NMR spectrum at 400 MHz: 2.25 (s, 3H); 7.15 (s, 1H); 7.19 (dd, J=5.0 and 8.0 Hz, 1H); 8.29 (d broad, J=5.0 Hz, 1H); 8.35 (s, 1H); 8.87 (d broad, J=8.0 Hz, 1H); 11.1 (m spread out, 1H); 12.35 (m spread out, 1H).

UPLC-MS-DAD-ELSD: 225(+)=(M+H)(+); 227(−)=(M−H)(−).

EXAMPLE 85

(5Z)-2-methyl-3-(2-morpholin-4-ylethyl)-5-(1H-pyrrolo[2,3-b]pyridin-3-ylmethylidene)-3,5-dihydro-4H-imidazol-4-one (5Z)-2-methyl-3-(2-morpholin-4-ylethyl)-5-(1H-pyrrolo[2,3-b]pyridin-3-ylmethylidene)-3,5-dihydro-4H-imidazol-4-one can be prepared as in Example 83, but from 0.98 cm$^3$ of 2-morpholin-4-ylethanamine and 200 mg of (4Z)-4-[(1-acetyl-1H-pyrrolo[2,3-b]pyridin-3-yl)methylidene]-2-methyl-1,3-oxazol-5(4H)-one in 2 cm$^3$ of ethanol. After eighteen minutes at 170° C. under microwave irradiation and filtration of the solid, 105 mg of (5Z)-2-methyl-3-(2-morpholin-4-ylethyl)-5-(1H-pyrrolo[2,3-b]pyridin-3-ylmethylidene)-3,5-dihydro-4H-imidazol-4-one is obtained in the form of orange powder with the following characteristics:

Melting point: 235-240° C.

$^1$H-NMR spectrum at 400 MHz: from 2.30 to 2.55 (m partially masked, 9H); 3.55 (m, 4H); 3.69 (t, J=6.0 Hz, 2H); 7.21 (dd, J=5.0 and 8.0 Hz, 1H); 7.29 (s, 1H); 8.30 (dd, J=1.5 and 5.0 Hz, 1H); 8.39 (s, 1H); 8.92 (d broad, J=8.0 Hz, 1H); 10.0 (m very broad, 1H).

EXAMPLE 86

(5Z)-3-benzyl-2-methyl-5-(1H-pyrrolo[2,3-b]pyridin-3-ylmethylidene)-3,5-dihydro-4H-imidazol-4-one (5Z)-3-benzyl-2-methyl-5-(1H-pyrrolo[2,3-b]pyridin-3-ylmethylidene)-3,5-dihydro-4H-imidazol-4-one can be prepared as in Example 83, but from 0.8 cm$^3$ of 1-phenylmethanamine and 200 mg of (4Z)-4-[(1-acetyl-1H-pyrrolo[2,3-b]pyridin-3-yl)methylidene]-2-methyl-1,3-oxazol-5(4H)-one in 2 cm$^3$ of ethanol. After fifteen minutes at 170° C. under microwave irradiation and filtration of the solid, 105 mg of (5Z)-3-benzyl-2-methyl-5-(1H-pyrrolo[2,3-b]pyridin-3-ylmethylidene)-3,5-dihydro-4H-imidazol-4-one is obtained in the form of a yellow powder with the following characteristics:

Melting point: 274-275° C.

$^1$H-NMR spectrum at 400 MHz: 2.28 (s, 3H); 4.83 (s, 2H); 7.20 (dd, J=5.0 and 8.0 Hz, 1H); 7.24 (d, J=7.5 Hz, 2H); 7.30 (t, J=7.5 Hz, 1H); 7.38 (m, 3H); 8.29 (dd, J=1.5 and 5.0 Hz, 1H); 8.41 (s, 1H); 8.92 (d broad, J=8.0 Hz, 1H); 12.45 (m spread out, 1H).

EXAMPLE 87

(5Z)-2-methyl-3-propyl-5-(1H-pyrrolo[2,3-b]pyridin-3-ylmethylidene)-3,5-dihydro-4H-imidazol-4-one (5Z)-2-methyl-3-propyl-5-(1H-pyrrolo[2,3-b]pyridin-3-ylmethylidene)-3,5-dihydro-4H-imidazol-4-one can be prepared as in Example 83, but from 0.6 cm$^3$ of propan-1-amine and 200 mg of (4Z)-4-[(1-acetyl-1H-pyrrolo[2,3-b]pyridin-3-yl)methylidene]-2-methyl-1,3-oxazol-5(4H)-one in 2 cm$^3$ of ethanol. After sixteen minutes at 170° C. under microwave irradiation and filtration of the solid, 73 mg of (5Z)-2-methyl-3-propyl-5-(1H-pyrrolo[2,3-b]pyridin-3-ylmethylidene)-3,5-dihydro-4H-imidazol-4-one is obtained in the form of yellow crystals with the following characteristics:

Melting point: 206° C.

$^1$H-NMR spectrum at 400 MHz: 0.88 (t, J=7.5 Hz, 3H); 1.58 (m, 2H); 2.38 (s, 3H); 3.53 (t, J=7.5 Hz, 2H); 7.19 (m, 1H); 7.28 (s, 1H); 8.29 (m, 1H); 8.39 (s, 1H); 8.90 (d broad, J=8.0 Hz, 1H); 12.35 (m spread out, 1H).

HPLC-MS-DAD-ELSD: 269(+)=(M+H)(+); 267(−)=(M−H)(−).

EXAMPLE 88

(5Z)-2-methyl-3-(1-methylethyl)-5-(1H-pyrrolo[2,3-b]pyridin-3-ylmethylidene)-3,5-dihydro-4H-imidazol-4-one (5Z)-2-methyl-3-(1-methylethyl)-5-(1H-pyrrolo[2,3-b]pyridin-3-ylmethylidene)-3,5-dihydro-4H-imidazol-4-one can be prepared as in Example 83, but from 0.63 cm$^3$ of propan-2-amine and 200 mg of (4Z)-4-[(1-acetyl-1H-pyrrolo[2,3-b]pyridin-3-yl)methylidene]-2-methyl-1,3-oxazol-5(4H)-one in 2 cm$^3$ of ethanol. After thirty-eight minutes at 170° C. under microwave irradiation and filtration of the solid, the filtrate is purified by preparative LC-MS [Column Xterra RP18 30×100; 5µ; with water buffered with 10 mM of ammonium hydrogen carbonate adjusted to pH 9 with ammonia/acetonitrile with gradient from 70/30 to 0/100 in 8 min]. 39 mg of (5Z)-2-methyl-3-(1-methylethyl)-5-(1H-pyrrolo[2,3-b]pyridin-3-ylmethylidene)-3,5-dihydro-4H-imidazol-4-one is obtained in the form of yellow lyophilizate with the following characteristics:

Melting point: 207° C.

$^1$H-NMR spectrum at 400 MHz: 1.41 (d, J=7.0 Hz, 6H); 2.40 (s, 3H); 4.21 (m, 1H); 7.21 (m, 2H); 8.29 (dd, J=1.5 and 5.0 Hz, 1H); 8.37 (s, 1H); 8.90 (dd, J=1.5 and 8.0 Hz, 1H).

EXAMPLE 89

(5Z)-2-butyl-5-[(5-chloro-1H-pyrrolo[2,3-b]pyridin-3-yl)methylidene]-3-methyl-3,5-dihydro-4H-imidazol-4-one a) (5Z)-2-butyl-5-[(5-chloro-1H-pyrrolo[2,3-b]pyridin-3-yl)methylidene]-3-methyl-3,5-dihydro-4H-imidazol-4-one can be prepared as in Example 83, but from 0.14 cm$^3$ of 33% methylamine in ethanol and 67 mg of (4Z)-4-[(1-acetyl-5-chloro-1H-pyrrolo[2,3-b]pyridin-3-yl)methylidene]-2-butyl-1,3-oxazol-5(4H)-one in 4 cm$^3$ of ethanol. After fifteen minutes at 170° C. under microwave irradiation and filtration of the solid, 26 mg of (5Z)-2-butyl-5-[(5-chloro-1H-pyrrolo[2,3-b]pyridin-3-yl)methylidene]-3-methyl-3,5-dihydro-4H-imidazol-4-one is obtained in the form of a yellow powder with the following characteristics:
Melting point: 295-300° C.
$^1$H-NMR spectrum at 400 MHz: 1.00 (t, J=7.5 Hz, 3H); 1.50 (m, 2H); 1.85 (m, 2H); 2.69 (t, J=7.5 Hz, 2H); 3.10 (s, 3H); 7.27 (s, 1H); 8.29 (s broad, 1H); 8.35 (s, 1H); 9.50 (s broad, 1H); 12.55 (m spread out, 1H).
UPLC-MS-DAD-ELSD: 317(+)/ . . . =(M+H)(+)/ . . . ; 315(−)/ . . . =(M−H)(−)/ . . . (1 chlorine atom Cl present).

b) (4Z)-4-[(1-acetyl-5-chloro-1H-pyrrolo[2,3-b]pyridin-3-yl)methylidene]-2-butyl-1,3-oxazol-5(4H)-one can be prepared as in Example 83, but from 0.32 g of N-pentanoylglycine, 0.25 g of potassium acetate and 0.3 g of 5-chloro-1H-pyrrolo[2,3-b]pyridine-3-carbaldehyde in 1 cm$^3$ of acetic anhydride. After four hours at 90° C., cool the reaction mixture to 25° C. and then dilute with water. The solid formed is filtered and purified by chromatography on silica (elution with methylene chloride) to obtain 69 mg of (4Z)-4-[(1-acetyl-5-chloro-1H-pyrrolo[2,3-b]pyridin-3-yl)methylidene]-2-butyl-1,3-oxazol-5(4H)-one in the form of a yellow powder with the following characteristics:
LC/MS retention time 5.75 min; LC-MS-DAD-ELSD: 346 (+)=(M+H)(+).
During the preceding purification, 88 mg of (4Z)-4-[(1-acetyl-5-chloro-1H-pyrrolo[2,3-b]pyridin-3-yl)methylidene]-2-methyl-1,3-oxazol-5(4H)-one is also isolated.

EXAMPLE 90

(5Z)-5-[(5-chloro-1H-pyrrolo[2,3-b]pyridin-3-yl)methylidene]-2,3-dimethyl-3,5-dihydro-4H-imidazol-4-one (5Z)-5-[(5-chloro-1H-pyrrolo[2,3-b]pyridin-3-yl)methylidene]-2,3-dimethyl-3,5-dihydro-4H-imidazol-4-one can be prepared as in Example 83, but from 0.21 cm$^3$ of 33% methylamine in ethanol and 85 mg of (4Z)-4-[(1-acetyl-5-chloro-1H-pyrrolo[2,3-b]pyridin-3-yl)methylidene]-2-methyl-1,3-oxazol-5(4H)-one (see Example 89) in 4 cm$^3$ of ethanol. After fifteen minutes at 170° C. under microwave irradiation and filtration of the solid, 41 mg of (5Z)-2-methyl-5-[(5-chloro-1H-pyrrolo[2,3-b]pyridin-3-yl)methylidene]-3-methyl-3,5-dihydro-4H-imidazol-4-one is obtained in the form of a yellow powder with the following characteristics:
Melting point: 295-300° C.
$^1$H-NMR spectrum at 400 MHz: 2.37 (s, 3H); 3.11 (s, 3H); 7.29 (s, 1H); 8.30 (d, J=2.0 Hz, 1H); 8.41 (s, 1H); 9.20 (s broad, 1H); 12.6 (m spread out, 1H).
UPLC-MS-DAD-ELSD: 275(+)/ . . . =(M+H)(+)/ . . . ; 274(−)/ . . . =(M−H)(−)/ . . . (1 chlorine atom Cl present).

EXAMPLE 91

(5Z)-2-[methyl(2-methylpropyl)amino]-5-[(5-methyl-1H-pyrrolo[2,3-b]pyridin-3-yl)methylidene]-3,5-dihydro-4H-imidazol-4-one (5Z)-2-[methyl(2-methylpropyl)amino]-5-[(5-methyl-1H-pyrrolo[2,3-b]pyridin-3-yl)methylidene]-3,5-dihydro-4H-imidazol-4-one can be prepared as in Example 7, but from 240 mg of (5Z)-5-[(5-methyl-1H-pyrrolo[2,3-b]pyridin-3-yl)methylidene]-2-thioxoimidazolidin-4-one (Example 17), 4 cm$^3$ of ethanol and 680 mg of methyl-(2-methyl)propylamine. After twenty minutes at a temperature of 160° C. and one hour at 180° C. under microwave irradiation, then filtration of the solid, 55 mg of (5Z)-2-[methyl(2-methylpropyl)amino]-5-[(5-methyl-1H-pyrrolo[2,3-b]pyridin-3-yl)methylidene]-3,5-dihydro-4H-imidazol-4-one is obtained in the form of a brown powder with the following characteristics:
Melting point: 287-289° C.
$^1$H-NMR spectrum at 400 MHz: 0.90 (d, J=6.6 Hz, 6H); 2.05 (m, 1H); 2.40 (s, 3H); 3.10 (s, 3H); 3.30 (m, masked, 2H); 6.58 (s, 1H); 8.08 (s broad, 1H); 8.13 (s broad, 1H); 8.49 (s broad, 1H); 11.00 (s broad, 1H); 11.80 (s broad, 1H).

EXAMPLE 92

(5Z)-5-[(5-chloro-1H-pyrrolo[2,3-b]pyridin-3-yl)methylidene]-2-phenyl-3,5-dihydro-4H-imidazol-4-one a) (5Z)-5-[(5-chloro-1H-pyrrolo[2,3-b]pyridin-3-yl)methylidene]-2-phenyl-3,5-dihydro-4H-imidazol-4-one can be prepared as in Example 83, but from 2.7 cm$^3$ of 2M ammonia in ethanol and 96 mg of (4Z)-4-[(1-acetyl-5-chloro-1H-pyrrolo[2,3-b]pyridin-3-yl)methylidene]-2-phenyl-1,3-oxazol-5(4H)-one in 4 cm$^3$ of ethanol. After four hours at 170° C. under microwave irradiation and filtration of the solid, 30 mg of (5Z)-5-[(5-chloro-1H-pyrrolo[2,3-b]pyridin-3-yl)methylidene]-2-phenyl-3,5-dihydro-4H-imidazol-4-one is obtained in the form of a yellow powder with the following characteristics:
Melting point: 250° C.
$^1$H-NMR spectrum at 400 MHz: 7.36 (s, 1H); 7.61 (m, 2H); 8.16 (m, 2H); 8.35 (d, J=2.4 Hz, 1H); 8.54 (s, 1H); 9.43 (s, 1H); 11.93 (s broad, 1H); 12.68 (s broad, 1H).

b) (4Z)-4-[(1-acetyl-5-chloro-1H-pyrrolo[2,3-b]pyridin-3-yl)methylidene]-2-phenyl-1,3-oxazol-5(4H)-one can be prepared as in Example 83, but from 208 mg of hippuric acid, 98 mg of potassium acetate and 0.2 g of 5-chloro-1H-pyrrolo[2,3-b]pyridine-3-carbaldehyde in 5 cm$^3$ of acetic anhydride. After 4 hours at 100° C., the reaction mixture is cooled to 25° C. and then diluted with water. The solid is filtered to obtain 222 mg of (4Z)-4-[(1-acetyl-5-chloro-1H-pyrrolo[2,3-b]pyridin-3-yl)methylidene]-2-phenyl-1,3-oxazol-5(4H)-one in the form of orange powder with the following characteristics:
Melting point: 242° C.

EXAMPLE 93

(5Z)-2-[benzyl(methyl)amino]-5-[(5-chloro-1H-pyrrolo[2,3-b]pyridin-3-yl)methylidene]-3,5-dihydro-4H-imidazol-4-one 5Z)-2-[benzyl(methyl)amino]-5-[(5-chloro-1H-pyrrolo[2,3-b]pyridin-3-yl)methylidene]-3,5-dihydro-4H-imidazol-4- one can be prepared as in Example 7, but from 100 mg of (5Z)-5-[(5-chloro-1H-pyrrolo[2,3-b]pyridin-3-yl)methylene]-2-thioxoimidazolidin-4-one (Example 3), 1.5 cm³ of ethanol and 435 mg of N-methyl-1-phenylmethanamine. After ninety minutes at a temperature of 180° C. under microwave irradiation, then filtration of the solid, 39 mg of (5Z)-2-[benzyl(methyl)amino]-5-[(5-chloro-1H-pyrrolo[2,3-b]pyridin-3-yl)methylidene]-3,5-dihydro-4H-imidazol-4-one is obtained in the form of a yellow powder with the following characteristics:
Melting point: 310° C.
¹H-NMR spectrum at 400 MHz: 3.05 (s, 3H); 4.73 (br s, 2H); 6.66 (s, 1H); 7.20-7.47 (m, 5H); 8.21 (s, 2H); 9.06 (s, 1H); 11.22 (br s, 1H); 12.17 (b s, 1H)
Mass spectrum: UPLC-MS-DAD-ELSD: 364(−)=(M−H)(−); 366(+)=(M+H)(+).

EXAMPLE 94

(5Z)-5-[(5-chloro-1H-pyrrolo[2,3-b]pyridin-3-yl)methylidene]-2-[(furan-2-ylmethyl)(methyl)amino]-3,5-dihydro-4H-imidazol-4-one (5Z)-5-[(5-chloro-1H-pyrrolo[2,3-b]pyridin-3-yl)methylidene]-2-[(furan-2-ylmethyl)(methyl)amino]-3,5-dihydro-4H-imidazol-4-one can be prepared as in Example 7, but from 100 mg of (5Z)-5-[(5-chloro-1H-pyrrolo[2,3-b]pyridin-3-yl)methylene]-2-thioxoimidazolidin-4-one (Example 3), 1.5 cm³ of ethanol and 399 mg of 1-furan-2-yl-N-methylmethanamine. After one hour at a temperature of 180° C. under microwave irradiation, then filtration of the solid, 49 mg of (5Z)-5-[(5-chloro-1H-pyrrolo[2,3-b]pyridin-3-yl)methylidene]-2-[(furan-2-ylmethyl)(methyl)amino]-3,5-dihydro-4H-imidazol-4-one is obtained in the form of brown powder with the following characteristics:
Melting point: 315° C.
¹H-NMR spectrum at 400 MHz: 3.07 (s, 3H); 4.71 (b s, 2H); 6.44 (s, 2H); 6.67 (s, 1H); 7.64 (s, 1H); 8.23 (s, 2H); 9.09 (b s, 1H); 11.11 (b s, 1H), 12.15 (b s, 1H).
Mass spectrum: UPLC-MS-DAD-ELSD: 354(−)=(M−H)(−); 356(+)=(M+H)(+).

EXAMPLE 95

(5Z)-5-[(5-chloro-1H-pyrrolo[2,3-b]pyridin-3-yl)methylidene]-2-[(2-methoxyethyl)(methyl)amino]-3,5-dihydro-4H-imidazol-4-one (5Z)-5-[(5-chloro-1H-pyrrolo[2,3-b]pyridin-3-yl)methylidene]-2-[(2-methoxyethyl)(methyl)amino]-3,5-dihydro-4H-imidazol-4-one can be prepared as in Example 7, but from 100 mg of (5Z)-5-[(5-chloro-1H-pyrrolo[2,3-b]pyridin-3-yl)methylene]-2-thioxoimidazolidin-4-one (Example 3), 1.5 cm³ of ethanol and 320 mg of 2-methoxy-N-methylethanamine. After fifteen minutes under microwave irradiation at each of the temperatures of 160, 165, 170, 175 and 180° C., then filtration of the solid, 50 mg of (5Z)-5-[(5-chloro-1H-pyrrolo[2,3-b]pyridin-3-yl)methylidene]-2-[(2-methoxyethyl)(methyl)amino]-3,5-dihydro-4H-imidazol-4-one is obtained in the form of a yellow powder with the following characteristics:
Melting point: 281° C.
¹H-NMR spectrum at 400 MHz: 3.13 (b s, 3H); 3.28-3.30 (m, 2H); 3.58 (b s, 3H); 3.65 (b s, 2H); 6.61 (s, 1H); 8.18 (s, 1H); 8.22 (d, J=2 Hz, 1H); 9.10 (b s, 1H); 11.07 (b s, 1H); 12.18 (b s, 1H).
Mass spectrum: UPLC-MS-DAD-ELSD: 332(−)=(M−H)(−); 334(+)=(M+H) (+).

EXAMPLE 96

(5Z)-5-[(5-chloro-1H-pyrrolo[2,3-b]pyridin-3-yl)methylidene]-2-[methyl(pyridin-2-ylmethyl)amino]-3,5-dihydro-4H-imidazol-4-one (5Z)-5-[(5-chloro-1H-pyrrolo[2,3-b]pyridin-3-yl)methylidene]-2-[methyl(pyridin-2-ylmethyl)amino]-3,5-dihydro-4H-imidazol-4-one can be prepared as in Example 7, but from 100 mg of (5Z)-5-[(5-chloro-1H-pyrrolo[2,3-b]pyridin-3-yl)methylene]-2-thioxoimidazolidin-4-one (Example 3), 1.5 cm³ of ethanol and 439 mg of N-methyl-1-pyridin-2-ylmethanamine. After two hours at a temperature of 180° C. under microwave irradiation, then filtration of the solid, 18 mg of (5Z)-5-[(5-chloro-1H-pyrrolo[2,3-b]pyridin-3-yl)methylidene]-2-[methyl(pyridin-2-ylmethyl)amino]-3,5-dihydro-4H-imidazol-4-one is obtained in the form of a yellow powder with the following characteristics:
Melting point: 350° C.
¹H-NMR spectrum at 400 MHz: 3.07 (s, 3H); 4.78 (s, 2H); 6.68 (s, 1H); 7.40 (dd, J=7.3, 4.9 Hz, 1H); 7.77 (d, J=8.3 Hz, 1H); 8.11-8.27 (m, 2H); 8.51 (d, J=4.4 Hz, 1H); 8.60 (s, 1H); 9.05 (b s, 1H); 11.25 (b s, 1H); 12.20 (b s, 1H)
Mass spectrum: UPLC-MS-DAD-ELSD: 365(−)=(M−H)(−); 367(+)=(M+H) (+).

EXAMPLE 97

(5Z)-5-[(5-chloro-1H-pyrrolo[2,3-b]pyridin-3-yl)methylidene]-2-phenoxy-3-phenyl-3,5-dihydro-4H-imidazol-4-one a) (5Z)-5-[(5-chloro-1H-pyrrolo[2,3-b]pyridin-3-yl)methylidene]-2-phenoxy-3-phenyl-3,5-dihydro-4H-imidazol-4-one can be prepared as in Example 1, but from 42 mg of 5-chloro-1H-pyrrolo[2,3-b]pyridine-3-carbaldehyde in 4 cm³ of ethanol, 59 mg of 2-phenoxy-3-phenyl-3,5-dihydro-4H-imidazol-4-one and 0.023 cm³ of piperidine. After refluxing for five hours, 60 mg of (5Z)-5-[(5-chloro-1H-pyrrolo[2,3-b]pyridin-3-yl)methylidene]-2-phenoxy-3-phenyl-3,5-dihydro-4H-imidazol-4-one is obtained in the form of a pale yellow solid with the following characteristics:
Melting point: 287° C.
¹H-NMR spectrum at 400 MHz: 6.96-7.77 (m, 11H), 8.18 (s, 1H), 8.20 (s, 1H), 8.80 (s, 1H), 12.5 (m spread out, 1H).
Mass spectrum: m/z=414 (M⁺)
b) 2-phenoxy-3-phenyl-3,5-dihydro-4H-imidazol-4-one can be prepared as follows: at a temperature close to 20° C., add 0.1 g of phenol and 7 mg of potassium carbonate to 0.2 g of N-[(phenylimino)methylidene]methylglycinate in solution in 5 cm³ of acetonitrile. After stirring for 24 hours at a temperature close to 55° C., the reaction mixture is concentrated to dryness at reduced pressure to give a residue, which is purified by flash chromatography on an SVL D26 Merck SI60 cartridge 25 g, 15-40 μM, flow rate 20 ml/min, vf 4.3 ml [eluent: ethyl acetate/cyclohexane (1/3 by volume)]. After concentration of the fractions at reduced pressure, a yellow residue is obtained, which is stirred in 5 cm³ of petroleum ether, then filtered and dried at reduced pressure to give 68 mg of 2-phenoxy-3-phenyl-3,5-dihydro-4H-imidazol-4-one, in the form of a pale yellow solid with the following mass spectrum: m/z=252 (M⁺).

c) N-[(phenylimino)methylidene]methylglycinate can be prepared as follows: at a temperature close to 0° C., under an argon atmosphere, add 9.64 g of dibromo-triphenylphosphine and 6.35 cm³ of triethylamine to 3.17 g of N-(phenylcarbamoyl)methylglycinate in suspension in 100 cm³ of dichloromethane. Allow the temperature to return slowly to room temperature. After stirring for 20 hours at a temperature close to 20° C., wash the reaction mixture successively with 50 cm³ of water and 50 cm³ of a saturated aqueous solution of potassium hydrogen carbonate, dry over anhydrous magnesium sulphate, filter and concentrate to dryness at reduced pressure, to give 9.5 g of a brown solid, which is purified by flash chromatography on an EVP D57 Merck SI60 cartridge 200 g, 40-63 µM, flow rate 30 ml/min, vf 17.5 ml [eluent: ethyl acetate/cyclohexane (1/7 by volume)]. After concentration of the fractions at reduced pressure, 1.47 g of N-[(phenylimino) methylidene]methylglycinate is obtained in the form of a pale yellow oil with the following mass spectrum: m/z=190 ($M^+$).

d) N-(phenylcarbamoyl)methylglycinate can be prepared as follows: at a temperature close to 20° C., under an argon atmosphere, add 2.39 cm³ of phenyl isocyanate and 3.34 cm³ of triethylamine to 2.51 g of methylglycinate hydrochloride in suspension in 50 cm³ of dichloromethane. After stirring for 5 hours at a temperature close to 20° C., the reaction mixture is washed with 50 cm³ of water. The aqueous phase is extracted with 2×50 cm³ of dichloromethane. The organic phases are combined, dried over anhydrous magnesium sulphate, filtered and concentrated to dryness at reduced pressure to give a residue, which is washed successively with 5×50 cm³ of petroleum ether and 3×100 cm³ of a petroleum ether/diisopropyl ether mixture (1/1 by volume). After drying at reduced pressure at a temperature close to 20° C., 3.17 g of N-(phenylcarbamoyl)methylglycinate is obtained in the form of a white solid with the following mass spectrum: m/z=208 ($M^+$).

EXAMPLE 98

(5Z)-5-[1-(5-chloro-1H-pyrrolo[2,3-b]pyridin-3-yl)-methylidene]-2-methoxy-3-phenyl-3,5-dihydro-4H-imidazol-4-one a) (5Z)-5-[1-(5-chloro-1H-pyrrolo[2,3-b]pyridin-3-yl)-methylidene]-2-methoxy-3-phenyl-3,5-dihydro-4H-imidazol-4-one can be prepared as in Example 1, but from 34 mg of 5-chloro-1H-pyrrolo[2,3-b]pyridine-3-carbaldehyde in 4 cm³ of ethanol, 36 mg of 2-phenoxy-3-phenyl-3,5-dihydro-4H-imidazol-4-one and 0.02 cm³ of piperidine. After refluxing for five hours, 43 mg of (5Z)-5-[1-(5-chloro-1H-pyrrolo[2,3-b]pyridin-3-yl)-methylidene]-2-methoxy-3-phenyl-3,5-dihydro-4H-imidazol-4-one is obtained in the form of a pale yellow solid with the following characteristics:

Melting point: 227.5° C.
¹H-NMR spectrum at 400 MHz: 4.18 (s, 3H), 7.29 (s, 1H), 7.42 (m, 3H), 7.52 (t, J=7.6 Hz, 2H), 8.31 (s broad, 1H), 8.41 (s, 1H), 9.18 (s broad, 1H), 12.55 (m spread out, 1H).
Mass spectrum: m/z=352 ($M^+$)

b) 2-methoxy-3-phenyl-3,5-dihydro-4H-imidazol-4-one can be prepared as follows: at a temperature close to 20° C., add 9 mg of potassium carbonate to 0.2 g of N-[(phenylimino) methylidene]methylglycinate (prepared as described in Example 97) in solution in 5 cm³ of methanol. After stirring for six hours thirty minutes at a temperature close to 55° C., the reaction mixture is concentrated to dryness at reduced pressure (2.7 kPa) to give a residue, which is purified by flash chromatography on an SVL D26 Merck SI60 cartridge 25 g, 15-40 µM, flow rate 20 ml/min, vf 4.3 ml [eluent: ethyl acetate/cyclohexane (1/1 by volume)]. After concentration of the fractions at reduced pressure, a yellow residue is obtained, which is stirred in 5 cm³ of petroleum ether, then filtered and dried at reduced pressure (2.7 kPa) to give 41 mg of 2-methoxy-3-phenyl-3,5-dihydro-4H-imidazol-4-one in the form of a pale yellow solid with the following mass spectrum: m/z=190 ($M^+$)

EXAMPLE 99

(5Z)-5-[(5-chloro-1H-pyrrolo[2,3-b]pyridin-3-yl) methylidene]-3-methyl-2-phenoxy-3,5-dihydro-4H-imidazol-4-one a) (5Z)-5-[(5-chloro-1H-pyrrolo[2,3-b]pyridin-3-yl)methylidene]-3-methyl-2-phenoxy-3,5-dihydro-4H-imidazol-4-one can be prepared as in Example 1, but from 74 mg of 5-chloro-1H-pyrrolo[2,3-b]pyridine-3-carbaldehyde in 7 cm³ of ethanol, 70 mg of 3-methyl-2-phenoxy-3,5-dihydro-4H-imidazol-4-one and 0.038 cm³ of piperidine. After refluxing for six hours, 48 mg of (5Z)-5-[(5-chloro-1H-pyrrolo[2,3-b]pyridin-3-yl)methylidene]-3-methyl-2-phenoxy-3,5-dihydro-4H-imidazol-4-one is obtained in the form of a pale yellow solid with the following characteristics:

¹H-NMR spectrum at 400 MHz: 3.21 (s, 3H), 7.19 (s, 1H), 7.33-7.62 (m, 5H), 8.12 (s, 1H), 8.19 (s, 1H), 8.79 (s, 1H), 12.45 (m spread out, 1H)

Mass spectrum: m/z=352 ($M^+$)

b) 3-methyl-2-phenoxy-3,5-dihydro-4H-imidazol-4-one can be prepared as follows: at a temperature close to 20° C., add 0.1 g of phenol and 12 mg of potassium carbonate to 0.151 g of N-[(methylimino)methylidene]methylglycinate in solution in 5 cm³ of acetonitrile. After stirring for 6.5 hours at a temperature close to 55° C., the reaction mixture is concentrated to dryness at reduced pressure (2.7 kPa) to give a residue, which is purified by flash chromatography on an SVL D26 Merck SI60 cartridge 25 g, 15-40 µM, flow rate 20 ml/min, vf 4.3 ml [eluent: ethyl acetate/cyclohexane (1/1 by volume)]. After concentration of the fractions at reduced pressure, a yellow residue is obtained, which is stirred in 5 cm³ of petroleum ether, then filtered and dried at reduced pressure (2.7 kPa) to give 149 mg of 3-methyl-2-phenoxy-3, 5-dihydro-4H-imidazol-4-one in the form of a white solid with the following mass spectrum: m/z=190 ($M^+$).

c) N-[(methylimino)methylidene]methylglycinate can be prepared as follows: at a temperature close to 0° C., under an argon atmosphere, add 5.42 g of dibromo-triphenylphosphine and 3.6 cm³ (25.66 mmol) of triethylamine to 1.37 g of N-(methylcarbamoyl)methylglycinate in suspension in 50 cm³ of dichloromethane. Allow the temperature to return slowly to room temperature. After stirring for 24 hours at a temperature close to 20° C., filter the reaction mixture several times on a No. 4 glass frit. The filtrate is taken up in 4×25 cm³ of petroleum ether, filtering each time to remove as much triphenylphosphine oxide as possible. The filtrate is concentrated to dryness at reduced pressure (2.7 kPa) to give 0.74 g of a yellow oil, which is purified by chromatography on 74 g of aluminium oxide (Fluka type 507c neutral) activated with 4.4 cm³ (6%) of water, Patm, vf 20 ml (eluent: dichloromethane). After concentration of the fractions at reduced pressure, 0.48 g of N-[(methylimino)methylidene]methylglycinate is obtained in the form of a pale yellow oil with the following mass spectrum: m/z=142 (M+).

d) N-(methylcarbamoyl)methylglycinate can be prepared as follows: at a temperature close to 20° C., under an argon atmosphere, add 3.9 cm³ of a 2M solution of methylamine in tetrahydrofuran to 1.0 g N-(oxomethylidene)methylglycinate in solution in 8 cm³ of tetrahydrofuran. After stirring for 4 hours at a temperature close to 20° C., filter the reaction mixture on a No. 4 glass frit, then concentrate the filtrate to dryness at reduced pressure (2.7 kPa), to give a white residue, which is stirred with 3×25 cm³ of petroleum ether, then filtered and dried at reduced pressure (2.7 kPa) to give 1.37 g of N-(methylcarbamoyl)methylglycinate in the form of a white solid with the following mass spectrum: m/z=160 (M+.)

EXAMPLE 100

Pharmaceutical Composition

Tablets were prepared, corresponding to the following formula:

| | |
|---|---|
| Product from Example 1 | 0.2 g |
| Excipients for one tablet, to: | 1 g |
| (detailed excipients: lactose, talc, starch, magnesium stearate). | |

EXAMPLE 101

Pharmaceutical Composition

Tablets were prepared, corresponding to the following formula:

| | |
|---|---|
| Product from Example 10 | 0.2 g |
| Excipients for one tablet, to: | 1 g |
| (detailed excipients: lactose, talc, starch, magnesium stearate). | |

Examples 1 and 10 are given as examples of a pharmaceutical preparation, which can be prepared if desired with other products shown as examples in the present application.

What is claimed is:

1. A compound of formula (I):

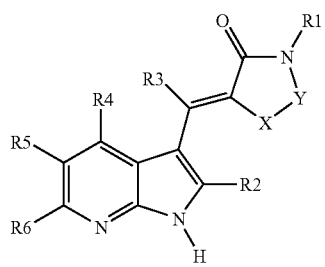

(I)

wherein:
X—Y represents NH—C(S), N═C—NR7R8, N═C—SR, N═C—R or N═C—OR;
R1 represents a hydrogen atom, a cycloalkyl radical or an alkyl, heterocycloalkyl, aryl or heteroaryl radical, all these radicals being optionally substituted;
R, which may be identical to or different from R1, is selected from the values of R1;
R2 represents a hydrogen atom, a halogen atom or an alkyl radical;
R3 represents a hydrogen atom, a halogen atom, a hydroxyl radical or an alkyl or alkoxy radical;
R4 represents a hydrogen atom, a halogen atom or a cyano, CF3 or alkyl radical;
R5 represents a hydrogen atom, a halogen atom, a hydroxyl, cyano, NR7R8, CONR7R8, NR11COR12 radical or optionally substituted cycloalkyl, optionally substituted alkyl, optionally substituted alkoxy, optionally substituted heterocycloalkyl, optionally substituted aryl or optionally substituted heteroaryl radical;
R6 represents a hydrogen atom, a halogen atom or an NR7R8, alkyl or alkoxy radical;
R7 and R8 are such that:
either R7 and R8, which may be identical or different, are such that one of R7 and R8 represents a hydrogen atom or an alkyl radical, optionally substituted;
and the other one of R7 and R8 represents a hydrogen atom or a cycloalkyl, alkyl, heterocycloalkyl, heteroaryl or aryl radical, all these radicals being optionally substituted;
or R7 and R8 form, together with the nitrogen atom to which they are attached, a cyclic radical formed from 3 to 7 ring members optionally containing one or more other heteroatoms selected from O, S or N, N being optionally substituted with R11, said cyclic radical itself being optionally substituted;
all the alkyl, alkoxy, cycloalkyl, heterocycloalkyl, heteroaryl and aryl radicals, as well as the cyclic radical that R7 and R8 can form together with the nitrogen atom to which they are attached, indicated as optionally substituted, thus being optionally substituted with one or more radicals, which may be identical or different, selected from the halogen atoms and the hydroxyl, cyano, nitro, CF3, NR9R10, NHCOR11, NHCO2R11, NHCONR9R10, NHSO2R13, COOH, COOalk, CONR9R10, SO2NR9R10, alkoxy, alkylthio, haloalkoxy, haloalkylthio, alkyl, fluoroalkyl, hydroxyalkyl, cycloalkyl, heterocycloalkyl, heteroaryl and phenyl radicals, these last-mentioned heteroaryl, aryl and phenyl radicals themselves being optionally substituted with one or more radicals, which may be identical or different, selected from the halogen atoms and the hydroxyl, NH2, NH(alk), N(alk)2, alkyl, hydroxyalkyl and alkoxy radicals;
R9 and R10 are such that:
either R9 and R10, which may be identical or different, are such that one of R9 and R10 represents a hydrogen atom or an alkyl radical optionally substituted with one or more radicals, which may be identical or different, selected from the halogen atoms and the hydroxyl and alkoxy radicals;
and the other one of R9 and R10 represents a hydrogen atom or a cycloalkyl, alkyl, heterocycloalkyl, heteroaryl or aryl radical, all these radicals themselves being optionally substituted with one or more radicals, which may be identical or different, selected from the halogen atoms and the hydroxyl, NH2, NH(alk), N(alk)2, alkyl, hydroxyalkyl and alkoxy radicals;
or R9 and R10 form, together with the nitrogen atom to which they are attached, a cyclic radical formed from 3 to 7 ring members optionally containing one or more other heteroatoms selected from O, S or N, N being optionally substituted with R12, said cyclic radical itself being optionally substituted with one or more radicals, which may be identical or different, selected from the halogen atoms and the hydroxyl, NH2, NH(alk), N(alk)2, alkyl, hydroxyalkyl and alkoxy radicals;

R11 and R12, which may be identical or different, represent a hydrogen atom or an alkyl or phenyl radical, optionally substituted with one or more radicals, which may be identical or different, selected from the halogen atoms and the hydroxyl and alkoxy radicals, the phenyl radical itself being optionally substituted with one or more alkyl radicals;

R13 represents an alkyl or phenyl radical, optionally substituted with one or more radicals, which may be identical or different, selected from the halogen atoms and the hydroxyl and alkoxy radicals, the phenyl radical itself being optionally substituted with one or more alkyl radicals;

all the above alkyl (alk) and alkoxy radicals being linear or branched and containing at most 12 carbon atoms;

or a tautomer, racemate, enantiomer or diastereoisomer of the compound of formula (I), or an addition salt with an organic or inorganic acid or organic or inorganic base, of such compound of formula (I), tautomer, racemate, enantiomer or diastereoisomer;

it being understood that the compounds of formula (I) in which all of the following conditions are fulfilled, are excluded:

R2 represents hydrogen;

R3 represents hydrogen or alkyl;

X—Y represents N=C—NR7R8, or N=C—SR in which X represents N and Y represents =C—NR7R8, or =C—SR and R7, R8, and R are as defined above; or X—Y represents N=CR in which X represents N and Y represents =CR and R represents aryl or heteroaryl;

R1 represents H or alk;

and R4, R5 and R6 are such that two of them represent H and the other one represents hydrogen, NH2 or NHalk or NR11COR12, wherein R11 represents a hydrogen atom and R12 represents an alkyl or a phenyl;

or a tautomer, racemate, enantiomer or diastereoisomer of such excluded compounds of formula (I), or an addition salt with an organic or inorganic acid or organic or inorganic base, of such excluded compounds of formula (I), tautomer, racemate, enantiomer or diastereoisomer.

2. A compound according to claim 1 wherein:

R1 represents a hydrogen atom, or an alkyl radical, the alkyl radical being optionally substituted as stated in claim 1;

and R5 represents a hydrogen atom, a hydroxyl, cyano, NR7R8, CF3 radical or optionally substituted cycloalkyl, optionally substituted alkyl, optionally substituted alkoxy, optionally substituted heterocycloalkyl, optionally substituted aryl or optionally substituted heteroaryl radical;

the other substituent radicals R2, R3, R4, R6 and X—Y having the values defined in claim 1;

or a tautomer, racemate, enantiomer or diastereoisomer of such compound, or an addition salt with an organic or inorganic acid or organic or inorganic base, of such compound, tautomer, racemate, enantiomer or diastereoisomer.

3. A compound according to claim 1 wherein:

R2 represents a hydrogen atom;

and R5 represents a halogen atom, a hydroxyl, cyano, NR7R8, CF3 radical or optionally substituted cycloalkyl, optionally substituted alkyl, optionally substituted alkoxy, optionally substituted heterocycloalkyl, optionally substituted aryl or optionally substituted heteroaryl radical;

the other substituent radicals R1, R3, R4, R6 and X—Y having the values defined in claim 1;

or a tautomer, racemate, enantiomer or diastereoisomer of such compound, or an addition salt with an organic or inorganic acid or organic or inorganic base, of such compound, tautomer, racemate, enantiomer or diastereoisomer.

4. A compound according to claim 1 wherein:

R3 represents a hydrogen atom;

and R5 represents a halogen atom, a hydroxyl, cyano, CONR7R8 radical or optionally substituted cycloalkyl, optionally substituted alkyl, optionally substituted alkoxy, optionally substituted heterocycloalkyl, optionally substituted aryl or optionally substituted heteroaryl radical;

the other radicals R2, R3, R4, R6 and X—Y having the values defined in claim 1;

or a tautomer, racemate, enantiomer or diastereoisomer of such compound, or an addition salt with an organic or inorganic acid or organic or inorganic base, of such compound, tautomer, racemate, enantiomer or diastereoisomer.

5. A compound according to claim 1 wherein:

X—Y represents NH—C(S), N=C—NR7R8 or N=C—R;

R1 represents a hydrogen atom, a cycloalkyl radical or an alkyl, heterocycloalkyl, aryl or heteroaryl radical, all these radicals being optionally substituted as stated in claim 1;

R, which may be identical to or different from R1, is selected from the values of R1 as defined in claim 1 with the exception of aryl and heteroaryl;

the other substituents R2, R3, R4, R5 and R6 having the values defined in claim 1;

or a tautomer, racemate, enantiomer or diastereoisomer of such compound, or an addition salt with an organic or inorganic acid or organic or inorganic base, of such compound, tautomer, racemate, enantiomer or diastereoisomer.

6. A compound according to claim 1 wherein:

X—Y represents NH—C(S), N=C—NR7R8, N=C—SR, N=C—R or N=C—OR;

R1 represents a hydrogen atom, a cycloalkyl radical or an alkyl, heterocycloalkyl, phenyl or heteroaryl radical, these last-mentioned radicals being optionally substituted;

R, which may be identical to or different from R1, is selected from the values of R1;

R2 represents a hydrogen atom, a halogen atom or an alkyl radical;

R3 represents a hydrogen atom, a halogen atom, a hydroxyl radical or an alkyl or alkoxy radical;

R4 represents a hydrogen atom, a halogen atom or a cyano, CF3 or alkyl radical;

R5 represents a hydrogen atom, a halogen atom, a hydroxyl, cyano, NR7R8, CONR7R8, NR11COR12 radical or optionally substituted cycloalkyl, optionally substituted alkyl, optionally substituted alkoxy, optionally substituted heterocycloalkyl, optionally substituted phenyl or optionally substituted heteroaryl radical;

R6 represents a hydrogen atom, a halogen atom or an NR7R8, alkyl or alkoxy radical;

R7 and R8 are such that:
either R7 and R8, which may be identical or different, are such that one of R7 and R8 represents a hydrogen atom or an alkyl radical optionally substituted with one or more radicals, which may be identical or different, selected from the halogen atoms and the hydroxyl and alkoxy radicals;
and the other one of R7 and R8 represents a hydrogen atom or a cycloalkyl, alkyl, heterocycloalkyl, heteroaryl or phenyl radical, all these radicals being optionally substituted;
or R7 and R8 form, together with the nitrogen atom to which they are attached, a cyclic radical formed from 3 to 7 ring members optionally containing one or more other heteroatoms selected from O, S or N, N being optionally substituted with R11, said cyclic radical itself being optionally substituted;
all the alkyl, alkoxy, cycloalkyl, heterocycloalkyl, heteroaryl and aryl radicals, as well as the cyclic radical that R7 and R8 can form together with the nitrogen atom to which they are attached, indicated as optionally substituted, thus being optionally substituted with one or more radicals, which may be identical or different, selected from the halogen atoms and the hydroxyl, cyano, nitro, CF3, NR9R10, NHCOR11, NHSO2R13, COOH, COOalk, CONR9R10, SO2NR9R10, alkoxy, haloalkoxy, alkyl, fluoroalkyl, hydroxyalkyl, cycloalkyl, heterocycloalkyl, heteroaryl and phenyl radicals, these last-mentioned heteroaryl and phenyl radicals themselves being optionally substituted with one or more radicals, which may be identical or different, selected from the halogen atoms and the hydroxyl, NH2, NH(alk), N(alk)2, alkyl, hydroxyalkyl and alkoxy radicals;
R9 and R10 are such that:
either R9 and R10, which may be identical or different, are such that one of R9 and R10 represents a hydrogen atom or an alkyl radical and the other one of R9 and R10 represents a hydrogen atom or an alkyl, phenyl or phenylalkyl radical, themselves optionally substituted with one or more radicals, which may be identical or different, selected from the halogen atoms and the hydroxyl, NH2, NH(alk), N(alk)2, alkyl, hydroxyalkyl and alkoxy radicals;
or R9 and R10 form, together with the nitrogen atom to which they are attached, a pyrrolidinyl, morpholine, piperidyl, azepinyl or piperazinyl radical optionally substituted with an alkyl or phenyl radical, itself optionally substituted with one or more radicals, which may be identical or different, selected from the halogen atoms and the alkyl, hydroxyl, NH2, NH(alk), N(alk)2, alkyl, hydroxyalkyl and alkoxy radicals;
R11 and R12, which may be identical or different, represent a hydrogen atom or an alkyl or phenyl radical;
R13 represents an alkyl or phenyl radical;
all the above alkyl (alk) and alkoxy radicals being linear or branched and containing at most 6 carbon atoms;
or a tautomer, racemate, enantiomer or diastereoisomer of such compound, or an addition salt with an organic or inorganic acid or organic or inorganic base, of such compound, tautomer, racemate, enantiomer or diastereoisomer.

7. A compound according to claim 1 wherein: X—Y represents NH—C(S), N=C—NR7R8, N=C—SR, N=C—R or N=C—OR;
R1 represents a hydrogen atom or an alkyl or phenyl radical, optionally substituted;
R represents a hydrogen atom; a cycloalkyl radical; an alkyl, heterocycloalkyl, phenyl, or heteroaryl radical, all these radicals being optionally substituted;
R2 represents a hydrogen atom, a halogen atom or an alkyl radical;
R3 represents a hydrogen atom, a halogen atom, a hydroxyl radical or an alkyl radical;
R4 represents a hydrogen atom, a halogen atom or an alkyl radical;
R5 represents a hydrogen atom; a halogen atom; a hydroxyl, cyano, NR7R8, alkyl, alkoxy, heterocycloalkyl, phenyl, or heteroaryl radical, the alkyl, alkoxy, heterocycloalkyl, phenyl, or heteroaryl radical, as well as the phenyl residue in NHphenyl and NH(phenylalk) being optionally substituted;
R6 represents a hydrogen atom, a halogen atom, or an NH2, NHalk, N(alk)2, alkyl or alkoxy radical;
R7 and R8 are such that:
either R7 and R8, which may be identical or different, are such that one of R7 and R8 represents a hydrogen atom or an alkyl radical;
and the other one of R7 and R8 represents a hydrogen atom, or an alkyl or cycloalkyl radical, optionally substituted;
or R7 and R8 form, together with the nitrogen atom to which they are attached, a cyclic radical selected from the azetidyl, piperidyl, azepanyl, morpholinyl, thiomorpholinyl, pyrrolidinyl, imidazolidinyl, piperazinyl radicals optionally substituted on its second nitrogen atom with an alkyl or phenyl radical, themselves optionally substituted; and homopiperazinyl, these radicals being optionally substituted;
all the alkyl, alkoxy, heterocycloalkyl, heteroaryl and phenyl radicals, as well as the cyclic radical that R7 and R8 can form together with the nitrogen atom to which they are attached, indicated as optionally substituted, thus being optionally substituted with one or more radicals, which may be identical or different, selected from the halogen atoms and the hydroxyl, NH2, NH(alk), N(alk)2, NHphenyl, NH(phenylalk), alkyl, CF3, alkoxy, OCF3, cycloalkyl, heterocycloalkyl, heteroaryl and phenyl radicals; these last-mentioned heteroaryl and phenyl radicals, as well as the phenyl residue in the NHphenyl and NH(phenylalk) radicals, themselves being optionally substituted with one or more radicals, which may be identical or different, selected from the halogen atoms and the hydroxyl, NH2, NHAlk, N(Alk)2, alkyl, hydroxyalkyl and alkoxy radicals;
all the above alkyl (alk) and alkoxy radicals being linear or branched and containing at most 6 carbon atoms;
or a tautomer, racemate, enantiomer or diastereoisomer of such compound, or an addition salt with an organic or inorganic acid or organic or inorganic base, of such compound, tautomer, racemate, enantiomer or diastereoisomer.

8. A compound according to claim 1 wherein:
X—Y represents NH—C(S), N=C—NR7R8, N=C—SR, N=C—R or N=C—OR;
R1 represents a hydrogen atom or an alkyl or phenyl radical, optionally substituted;
R, which may be identical to or different from R1, is selected from the values of R1;
R2 represents a hydrogen atom, a halogen atom or an alkyl radical;
R3 represents a hydrogen atom, a halogen atom, a hydroxyl radical or an alkyl radical;
R4 represents a hydrogen atom, a halogen atom or an alkyl radical;

R5 represents a hydrogen atom, a halogen atom, a hydroxyl radical, an NH2, NHalk, N(alk)2, NR7R8, NHphenyl, NH(phenylalk) radical or an alkyl, heterocycloalkyl, alkoxy, phenyl or heteroaryl radical, said alkyl, heterocyloalkyl, alkoxy, phenyl and heteroaryl radical, as well as the phenyl residue in NHphenyl and NH(phenylalk) being optionally substituted;

R6 represents a hydrogen atom, a halogen atom, or an NH2, NHalk, N(alk)2, alkyl or alkoxy radical;

R7 and R8 are such that:

either R7 and R8, which may be identical or different, are such that one of R7 and R8 represents a hydrogen atom or an alkyl radical;

and the other one of R7 and R8 represents a hydrogen atom, or an alkyl or cycloalkyl radical, optionally substituted;

or R7 and R8 form, together with the nitrogen atom to which they are attached, a cyclic radical containing 4 to 6 ring members selected from azetidyl; piperidyl; morpholinyl; thiomorpholinyl; pyrrolidinyl; imidazolidinyl; piperazinyl; and homopiperazinyl, these radicals being optionally substituted;

all the alkyl, alkoxy, heteroaryl and phenyl radicals, as well as the cyclic radical that R7 and R8 can form together with the nitrogen atom to which they are attached, indicated as optionally substituted, thus being optionally substituted with one or more radicals, which may be identical or different, selected from the halogen atoms and the hydroxyl, NH2, NH(alk), N(alk)2, NHphenyl, NH(phenylalk), alkyl, CF3, alkoxy, OCF3, cycloalkyl, heterocycloalkyl, heteroaryl and phenyl radicals; these last-mentioned heteroaryl and phenyl radicals, as well as the phenyl residue in the NHphenyl and NH(phenylalk) radicals, themselves being optionally substituted with one or more radicals, which may be identical or different, selected from the halogen atoms and the hydroxyl, NH2, NHAlk, N(Alk)2, alkyl, hydroxyalkyl and alkoxy radicals;

all the above alkyl (alk) and alkoxy radicals being linear or branched and containing at most 6 carbon atoms;

or a tautomer, racemate, enantiomer or diastereoisomer of such compound, or an addition salt with an organic or inorganic acid or organic or inorganic base, of such compound, tautomer, racemate, enantiomer or diastereoisomer.

9. A compound according to claim 1 wherein: X—Y, R2, R3, R4 and R6 have the meanings stated in claim 1;

R1 represents a hydrogen atom or an alkyl radical, optionally substituted;

R5 represents a hydrogen atom, a halogen atom, a hydroxyl radical, CF3, NH2, NHalk, N(alk)2 or an alkyl, alkoxy or phenyl radical, optionally substituted;

the alkyl radical that can be represented by R1 or the alkyl, alkoxy or phenyl radical that can be represented by R5, being optionally substituted with one or more radicals, which may be identical or different, selected from the halogen atoms and the hydroxyl, NHalk, N(alk)2, alkoxy, cycloalkyl, heterocycloalkyl, heteroaryl and phenyl radicals, these last-mentioned heteroaryl and phenyl radicals being optionally substituted with one or more radicals, which may be identical or different, selected from the halogen atoms and the hydroxyl, NH2, NHAlk, N(Alk)2, alkyl, hydroxyalkyl and alkoxy radicals;

R7 and R8 are such that:

either R7 and R8, which may be identical or different, are such that one of R7 and R8 represents a hydrogen atom or an alkyl radical, and the other one of R7 and R8 represents a hydrogen atom, an alkyl radical optionally substituted with one or more radicals, which may be identical or different, selected from the halogen atoms, the hydroxyl, NH2, NHalk, N(alk)2, NH(phenyl), NH(phenylalk), alkoxy, OCF3, cycloalkyl radicals, and the pyrrolidinyl, piperazinyl, piperidyl, morpholinyl and phenyl radicals, all these last-mentioned cyclic radicals, as well as the phenyl residue in the phenylalkyl radical, themselves being optionally substituted with one or more radicals, which may be identical or different, selected from the halogen atoms and the hydroxyl, NH2, NHAlk, N(alk)2, alkoxy, alkyl and hydroxyalkyl radicals;

or R7 and R8 form, together with the nitrogen atom to which they are attached, a radical preferably selected from the piperidyl, morpholinyl radicals, and the pyrrolidinyl, piperazinyl and homopiperazinyl radicals, optionally substituted with one or more radicals, which may be identical or different, selected from the alkyl and phenyl radicals, themselves optionally substituted with one or more radicals selected from the halogen atoms and the hydroxyl, NH2, NHAlk, N(Alk)2, alkoxy and cycloalkyl radicals;

all the above alkyl (alk) and alkoxy radicals being linear or branched and containing at most 6 carbon atoms;

or a tautomer, racemate, enantiomer or diastereoisomer of such compound, or an addition salt with an organic or inorganic acid or organic or inorganic base, of such compound, tautomer, racemate, enantiomer or diastereoisomer.

10. A compound according to claim 1 wherein:

X—Y represents NH—C(S), N=C—NR7R8 or N=C—R,

R7, R8 and R being selected from all the values defined in claim 1 for R7, R8 and R and the other substituents R1, R2, R3, R4, R5 and R6 of said products of formula (I) being selected from all the values defined in any one of the other claims respectively for R1, R2, R3, R4, R5 and R6, or a tautomer, racemate, enantiomer or diastereoisomer of such compound, or an addition salt with an organic or inorganic acid or organic or inorganic base, of such compound, tautomer, racemate, enantiomer or diastereoisomer.

11. A compound according to claim 1 wherein:

X—Y represents NH—C(S), N=C—NR7R8 or N=C—R;

R1 represents a hydrogen atom or an alkyl radical optionally substituted with one or more radicals, which may be identical or different, selected from the halogen atoms and the N(alk)2 and alkoxy radicals;

R, which may be identical to or different from R1, is selected from the values of R1;

R2 represents a hydrogen atom, a halogen atom or an alkyl radical;

R3 represents a hydrogen atom or an alkyl radical;

R4 represents a hydrogen atom or a halogen atom,

R5 represents a hydrogen atom, a halogen atom or a hydroxyl, NH2, NHalk, N(alk)2, alkyl, alkoxy or phenyl radical, the alkyl radical being optionally substituted with an alkoxy, N(alk)2 or heterocycloalkyl radical and the phenyl radical being optionally substituted with one or more radicals, which may be identical or different, selected from the halogen atoms and the hydroxyl, NH2, NHalk, N(alk)2, alkyl and alkoxy radicals;

R6 represents a hydrogen atom, a halogen atom or an alkyl radical;

and R7 and R8 are such that:
either R7 and R8, which may be identical or different, are such that one of R7 and R8 represents a hydrogen atom or an alkyl radical, and the other one of R7 and R8 represents an alkyl radical optionally substituted with a cycloalkyl radical;
or R7 and R8 form, together with the nitrogen atom to which they are attached, a pyrrolidinyl, morpholine, piperidyl or piperazinyl radical optionally substituted with an alkyl radical;
or a tautomer, racemate, enantiomer or diastereoisomer of such compound, or an addition salt with an organic or inorganic acid or organic or inorganic base, of such compound, tautomer, racemate, enantiomer or diastereoisomer.

12. A compound according to claim 1 wherein:
X—Y represents NH—C(S) or N═C—NR7R8;
R1 and R2 which may be identical or different, represents a hydrogen atom or an alkyl radical;
R3 represents a hydrogen atom;
R4, R5 and R6, which may be identical or different, represent a hydrogen atom or a halogen atom;
R7 and R8 represent the values defined in claim 1;
all the above alkyl (alk) radicals being linear or branched and containing at most 6 carbon atoms;
or a tautomer, racemate, enantiomer or diastereoisomer of such compound, or an addition salt with an organic or inorganic acid or organic or inorganic base, of such compound, tautomer, racemate, enantiomer or diastereoisomer.

13. A compound according to claim 1 which is:
(5Z)-5-[(5-chloro-1H-pyrrolo[2,3-b]pyridin-3-yl)methylene]-2-thioxoimidazolidin-4-one;
(5Z)-5-[(5-chloro-1H-pyrrolo[2,3-b]pyridin-3-yl)methylene]-2-[(cyclopropylmethyl)amino]-3,5-dihydro-4H-imidazol-4-one;
(5Z)-5-[(6-chloro-1H-pyrrolo[2,3-b]pyridin-3-yl)methylene]-2-[(cyclopropylmethyl)amino]-3,5-dihydro-4H-imidazol-4-one;
(5Z)-2-butyl-5-(1H-pyrrolo[2,3-b]pyridin-3-ylmethylene)-3,5-dihydro-4H-imidazol-4-one;
(5Z)-2-azepan-1-yl-5-[(5-chloro-1H-pyrrolo[2,3-b]pyridin-3-yl)methylidene]-3,5-dihydro-4H-imidazol-4-one;
5Z)-5-[(5-chloro-1H-pyrrolo[2,3-b]pyridin-3-yl)methylidene]-2-piperidin-1-yl-3,5-dihydro-4H-imidazol-4-one;
(5Z)-5-[(5-chloro-1H-pyrrolo[2,3-b]pyridin-3-yl)methylidene]-2-[methyl(2-methylpropyl)amino]-3,5-dihydro-4H-imidazol-4-one;
(5Z)-5-[(5-bromo-1H-pyrrolo[2,3-b]pyridin-3-yl)methylidene]-2-[(cyclopropylmethyl)amino]-3,5-dihydro-4H-imidazol-4-one;
(5Z)-2-[(cyclopropylmethyl)amino]-5-[(5-methoxy-1H-pyrrolo[2,3-b]pyridin-3-yl)methylidene]-3,5-dihydro-4H-imidazol-4-one;
(5Z)-2-[(cyclopropylmethyl)amino]-5-[(5-fluoro-1H-pyrrolo[2,3-b]pyridin-3-yl)methylidene]-3,5-dihydro-4H-imidazol-4-one;
(5Z)-2-azepan-1-yl-5-[(5-fluoro-1H-pyrrolo[2,3-b]pyridin-3-yl)methylidene]-3,5-dihydro-4H-imidazol-4-one;
3-[(Z)-{2-[(cyclopropylmethyl)amino]-5-oxo-1,5-dihydro-4H-imidazol-4-ylidene}methyl]-1H-pyrrolo[2,3-b]pyridine-5-carbonitrile;
(5Z)-2-[(cyclopropylmethyl)amino]-5-[(5-phenyl-1H-pyrrolo[2,3-b]pyridin-3-yl)methylidene]-3,5-dihydro-4H-imidazol-4-one;
(5Z)-2-[(cyclopropylmethyl)amino]-5-{[5-(trifluoromethyl)-1H-pyrrolo[2,3-b]pyridin-3-yl]methylidene}-3,5-dihydro-4H-imidazol-4-one;
(5Z)-5-[(5-chloro-1H-pyrrolo[2,3-b]pyridin-3-yl)methylidene]-2-(methylsulphanyl)-3,5-dihydro-4H-imidazol-4-one;
(5Z)-2-butyl-5-[(5-chloro-1H-pyrrolo[2,3-b]pyridin-3-yl)methylidene]-3,5-dihydro-4H-imidazol-4-one;
(5Z)-2-(3-methylbutyl)-5-(1H-pyrrolo[2,3-b]pyridin-3-ylmethylidene)-3,5-dihydro-4H-imidazol-4-one;
(5Z)-2-cyclohexyl-5-(1H-pyrrolo[2,3-b]pyridin-3-ylmethylidene)-3,5-dihydro-4H-imidazol-4-one;
(5Z)-5-[(5-chloro-1H-pyrrolo[2,3-b]pyridin-3-yl)methylidene]-3-methyl-2-(tetrahydro-2H-pyran-4-yl)-3,5-dihydro-4H-imidazol-4-one;
(5Z)-5-[(5-chloro-1H-pyrrolo[2,3-b]pyridin-3-yl)methylidene]-3-methyl-2-(2-methylpropyl)-3,5-dihydro-4H-imidazol-4-one;
(5Z)-2-(cyclopropylmethyl)-5-(5-chloro-1H-pyrrolo[2,3-b]pyridin-3-ylmethylidene)-3,5-dihydro-4H-imidazol-4-one;
(5Z)-2-(1-methylethyl)-5-(5-chloro-1H-pyrrolo[2,3-b]pyridin-3-ylmethylidene)-3,5-dihydro-4H-imidazol-4-one;
(5Z)-2-[benzyl(methyl)amino]-5-[(5-chloro-1H-pyrrolo[2,3-b]pyridin-3-yl)methylidene]-3,5-dihydro-4H-imidazol-4-one; or
(5Z)-5-[(5-chloro-1H-pyrrolo[2,3-b]pyridin-3-yl)methylidene]-2-[(2-methoxyethyl)(methyl)amino]-3,5-dihydro-4H-imidazol-4-one;
or a tautomer, racemate, enantiomer or diastereoisomer of such compound, or an addition salt with an organic or inorganic acid or organic or inorganic base, of such compound, tautomer, racemate, enantiomer or diastereoisomer.

14. A compound according to claim 1 wherein said addition salt with an organic or inorganic acid or organic or inorganic base is pharmaceutically acceptable.

15. A compound according to claim 13 wherein said addition salt with an organic or inorganic acid or organic or inorganic base is pharmaceutically acceptable.

16. A pharmaceutical composition comprising a compound of formula (I):

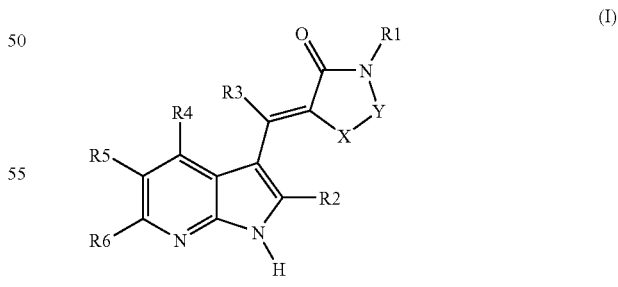

wherein:
X—Y represents NH—C(S), N═C—NR7R8, N═C—SR, N═C—R
or N═C—OR;
R1 represents a hydrogen atom, a cycloalkyl radical or an alkyl, heterocycloalkyl, aryl or heteroaryl radical, all these radicals being optionally substituted;

R, which may be identical to or different from R1, is selected from the values of R1;

R2 represents a hydrogen atom, a halogen atom or an alkyl radical;

R3 represents a hydrogen atom, a halogen atom, a hydroxyl radical or an alkyl or alkoxy radical;

R4 represents a hydrogen atom, a halogen atom or a cyano, CF3 or alkyl radical;

R5 represents a hydrogen atom, a halogen atom, a hydroxyl, cyano, NR7R8, CONR7R8, NR11COR12 radical or optionally substituted cycloalkyl, optionally substituted alkyl, optionally substituted alkoxy, optionally substituted heterocycloalkyl, optionally substituted aryl or optionally substituted heteroaryl radical;

R6 represents a hydrogen atom, a halogen atom or an NR7R8, alkyl or alkoxy radical;

R7 and R8 are such that:

either R7 and R8, which may be identical or different, are such that one of R7 and R8 represents a hydrogen atom or an alkyl radical, optionally substituted;

and the other one of R7 and R8 represents a hydrogen atom or a cycloalkyl, alkyl, heterocycloalkyl, heteroaryl or aryl radical, all these radicals being optionally substituted;

or R7 and R8 form, together with the nitrogen atom to which they are attached, a cyclic radical formed from 3 to 7 ring members optionally containing one or more other heteroatoms selected from O, S or N, N being optionally substituted with R11, said cyclic radical itself being optionally substituted;

all the alkyl, alkoxy, cycloalkyl, heterocycloalkyl, heteroaryl and aryl radicals, as well as the cyclic radical that R7 and R8 can form together with the nitrogen atom to which they are attached, indicated as optionally substituted, thus being optionally substituted with one or more radicals, which may be identical or different, selected from the halogen atoms and the hydroxyl, cyano, nitro, CF3, NR9R10, NHCOR11, NHCO2R11, NHCONR9R10, NHSO2R13, COOH, COOalk, CONR9R10, SO2NR9R10, alkoxy, alkylthio, haloalkoxy, haloalkylthio, alkyl, fluoroalkyl, hydroxyalkyl, cycloalkyl, heterocycloalkyl, heteroaryl and phenyl radicals, these last-mentioned heteroaryl, aryl and phenyl radicals themselves being optionally substituted with one or more radicals, which may be identical or different, selected from the halogen atoms and the hydroxyl, NH2, NH(alk), N(alk)2, alkyl, hydroxyalkyl and alkoxy radicals;

R9 and R10 are such that:

either R9 and R10, which may be identical or different, are such that one of R9 and R10 represents a hydrogen atom or an alkyl radical optionally substituted with one or more radicals, which may be identical or different, selected from the halogen atoms and the hydroxyl and alkoxy radicals;

and the other one of R9 and R10 represents a hydrogen atom or a cycloalkyl, alkyl, heterocycloalkyl, heteroaryl or aryl radical, all these radicals themselves being optionally substituted with one or more radicals, which may be identical or different, selected from the halogen atoms and the hydroxyl, NH2, NH(alk), N(alk)2, alkyl, hydroxyalkyl and alkoxy radicals;

or R9 and R10 form, together with the nitrogen atom to which they are attached, a cyclic radical formed from 3 to 7 ring members optionally containing one or more other heteroatoms selected from O, S or N, N being optionally substituted with R12, said cyclic radical itself being optionally substituted with one or more radicals, which may be identical or different, selected from the halogen atoms and the hydroxyl, NH2, NH(alk), N(alk)2, alkyl, hydroxyalkyl and alkoxy radicals;

R11 and R12, which may be identical or different, represent a hydrogen atom or an alkyl or phenyl radical, optionally substituted with one or more radicals, which may be identical or different, selected from the halogen atoms and the hydroxyl and alkoxy radicals, the phenyl radical itself being optionally substituted with one or more alkyl radicals;

R13 represents an alkyl or phenyl radical, optionally substituted with one or more radicals, which may be identical or different, selected from the halogen atoms and the hydroxyl and alkoxy radicals, the phenyl radical itself being optionally substituted with one or more alkyl radicals;

all the above alkyl (alk) and alkoxy radicals being linear or branched and containing at most 12 carbon atoms;

or a tautomer, racemate, enantiomer or diastereoisomer of such compound, or an addition salt with an organic or inorganic acid or organic or inorganic base, of such compound of formula (I)tautomer, racemate, enantiomer or diastereoisomer.

it being understood that the compounds of formula (I) in which all of the following conditions are fulfilled, are excluded:

R2 represents hydrogen;

R3 represents hydrogen or alkyl;

X—Y represents N=C—NR7R8, or N=C—SR in which X represents N and Y represents =C—NR7R8, or =C—SR and R7, R8, and R are as defined above; or X—represents N=CR in which X represents N and Y represents =CR and R represents aryl or heteroaryl;

R1 represents H or alk;

and R4, R5 and R6 are such that two of them represent H and the other one represents hydrogen, NH2 or NHalk or NR11COR12, wherein R11 represents a hydrogen atom and R12 represents an alkyl or a phenyl;

or a tautomer, racemate, enantiomer or diastereoisomer of such compound, or a prodrug of such compound, tautomer, racemate, enantiomer or diastereomer, or a pharmaceutically acceptable addition salt with an organic or inorganic acid or organic or inorganic base, of such compound, tautomer, racemate, enantiomer, diastereoisomer, or prodrug, and a pharmaceutically acceptable carrier.

17. A pharmaceutical composition comprising a compound which is (5Z)-5-[(5-chloro-1H-pyrrolo[2,3-b]pyridin-3-yl)methylene]-2-thioxoimidazolidin-4-one;

(5Z)-5-[(5-chloro-1H-pyrrolo[2,3-b]pyridin-3-yl)methylene]-2-[(cyclopropylmethyl)amino]-3,5-dihydro-4H-imidazol-4-one;

(5Z)-5-[(6-chloro-1H-pyrrolo[2,3-b]pyridin-3-yl)methylene]-2-[(cyclopropylmethyl)amino]-3,5-dihydro-4H-imidazol-4-one;

(5Z)-2-butyl-5-(1H-pyrrolo[2,3-b]pyridin-3-ylmethylene)-3,5-dihydro-4H-imidazol-4-one;

(5Z)-2-azepan-1-yl-5-[(5-chloro-1H-pyrrolo[2,3-b]pyridin-3-yl)methylidene]-3,5-dihydro-4H-imidazol-4-one;

(5Z)-5-[(5-chloro-1H-pyrrolo[2,3-b]pyridin-3-yl)methylidene]-2-piperidin-1-yl-3,5-dihydro-4H-imidazol-4-one;

(5Z)-5-[(5-chloro-1H-pyrrolo[2,3-b]pyridin-3-yl)methylidene]-2-[methyl(2-methylpropyl)amino]-3,5-dihydro-4H-imidazol-4-one;

(5Z)-5-[(5-bromo-1H-pyrrolo[2,3-b]pyridin-3-yl)methylidene]-2-[(cyclopropylmethyl)amino]-3,5-dihydro-4H-imidazol-4-one;

(5Z)-2-[(cyclopropylmethyl)amino]-5-[(5-methoxy-1H-pyrrolo[2,3-b]pyridin-3-yl)methylidene]-3,5-dihydro-4H-imidazol-4-one;

(5Z)-2-[(cyclopropylmethyl)amino]-5-[(5-fluoro-1H-pyrrolo[2,3-b]pyridin-3-yl)methylidene]-3,5-dihydro-4H-imidazol-4-one;

(5Z)-2-azepan-1-yl-5-[(5-fluoro-1H-pyrrolo[2,3-b]pyridin-3-yl)methylidene]-3,5-dihydro-4H-imidazol-4-one;

3-[(Z)-{2-[(cyclopropylmethyl)amino]-5-oxo-1,5-dihydro-4H-imidazol-4-ylidene}methyl]-1H-pyrrolo[2,3-b]pyridine-5-carbonitrile;

(5Z)-2-[(cyclopropylmethyl)amino]-5-[(5-phenyl-1H-pyrrolo[2,3-b]pyridin-3-yl)methylidene]-3,5-dihydro-4H-imidazol-4-one;

(5Z)-2-[(cyclopropylmethyl)amino]-5-{[5-(trifluoromethyl)-1H-pyrrolo[2,3-b]pyridin-3-yl]methylidene}-3,5-dihydro-4H-imidazol-4-one;

(5Z)-5-[(5-chloro-1H-pyrrolo[2,3-b]pyridin-3-yl)methylidene]-2-(methylsulphanyl)-3,5-dihydro-4H-imidazol-4-one;

(5Z)-2-butyl-5-[(5-chloro-1H-pyrrolo[2,3-b]pyridin-3-yl)methylidene]-3,5-dihydro-4H-imidazol-4-one;

(5Z)-2-(3-methylbutyl)-5-(1H-pyrrolo[2,3-b]pyridin-3-ylmethylidene)-3,5-dihydro-4H-imidazol-4-one;

(5Z)-2-cyclohexyl-5-(1H-pyrrolo[2,3-b]pyridin-3-ylmethylidene)-3,5-dihydro-4H-imidazol-4-one;

(5Z)-5-[(5-chloro-1H-pyrrolo[2,3-b]pyridin-3-yl)methylidene]-3-methyl-2-(tetrahydro-2H-pyran-4-yl)-3,5-dihydro-4H-imidazol-4-one;

(5Z)-5-[(5-chloro-1H-pyrrolo[2,3-b]pyridin-3-yl)methylidene]-3-methyl-2-(2-methylpropyl)-3,5-dihydro-4H-imidazol-4-one;

(5Z)-2-(cyclopropylmethyl)-5-(5-chloro-1H-pyrrolo[2,3-b]pyridin-3-ylmethylidene)-3,5-dihydro-4H-imidazol-4-one;

(5Z)-2-(1-methylethyl)-5-(5-chloro-1H-pyrrolo[2,3-b]pyridin-3-ylmethylidene)-3,5-dihydro-4H-imidazol-4-one;

(5Z)-2-[benzyl(methyl)amino]-5-[(5-chloro-1H-pyrrolo[2,3-b]pyridin-3-yl)methylidene]-3,5-dihydro-4H-imidazol-4-one; or (5Z)-5-[(5-chloro-1H-pyrrolo[2,3-b]pyridin-3-yl)methylidene]-2-[(2-methoxyethyl)(methyl)amino]-3,5-dihydro-4H-imidazol-4-one;

or a tautomer, racemate, enantiomer or diastereoisomer of such compound, or a prodrug of such compound, tautomer, racemate, enantiomer or diastereomer, or a pharmaceutically acceptable addition salt with an organic or inorganic acid or organic or inorganic base, of such compound, tautomer, racemate, enantiomer, diastereoisomer, or prodrug, and a pharmaceutically acceptable carrier.

\* \* \* \* \*